United States Patent
Hao et al.

(10) Patent No.: US 10,656,159 B2
(45) Date of Patent: *May 19, 2020

(54) IMMUNOASSAYS OF S-ADENOSYLMETHIONINE AND METHYLATION INDEX IN PERSONALIZED MEDICINE AND HEALTH EVALUATION

(71) Applicants: Xiujuan Hao, Chantilly, VA (US); Isaac A Angres, Arlington, VA (US)

(72) Inventors: Xiujuan Hao, Chantilly, VA (US); Isaac A Angres, Arlington, VA (US)

(73) Assignee: HUNAN SKYWORLD BIOTECHNOLOGIES CO, Changsha (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/888,455

(22) Filed: Feb. 5, 2018

(65) Prior Publication Data

US 2018/0156816 A1    Jun. 7, 2018

Related U.S. Application Data

(60) Division of application No. 14/732,775, filed on Jun. 7, 2015, now Pat. No. 9,885,723, which is a continuation-in-part of application No. 14/457,099, filed on Aug. 11, 2014, now Pat. No. 9,958,447, which is a continuation-in-part of application No. 14/218,928, filed on Mar. 18, 2014, now Pat. No. 9,877,982.

(60) Provisional application No. 61/801,547, filed on Mar. 15, 2013.

(51) Int. Cl.

| G01N 33/68 | (2006.01) |
|---|---|
| C07K 16/44 | (2006.01) |
| A61K 31/7076 | (2006.01) |
| C07H 19/16 | (2006.01) |
| G01N 33/574 | (2006.01) |

(52) U.S. Cl.
CPC ..... *G01N 33/6812* (2013.01); *A61K 31/7076* (2013.01); *C07H 19/16* (2013.01); *C07K 16/44* (2013.01); *G01N 33/57484* (2013.01); *C07K 2317/20* (2013.01); *C07K 2317/33* (2013.01); *G01N 2440/12* (2013.01); *G01N 2800/105* (2013.01); *G01N 2800/7033* (2013.01); *Y02A 50/423* (2018.01)

(58) Field of Classification Search
CPC ......... G01N 33/6812; G01N 33/57484; G01N 2440/12; G01N 2800/105; G01N 2800/7033; G01N 33/53; A61K 31/7076; C07H 19/16; C07K 16/44; C07K 2317/20; C07K 2317/33; Y02A 50/423
See application file for complete search history.

(56) References Cited

U.S. PATENT DOCUMENTS

| 8,728,732 B2* | 5/2014 | Guerrero-Preston ........................ C12Q 1/6827 435/6.11 |
|---|---|---|
| 9,877,982 B2* | 1/2018 | Hao .................... A61K 31/7076 |
| 2009/0263879 A1* | 10/2009 | Chang .................... C07K 16/44 435/183 |
| 2018/0169128 A1* | 6/2018 | Hao .................... A61K 31/7076 |

OTHER PUBLICATIONS

Yu et al. Progressive disease in chronic lymphocytic leukemia is correlated with the DNA methylation index. Leukemia Research 2007, pp. 773-777. (Year: 2007) (Year: 2007).*

* cited by examiner

*Primary Examiner* — Shafiqul Haq
(74) *Attorney, Agent, or Firm* — Isaac Angres

(57) ABSTRACT

The invention provides a method of detecting the presence, absence or severity of a disease in a patient wherein said disease is accompanied by decreased level of S-adenosylmethionine, or increased level of S-adenosylhomocysterine, or reduced methylation index comprising: identifying any individual or a patient that is suspected of having said disease or is at risk of having said disease; obtaining a biological sample from said patient; determining the level of SAM in said biological sample using an antibody derived from a hapten analog of SAM, SAH; and correlating the levels of SAM, SAH and MI in said biological sample with the presence, absence, or severity of said disease. The invention also provides methods for determining methylation index in biological fluids which is indicative of the health status of an individual. Additionally, the invention includes colloidal gold test strips and homogenous enzyme immunoassays which are useful for determining S-adenosylmethionine and S-adenosylhomocysteine.

8 Claims, 34 Drawing Sheets

B

A

B

A

B

A

B

A

IMMUNOASSAYS OF S-ADENOSYLMETHIONINE AND METHYLATION INDEX IN PERSONALIZED MEDICINE AND HEALTH EVALUATION

This application is a divisional application of U.S. Ser. No. 14/732,775 filed Jun. 7, 2015; which application is a continuation-in-part of U.S. Ser. No. 14/457,099 filed Aug. 11, 2014; which application is a continuation-in-part of U.S. Ser. No. 14/218,928 filed Mar. 18, 2014, the entire contents of which are incorporated by reference herein. This application also claims the priority benefit under 35 U.S.C. section 119 of U.S. Provisional Patent Application No. 61/801,547 entitled "Immunoassay Of S-Adenosylmethionine In Personalized Medicine And Health Or Cancer Evaluation" filed on Mar. 15, 2013, and which is in its entirety herein incorporated by reference.

FIELD OF THE INVENTION

The present invention generally relates to measuring levels of S-adenosylmethionine in biological fluids as a marker of many diseases.

The instant invention also relates to measuring levels of S-adenosylmethionine in biological fluids as a marker of many diseases by using antibodies raised againts analogs thereof.

The present invention relates to measuring levels of S-adenosylmethionine in biological fluids as a marker of disease and correlating the levels to disease progression and determining the proper therapeutic protocol based on the levels of S-adenosylmethionine.

This invention also relates to diagnostic, screening, and early detection methods for cancer, which can also be used to monitor therapeutic effectiveness and relapse monitoring in cancer and other pathological and physiological processes.

The present invention is also directed to a system for developing target specific assays for determining whether a patient will likely respond to a target specific drug, and more particularly to a such a system that is highly economical and provides synergies when diagnostics and drugs are developed in parallel.

The instant invention is also directed to a method for discovering, screening, searching, identifying, developing and/or evaluating the measurement of the methylation index for correlating disease progression and disease treatments and response to said treatments.

The present invention also relates to using the methylation index (or methylation status in some of the literature). In this filing we use methylation index to represent SAM/SAH) as a biomarker, methods, devices, reagent, systems and kits for the detection, diagnosis of cancer as well as other diseases and for the monitoring of cancer progression and for monitoring the progress of various cancer treatments and other diseases. Cancer progression is characterized by progressively increased levels of global DNA hypomethylation, regional CpG hypermethylation, and genomic instability. Decreased methylation index is co-related with the global DNA hypomethylation and genomic instability. Therefore, it is a good marker to help evaluate health status and disease progression or stages.

BACKGROUND OF THE INVENTION

S-Adenosylmethionine (SAMe) is found in almost every tissue and fluid in the body. SAM plays a crucial role in the process called transmethylation. Methylation is involved in nearly every aspect of life. SAM is the primary "methyl" donor for a variety of methyl-transfer reactions in DNA, RNA, proteins, lipids, and small molecules in the body. Proper DNA methylation is essential for normal embryonic development. Methyl-transferase gene homozygously deleted (knocked out) has been proven lethal (Pegg, A. E., Feith, D. J., Fong, L. Y., Coleman, C. S., O'Brian, T. G., and Shantz, L. M., 2003, Biochem. Soc. Trans. 31, 356-360). DNA improperly methylated has been found in many tumors. Alterations in DNA methylation patterns induce the expression of oncogens or silence the expression of tumor suppressor genes, and methyl deficient diets have been shown to promote liver cancer in rodents.

The transsulfuration begins with S-adenosylhomocysteine (SAH), the residual structure of SAM upon donating the methyl group (transmethylation). Hydrolysis of SAH yields homocysteine, which in turns converts to cystathionine, then cysteine, and eventually, to glutathione, the hepatocellular antioxidant and life-saving detoxification agent.

The aminopropylation is another process initiated with SAM through decarboxylation. The decarboxylated SAM then couples with putrescine to generate spermidine and spermine which are critical to cell growth, differentiation and the stability of DNA and RNA. Furthermore, Methylthioadenosine (MTA), the by-product of polyamine synthesis, is a powerful analgesic and anti-inflammatory agent. This may be, at least partially, responsible for the clinical benefits observed in the treatment of osteoarthritis, rheumatoid arthritis and fibromyalgia with SAMe.

SAMe plays a role in the immune system, maintains cell membranes, and helps produce and break down brain chemicals, such as serotonin, melatonin, and dopamine. Deficiency of either vitamin B12 or foliate can reduce the level of SAMe. SAMe is also an antioxidant, a substance that protects the body from damaging reactive oxygen molecules in the body. These reactive oxygen molecules can come from inside the body or from environmental pollution and are thought to play a role in the aging process and the development of degenerative disease. In general, SAMe is thought to raise the level of functioning of other amino acids in the body.

By way of further background, S-adenosyl-1-methionine is a substrate of an enzyme lyase that converts S-adenosyl-1-methionine to the molecule methylthioadenosine and homoserine; it is an aminobutyric chain donor to tRNA; it is an aminoacidic chain donor in the biosynthesis of biotin; SAM-e, after decarboxylation, is the donor of aminopropyl groups for the biosynthesis of neuroregulatory polyamines spermidine and spermine. (Zappia et al (1979), Biomedical and Pharmacologcial roles of Adenosylmethionine and the Central Nervous System, page 1, Pergamon Press. N. Y.)

SAM-e has been used clinically in the treatment of liver disease (Friedel H, Goa, K. L., and Benfield P., (1989), S-Adenosyl-1-methionine: a review of its pharmacological properties and therapeutic potential in liver dysfunction and affective disorders in relation to its physiological role in cell metabolism. Drugs. 38, 389-416), arthritis (Di Padova C, (1987), S-adenosyl-1-methionine in the treatment of osteoarthritis: review of the clinical studies. Am J. Med. 83, (Suppl. 5), 6-65), and depression (Kagan, B, Sultzer D. L., Rosenlicht N and Gerner R. (1990), Oral S-adenosylmethionine in depression: a randomized, double blind, placebo-controlled trial. Am. J. Psychiatry 147, 591-595.) Alzheimer's patients have reduced cerebral spinal fluid levels of S-adenosyl-1-methionine (Bottiglieri et al, (1990), Cerebrospinal fluid S-adenosyl-1-methionine in depression and dementia: effects of treatment with parenteral and oral S-adenosyl-1-methionine. J. Neurol. Neurosurg. Psychiatry 53, 1096-1098.) In a preliminary study, SAM-e was able to produce cognitive improvement in patients with Alzheimer's disease. (Bottiglieri et al (1994), The clinical potential of admetionine (S-adenosyl-1-methioinine) in neurological disorders. Drugs 48, 137-152.) SAM-e brain levels in patients with Alzheimer's disease are also severely decreased. (Morrison et al, (1996), Brain S-adenosylmethionine levels are severely decreased in Alzheimer's disease, Journal of Neurochemistry, 67, 1328-1331.) Patients with Parkinson's disease have also been shown to have significantly decreased blood levels of SAM-e. (Cheng et al, (1997), Levels of L-methionine S-adenosyltransferase activity in erythrocytes and concentrations of S-adenosylmethionine and S-adenosylhomocysteine in whole blood of patients with Parkinson's disease. Experimental Neurology 145, 580-585.)

SAM-e levels in patients treated with the antineoplastic drug methotrexate are reduced. Neurotoxicity associated with this drug may be attenuated by co-administration of SAM-e. (Bottiglieri et al (1994), The Clinical Potential of Ademetionine (S-adenosylmethionine) in neurological disorders, Drugs, 48 (2), 137-152.)

Cerebral spinal fluid levels of SAM-e have been investigated in HIV AIDS dementia Complex/HIV encephalopathy and found to be significantly lower than in non-HIV infected patients. (Keating et al (1991), Evidence of brain methyltransferase inhibition and early brain involvement in HIV positive patients Lancet: 337:935-9.) Additionally, it is also known that *Pneumocystis Carinii pneumonia* (PCP) occurs when the host is immunosuppressed. The *Pneumocystis pneumonia* (PCP) in humans is associated with advanced HIV disease, severe malnourishment in children, and treatments for cancers, advanced cancers, rheumatic disease, and the prevention of organ transplant rejection (Perez-Leal et al. Am J Respir Cell Mol Biol Vol 45, PP1142-1146, 2011). It is fatal if untreated. Therefore early diagnosis is very important. Studies have been done regarding S-adenosylmethionine (SAM) levels in the diagnosis of *Pneumocystis Carinii Pneumonia* (PCP) in patients with HIV Infection. Because S-adenosylmethionine is required by *Pneumocystis carinii* in vitro, *Pneumocystis* infection depletes plasma SAM of rats and humans, nicotine reduces SAM of guinea pig lungs, and smoking correlates with reduced episodes of *Pneumocystis pneumonia* (PCP) in AIDS patients. Chronic nicotine treatment increases lung polyamine catabolic/anabolic cycling and/or excretion leading to increased SAM-consuming polyamine biosynthesis and depletion of lung SAM (J. Biological Chemistry 2005; 280(15):15219-15228). Therefore, severely decreased plasma SAM level predicts occurrence of PCP in patients with immunocompromised conditions only. The best treatment regimens for PCP should include keeping SAM level low as lowered SAM level helps to kill PCP pathogen, whereas, increasing SAM level is recommended for better outcomes of treating other diseases when SAM or MI is low.

De La Cruz et al have shown that SAM-e, chronically administered, can modify the oxidative status in the brain by enhancing anti-oxidative defenses. (De La Cruz et al, (2000), Effects of chronic administration of S-adenosyl-1-methionine on brain oxidative stress in rats. Naunyn-Schmiedeberg's Archives Pharmacol 361: 47-52.) This is similar to results obtained with SAM-e in liver and kidney tissue. Thus SAM-e would be useful as an antioxidant.

Oral SAM-e administration to patients with and without liver disease has resulted in increases in liver glutathione levels. (Vendemiale G et al, (1989), Effect of oral S-adenosyl-1-methionine on hepatic glutathione in patients with liver disease. Scand J Gastroenterol; 24: 407-15. Oral administration of SAM-e to patients suffering from intrahepatic cholestasis had improvements in both the pruritus as well as the biochemical markers of cholestasis. (Giudici et al, The use of admethionine (SAM-e) in the treatment of cholestatic liver disorders. Meta-analysis of clinical trials. In: Mato et al editors. Methionine Metabolism: Molecular Mechanism and Clinical Implications. Madrid: CSIC Press; 1992 pp 67-79.) Oral SAM-e administration to patients suffering from primary fibromyalgia resulted in significant improvement after a short term trial. (Tavoni et al, Evaluation of S-adenosylmethioine in Primary Fibromaylgia. The American Journal of Medicine, Vol 83 (suppl 5A), pp 107-110, 1987.) SAM-e has been used for the treatment of osteoarthritis as well. (Koenig B. A long-term (two years) clinical trial with S-adenosylmethionine for the treatment of osteoarthritis. The American Journal of Medicine, Vol 83 (suppl 5A), Nov. 20, 1987 pp 89-94)

SAM-e is clinically useful in many apparently unrelated areas because of its important function in basic metabolic processes. One of its most striking clinical uses is in the treatment of alcoholic liver cirrhosis that, until now, remained medically untreatable. Mato et al demonstrated the ability of oral SAM-e in alcoholic liver cirrhosis to decrease the overall mortality and/or progression to liver transplant by 29% vs 12% as compared with a placebo treated group. (Mato et al (1999), S-adenosylmethionine in alcohol liver cirrhosis: a randomized, placebo-controlled, double blind, multi-center clinical trial, Journal of Hepatology, 30, 1081-1089.)

In alcoholic liver, SAM is reduced whereas SAH and Hcy levels are increased. Two genes (MAT1A and MAT2A) encode for the essential enzyme methionine adenosyltransferase (MAT), which catalyzes the biosynthesis of S-adenosylmethionine (SAMe), the principal methyl donor and, in the liver, a precursor of glutathione. MAT1A is expressed mostly in the liver, whereas MAT2A is widely distributed. MAT2A is induced in the liver during periods of rapid growth and dedifferentiation. In human hepatocellular carcinoma (HCC) MAT1A is replaced by MAT2A. This is important pathogenetically because MAT2A expression is associated with lower SAMe levels and faster growth, whereas exogenous SAMe treatment inhibits growth (Lu, S C et al. Alcoho 35(3):227-34, 2005).

Sam-e also attenuates the damage caused by tumor necrosis factor alpha and can also decrease the amount of tumor necrosis factor alpha secreted by cells. Consequently, conditions in which this particular inflammatory factor is elevated would benefit from the administration of SAM-e. (Watson W H, Zhao Y, Chawla R K, (1999) Biochem J August 15; 342 (Pt 1):21-5. S-adenosylmethionine attenuates the lipopolysaccharide-induced expression of the gene for tumour necrosis factor alpha.) SAM-e has also been studied for its ability to reduce the toxicity associated with administration of cyclosporine A, a powerful immunosuppressor. (Galan A, et al, Cyclosporine A toxicity and effect of the s-adenosylmethionine, Ars Pharmaceutica, 40:3; 151-163, 1999.)

SAM-e, incubated in vitro with human erythrocytes, penetrates the cell membrane and increases ATP within the cell thus restoring the cell shape. (Friedel et al, S-adenosyl-1-methionine: A review of its pharmacological properties and therapeutic potential in liver dysfunction and affective disorders in relation to its physiological role in cell metabolism, Drugs 38 (3):389-416, 1989)

SAM-e has been studied in patients suffering from migraines and found to be of benefit. (Friedel et al, S-adenosyl-1-methionine: A review of its pharmacological properties and therapeutic potential in liver dysfunction and affective disorders in relation to its physiological role in cell metabolism, Drugs 38 (3): 389-416, 1989)

SAM-e has been administered to patients with peripheral occlusive arterial disease and was shown to reduce blood viscosity, chiefly via its effect on erythrocyte deformability.

SAM-e is commercially available using fermentation technologies that result in SAM-e formulations varying between 60 and 80% purity. (That is, the final product contains 60-80% of the active or (S, S)-SAM-e and 20-40% of the inactive or (R, S)-SAM-e.) (Gross, A., Geresh, S., and Whitesides, Gm (1983) Appl. Biochem. Biotech. 8, 415.) Enzymatic synthetic methodologies have been reported to yield the inactive isomer in concentrations exceeding 60%. (Matos, J R, Rauschel F M, Wong, C H. S-Adenosylmethionine: Studies on Chemical and Enzymatic Synthesis. Biotechnology and Applied Biochemistry 9, 39-52 (1987). Enantiomeric separation technologies have been reported to resolve the pure active enantiomer of SAM-e. (Matos, J R, Rauschel F M, Wong, C H. S-Adenosylmethionine: Studies on Chemical and Enzymatic Synthesis. Biotechnology and Applied Biochemistry 9, 39-52 (1987; Hoffman, Chromatographic Analysis of the Chiral and Covalent Instability of S-adenosyl-1-methionine, Biochemistry 1986, 25 4444-4449: Segal D and Eichler D, The Specificity of Interaction between S-adenosyl-1-methionine and a nucleolar 2-O-methyltransferase, Archives of Biochemistry and Biophysics, Vol. 275, No. 2, December, pp. 334-343, 1989) Newer separation technologies exist to resolve enantiomers on a large commercial production scale at a very economic cost. In addition, it would be conceivable to synthesize the biologically active enantiomer using special sterioselective methodologies but this has not been accomplished to date.

De la Haba first showed that the sulfur is chiral and that only one of the two possible configurations was synthesized and used biologically. (De la Haba et al J. Am. Chem. Soc. 81, 3975-3980, 1959) Methylation of RNA and DNA is essential for normal cellular growth. This methylation is carried out using SAM-e as the sole or major methyl donor with the reaction being carried out by a methyltransferase enzyme. Segal and Eichler showed that the enzyme bound (S, S)-SAM-e 10 fold more tightly than the biologically inactive (R, S)-SAM-e thus demonstrating a novel binding stereospecificity at the sulfur chiral center. Other methyltransferases have been reported to bind (R, S)-SAM-e to the same extent as (S, S)-SAM-e and thus (R, S)-SAM-e could act as a competitive inhibitor of that enzyme. (Segal D and Eichler D, The Specificity of Interaction between S-adenosyl-1-methionine and a nucleolar 2-O-methyltransferase, Archives of Biochemistry and Biophysics, Vol. 275, No. 2, December pp. 334-343, 1989; Borchardt R T and Wu Y S, Potential inhibitors of S-adenosylmethionine-dependent methyltransferases. Role of the Asymmetric Sulfonium Pole in the Enzymatic binding of S-adenosyl-1-methionine, Journal of Medicinal Chemistry, 1976, Vol 19, No. 9, 1099-1103.)

SAM-e (whether in its optically pure enantiomeric form or in an enantiomeric or racemic mixture) presents certain difficult problems in terms of its stability at ambient temperature that result in degradation of the molecule to undesirable degradation products. SAM-e (and thus its enantiomers) must be further stabilized since it exhibits intramolecular instability that causes the destabilization and breakdown of the molecule at both high as well as ambient temperatures. SAM-e has therefore been the subject of many patents directed both towards obtaining new stable salts, and towards the provision of preparation processes that can be implemented on an industrial scale. The present patent thus envisions the use of any of the salts of SAM-e already disclosed in the prior art to stabilize the enantiomeric forms of SAM-e.

The clinical diagnostic field has seen a broad expansion in recent years, both as to the variety of materials of interest that may be readily and accurately determined, as well as the methods for the determination. Over the last several decades, testing for numerous substances such as drugs of abuse, or other biological molecules of interest has become commonplace. In recent years, immunoassay based on the interaction of an antibody with an antigen has been extensively investigated for this purpose. Based on the unique specificity and high affinity of antibodies, an immunoassay can accurately and precisely quantitate substances at the very low concentrations found in biological fluids.

In view of the importance of SAM, it is desirable to have an easy and reliable method to measure its concentration in a biological sample. A classical assay method for measurement of SAM in rat liver utilized the tripolyphosphatase activity that was associated with S-adenosylmethionine synthetase in rat liver. The tripoly-phosphatase activity is stimulated by low concentrations of S-adenosylmethionine. The assay sensitivity was reported at 0.1 nmole of SAM in an assay volume of 0.1 ml (i.e. 10-6M). Samples were lyophilized, homogenized in acid, and centrifuged. The supernatant was then passed through Dowex 1 (HCO3- form) to remove endogenous inorganic phosphate and other potential interferons in the tissue. Great care has to be taken to avoid inorganic phosphate contamination from all reagents including the enzyme preparation, as well as glassware. The disadvantages of this assay are obviously lack of specificity, low sensitivity (1 hard to control and compare between assays in different labs.

Another common method for measuring SAM in tissues or biological fluids is HPLC or electrophoresis after sample preparation normally encompassing the protein precipitation and/or extraction. Post column detection may include derivatization, then measurement through absorption, fluorescence, or electrochemical change, and more recently by Mass Spectrometry (MS), or Tandem Mass Spectrometry (MS/MS) or LC-MS/MS were obtained. Radioisotopes or stable isotopic molecules of SAM are frequently used for internal reference purpose. These methods are capable of measuring low level of SAM in serum or plasma; however, the process typically is laborious, time consuming and/or requires expensive equipment. Another drawback is that it usually does not distinguish the diastereoisomers of SAM at the sulfonium position. SAM is produced biologically in the (S,S) configuration at the sulfonium and a-aminoacid carbon respectively. Under normal physiological conditions or storage conditions, SAM spontaneously racemizes to form a mixture of (R,S) and (S,S) isomers. Most methyltransferases are reported to be specific to the (S,S) form of SAM only.

Another molecule of interest, S-Adenosylhomocysteine (SAH), is the precursor leading to the biosynthesis of SAM, as well as the product of all transmethylation reactions involving SAM as the methyl donor; i.e., SAH is metabolically linked to SAM, and structurally it contains a single carbon (as methyl) less than SAM. The co-existence and structure similarity of SAM and SAH present a great challenge to develop a method for the specific determination of the concentration of either molecule in a biological sample.

The unstable (highly reactive) nature of SAM renders the level of difficulty for its determination even higher.

As the immediate precursor of all of the homocysteine (HCys) produced in the body, SAH has been suggested as a possibly more sensitive indicator for the risk of vascular disease than plasma HCys recently. The total plasma concentration of SAH is normally much lower than HCys. Like SAM, with no distinguished absorption, the determination of SAH in serum or plasma has been a challenge. Advanced method such as LC with post column derivatization, LC-MS/MS with internal reference is a recent development for its determination. However, these methods typically involve expensive instrumentations, laborious sample preparation, and time consuming procedures. Unlike SAM, however, SAH is a relatively stable compound; the sample handling and stability are usually not a problem.

Since SAH is the product of all methylation reactions involving SAM as methyl donor, increased concentration of SAH (or (SAH)) in tissues are frequently accompanied by decreased concentration of SAM ((SAM)). Therefore, the ratio of (SAM) and (SAH) may be a more sensitive indicator than the concentration of either SAM or SAH alone, particularly when their changes are subtle at early stages of dysfunction or abnormal conditions. The ratio of the concentration of SAM to the concentration of SAH known as "the methylation index" was first proposed by Cantani, et al. as an indicator of the methylating capacity of the cell. The ratio was later referred by M. S. Hershfield et al as methylation index (MI).

Therefore, a simple and convenient method that does not require costly instrumentation (LC, MS, and combinations) is clearly desirable for the determination of the biological concentration of SAM and to monitor change and metabolic paths in the body fluids, tissues and organelles. With the monoclonal antibodies against SAM and SAH becoming available as part of the instant invention, immunoassays will be available for research community and clinical labs to quantify SAM, SAH and MI conveniently, easily, accurately and quickly at low cost.

Similarly and in view of the above, there is a need for improved methods for detection and diagnosis of cancer and other diseases, as well as methods for monitoring the progress of the diseases and monitoring the progress of various treatments for cancer and other diseases by quantitating the methylating index as a biomarker.

SUMMARY OF THE INVENTION

Figure 1:
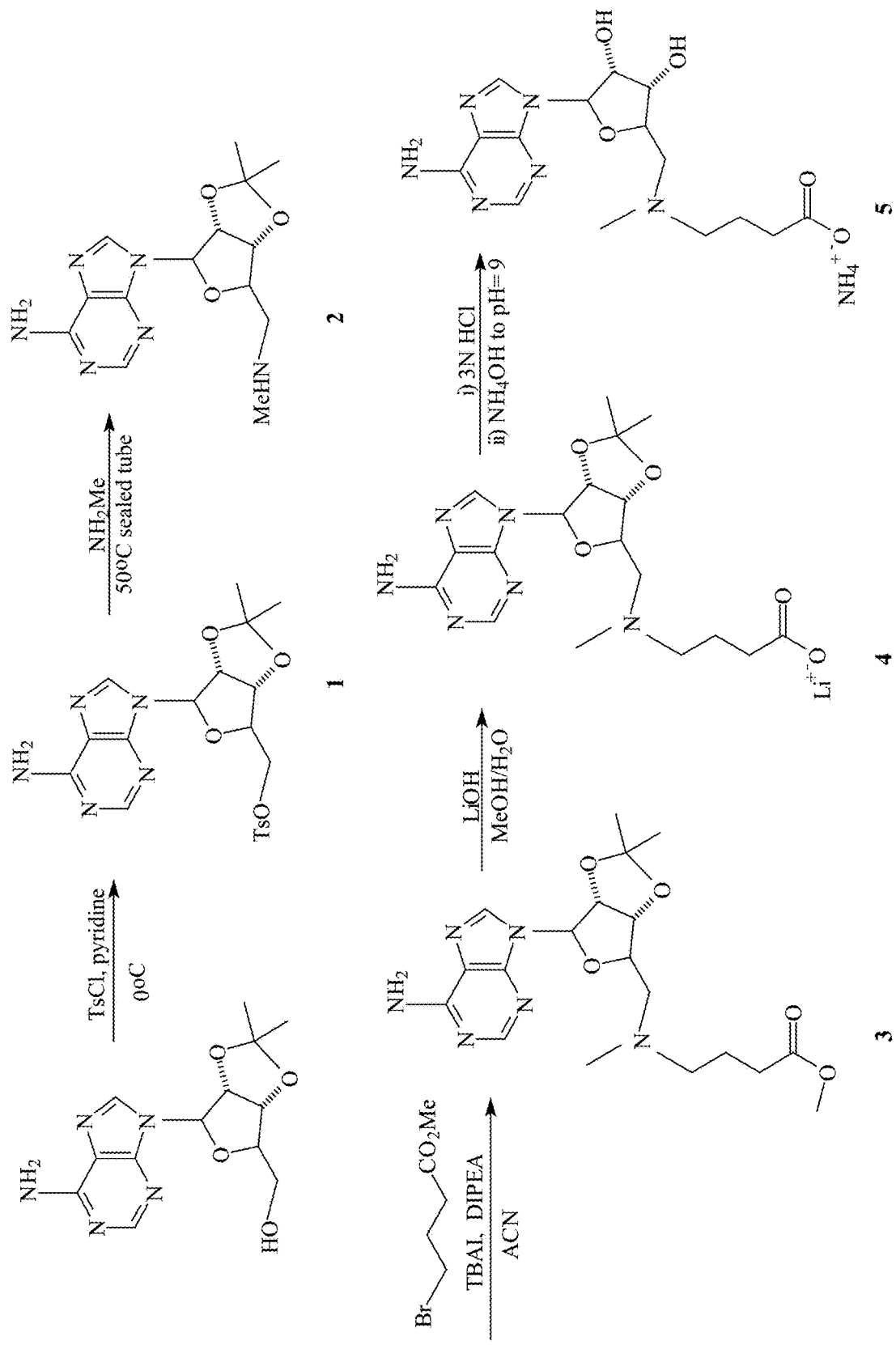
FIG. 1 shows the improved synthetic process of the invention for making hapten.

The instant invention provides a method for providing cancer therapy in a mammal afflicted with cancer which method comprises the following steps: (a) determining the methylation index in a biological fluid sample of said mammal afflicted with cancer; (b) correlating said methylation index to disease progression in said mammal; and (c) based on the results of (b) selecting the appropriate cancer therapeutic protocol to treat said mammal afflicted with cancer.

The methylation index is measured by a method comprising the following steps: (a1) determining the concentration of S-adenosylmethionine in said mammal wherein said method comprises: (i) obtaining a sample; (ii) mixing said sample with antibody specific for S-adenosylmethionine; (iii) detecting the binding of S-adenosylmethionine present in said sample with said antibody; (iv) quantifying the binding as a measure of the amount of S-adenosylmethionine present in said sample; (a2) determining the concentration of S-adenosylhomocysteine according to published literature procedures; and (a3) calculating the ratio of (a1)/(a2) to provide the methylation index of said biological sample.

The invention also provides a method for determining a cancer therapy regimen for treating a tumor in a patient comprising: (a) determining the methylation index in a patient sample; (b) comparing the level of methylation index obtained to a control methylation index to determine whether the level of said index is a predictive marker; and b) determining a cancer therapy regimen for treating the tumor based on the methylation index values, wherein the methylation index values are indicative that the patient is either a responsive patient or a non-responsive patient.

The invention is also directed to a method for treating mood disorders in a human which method comprises: (a) determining the concentration of S-adenosylmethionine in said human wherein said method comprises: (i) obtaining a sample; (ii) mixing said sample with antibody specific for S-adenosylmethionine; (iii) detecting the binding of S-adenosylmethionine present in said sample with said antibody; (iv) quantifying the binding as a measure of the amount of S-adenosylmethionine present in said sample; (b) correlating the levels of SAMe with said mood disorders; and (c) based on the correlation results of (b) administering effective amounts of a drug effective in treating said mood disorders.

The invention further provides a method for diagnosing in a subject, or predicting the susceptibility of a subject to, a mental or neurodegenerative disorder, the method comprising: (a) obtaining one or more biological samples from the subject; (b) determining the levels of S-adenosylmethionine or the methylation index associated with said sample; and (c) comparing the levels of the biomarkers determined in (b) with the levels of said biomarkers from one or more control samples, wherein abnormal levels of the two or more biomarkers in the sample(s) from the subject compared to the one or more control samples is predictive of susceptibility of the subject to a mental or neurodegenerative disorder.

The invention also relates to a method of detecting the presence or absence of a disease in a patient wherein said disease is accompanied by deficient levels of S-adenosylmethionine comprising: identifying a patient that is suspected of having said disease or is at risk of having said disease; obtaining a biological sample from said patient; determining the level of S-adenosylmethionine in said biological sample using an antibody derived from a hapten analog of S-adenosylmethionine; and correlating the level of S-adenosylmethionine in said biological sample with the presence or absence of said disease.

The invention is also directed to a method for assessing the need for treatment of a subject with S-adenosylmethionine alone or in combination with other chemotherapeutic agents comprising the steps of: (a) collecting a sample of body fluid from a subject suspected of needing such treatment; (b) measuring the amount of S-adenosylmethionine levels in said sample; (c) measuring the level of S-adenosylhomocysteine and calculating the methylation index; (d)

comparing the methylation index of said sample with that of a normal standard; and (e) determining if the methylation index lies outside the normal range which is indicative of a need for S-adenosylmethionine treatment.

The invention further provides a method for diagnosing or monitoring a disease or condition comprising the steps of: (a) obtaining a biological sample from a patient to be diagnosed or monitored; (b) determining using an immunoassay the quantity of SAM and SAH in said biological sample; (c) calculating the methylation index of said biological sample; and (d) determining if the quantity(ies) of said SAM, SAH and methylation index in said biological sample is(are) indicative of the presence, absence or status of the disease or condition.

The invention additionally provides a method of assessing one or more health statuses of a subject, the method comprising: determining the methylation index status in a test sample from the subject; said methylation index being calculated by determining the levels of SAM and SAH using any immunoassays; comparing one or more of the determined methylation index states to one or more baseline reference methylation index states; wherein a difference, lack of a difference, or both in one or more of the determined methylation index states and one or more of the baseline reference methylation index states indicates one or more statuses of the subject.

The invention is also directed to a method of use comprising: (a) obtaining at least one sample from a subject; (b) determining the level of SAM, SAH and methylation index as longevity predicting marker(s) in the sample(s); and (c) predicting overall health of a subject based on the marker level.

The invention further provides a method of monitoring an individual's health and relative risk for developing disease(s), comprising the steps of: (a) collecting a sample from the individual; (b) measuring SAM and SAH levels in said sample using an immunoassay; calculating the methylation index; and therefore determining the individual's health.

The invention is also a method of use comprising: (a) treating a subject with a potential therapeutic intervention; (b) determining the effect of the treatment on the levels of SAM, SAH and methylation index as a longevity predicting marker; and (b) using the marker response to predict the effectiveness and prognosis of the intervention.

The invention also relates to a method of use comprising: (a) obtaining at least one sample from a subject; (b) determining the level of SAM, SAH and methylation index as longevity predicting markers in the samples; (c) treating a subject with a potential therapeutic intervention based on the level of longevity predicting markers in the subject; (d) determining the effect of the therapeutic intervention on the level of a longevity predicting marker (only one marker?); and (e) using the marker response to predict the effectiveness and prognosis of the intervention.

The invention additionally provides a method for assessing patient health, the method comprising: providing a sample of bodily fluid from a subject; collecting the SAM and SAH content profile from the bodily fluid; calculating the methylation index based on said SAM and SAH profile, and comparing said methylation index profile to at least one reference methylation index profile to assess the health of the subject, the at least one reference methylation index profile profiling at least one of: one or more disease, cerebrovascular diseases, Parkinson's disease, depression, diabetes, HBP, heart disease, inflammation, kidney disease, liver diseases, pulmonary diseases, lung cancer, liver cancer and other cancers.

The invention further relates to a reference profile for assessing patient health, the profile comprising levels of SAM, SAH and methylation index that are differentially present at a level that is statistically significant, the profile profiling being of at least one of one or more disease, the at least one reference methylation index profile profiling at least one of: one or more disease, cerebrovascular diseases, Parkinson's disease, depression, diabetes, HBP, heart disease, inflammation, kidney disease, liver diseases, pulmonary diseases, lung cancer, liver cancer and other cancers.

The invention also provides a method for assessing the cardiovascular health of a human comprising: (a) obtaining a biological sample from a human; (b) determining the levels of SAM, SAH and methylation index; (c) obtaining a dataset comprised of the levels of each of SAM, SAH and methylation index; (d) inputting the data into an analytical classification process that uses the data to classify the biological sample, wherein the classification is selected from the group consisting of an atherosclerotic cardiovascular disease classification, a healthy classification, a medication exposure classification, a no medication exposure classification; and (e) determining a treatment regimen for the human based on the classification in step (d); wherein the cardiovascular health of the human is assessed.

The invention additionally provides a device for detecting and measuring the presence of SAM, SAH and methylation index in a body fluid wherein the device comprises a single unit for collecting the body fluid, analyzing the contents of the body fluid, and correlating the analysis with physiological status.

The invention is also a method for determining the occurrence of a disease in a subject comprising the steps of: (a) providing a sample previously collected from said subject, (b) measuring at least one biomarker in said sample, wherein the said biomarker is selected from the group of SAM, SAH and methylation index; and (c) determining the occurrence of said disease from the biomarker values measured at step (b).

The invention further provides a method for diagnosing liver disease comprising: contacting an antibody which reacts with S-adenosylmethionine with a test sample to measure an amount of SAM; and relating a measured amount of SAM in the test sample to a diagnosis of whether the test sample is from a person having the liver diseases.

The invention also provides a method for diagnosing liver disease comprising: contacting an antibody which reacts with S-adenosylmethionine with a test sample to measure an amount of SAM; and relating a measured amount of SAM in the test sample to a diagnosis of whether the test sample is from a person having the liver diseases.

The invention further relates to a method for diagnosing a neurological disease comprising: contacting an antibody which reacts with S-adenosylmethionine with a test sample to measure an amount of SAM, measuring an amount of SAM in the test sample; and relating a measured amount of SAM in the test sample to a diagnosis of whether the test sample is from a person having the neurological disease.

The invention is also a method for diagnosing liver disease comprising: determining the methylation index (MI) of said sample and relating said MI in the test sample to a diagnosis of whether the test sample is from a person having the liver disease.

The invention further includes determining the prognosis of acute and chronic liver disease in a subject by correlating the level of SAM in the sample to the prognosis of said acute and chronic liver disease in the subject.

The invention additionally provides a method for diagnosing neurological disease comprising: determining the methylation index (MI) of said sample and relating said MI in the test sample to a diagnosis of whether the test sample is from a person having the neurological disease.

The invention is also a multiplexed assay kit used to monitor liver health in a patient sample, said kit comprising an assay chamber configured to conduct a multiplexed assay measurement for: (a) methylation index level and another biomarker in said sample comprising bilirubin (total or fractionated, conjugated or unconjugated), ammonia, carbohydrate-deficient transferring (CDT), alanine aminotransferase (ALT), alkaline phosphatase (ALP), serum glutamic pyruvic transaminase (SGPT), aspartate aminotransferase (AST), serum glutamic oxaloacetic transaminase (SGOT), albumin, total protein (i.e., plasma proteins), gamma-glutamyl transferase (GGT), gamma-glutamyl transpeptidase (GGTP), lactic acid dehydrogenase (LDH), prothrombin time, or combinations thereof.

The invention also provides a method for monitoring liver health in a patient, said method comprising (a) obtaining a test sample from a patient; (b) measuring the methylation index level in said sample; (c) measuring the level of a biomarker selected from the group consisting of bilirubin (total or fractionated, conjugated or unconjugated), ammonia, carbohydrate-deficient transferring (CDT), alanine aminotransferase (ALT), alkaline phosphatase (ALP), serum glutamic pyruvic transaminase (SGPT), aspartate aminotransferase (AST), serum glutamic oxaloacetic transaminase (SGOT), albumin, total protein (i.e., plasma proteins), gamma-glutamyl transferase (GGT), gamma-glutamyl transpeptidase (GGTP), lactic acid dehydrogenase (LDH), prothrombin time, or combinations thereof; (d) comparing said methylation index level and said biomarkers in step (c) in said sample to a level of said methylation index and said biomarkers of step (c) in a normal control sample; and (e) diagnosing the presence or absence of a liver disorder in said patient based on said comparison.

The invention also provides antibody which has substantially selective reactivity with S-adenosylmethionine and has a cross reactivity of 10% or less with S-Adenosylhomocysteine, 10% or less with Adenosine, and 10% or less with L-Methionine.

The invention also provides antibody which has substantially selective reactivity with S-adenosylmethionine and has a cross reactivity of 5% or less with S-Adenosylhomocysteine, 5% or less with Adenosine, and 5% or less with L-Methionine.

The invention also provides antibody which has substantially selective reactivity with 5-adenosylmethionine and has a cross reactivity of 1% or less with S-Adenosylhomocysteine, 1% or less with Adenosine, and 1% or less with L-Methionine.

The invention also provides antibody which has substantially selective reactivity with S-adenosylmethionine and has a cross reactivity of 10% or less with S-Adenosylhomocysteine, 10% or less with Adenosine, and 10% or less with L-Methionine.

The present invention also provides monoclonal high affinity antibodies immunoreactive with S-adenosyl methionine wherein the binding affinity constant of said antibodies for said S-adenosyl methionines is at least $10^6$ $M^{-1}$.

The invention further provides an antibody which has substantially selective reactivity with S-adenosylmethionine and has a cross reactivity of 10% or less with S-Adenosylhomocysteine, 10% or less with Adenosine and 10% or less with L-Methionine and wherein said antibody has a binding affinity constant for said SAM or an analog thereof of at least $10^6 M^{-1}$.

DETAILED DESCRIPTION OF THE INVENTION

The invention provides assays, diagnostics, therapeutics and medical evaluation of patients with a variety of diseases where it is necessary to asses their state of health. Their state of health can be assessed using assays that provide accurate concentration of S-adenosylmethionine and S-adenosylhomocysteine. Having accurate determination of the above molecules will allow for calculation of the methylation index which is an important parameter related to the state of health of a human being. SAM measurement and methylation index may be an generic marker to evaluate healthy and diseased individuals.

The assay of the invention uses antibodies which are specific to S-adenosylmethionine and analogs thereof and prepared by inoculating a host animal with an immunogen comprising an immunogenic substance directly or indirectly coupled to an S-adenosylmethionine hapten of the formula:

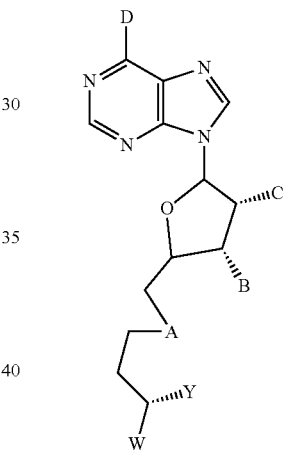

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, and salts thereof; wherein A is selected from the group consisting of

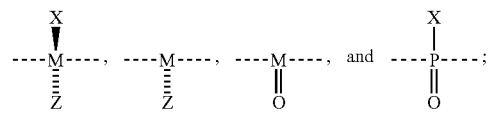

wherein M is selected from the group consisting of N, $N^+$, C, S, $S^+$, Se, $Se^+$, and P; ---- denotes the bonding location for each A group as defined above;

X is independently selected from the group consisting of H, $CH_3$, $CH_2OH$, $CH_2NH_2$, OH, $OCH_3$, $NH_2$, SH, CHO, and CN;

Z is independently selected from the group consisting of $CH_3$, $CH_2OH$, $CH_2NH_2$, OH, $OCH_3$, $NH_2$, SH, CHO, and CN;

B and C are independently selected from the group consisting of H, OH, NH$_2$, SH, F, Cl, Br, and I;

D is independently selected from the group consisting of NH$_2$, OH, SH, F, Cl, Br, and I;

Y is independently selected from the group consisting of H, CH$_3$, CH$_2$OH, CH$_2$NH$_2$, OH, OCH$_3$, NH$_2$, SH, CHO, and CN; and W is independently selected from the group consisting of H, COOH, CONH$_2$, COOCH$_3$, CN, CHO and functionalized derivatives thereof; and thereafter collecting serum from said host animal. The antibodies are described in detail in commonly owned U.S. Pat. No. 8,344,115, the entire contents of which are incorporated by reference as if it was denoted in its entirety.

In another aspect, the invention provides mouse monoclonal and rabbit polyclonal antibodies recombinant, humanized and chimeric antibodies against S-adenosylmethionine and agaisnt S-adenosylhomocysteine using the analogs as described in commonly owned U.S. Pat. No. 8,344,115.

The present invention also provides monoclonal high affinity antibodies immunoreactive with S-adenosyl methionine wherein the binding affinity constant of said antibodies for said S-adenosyl methionines is at least $10^6$ M$^{-1}$ and also further provides an antibody which has substantially selective reactivity with S-adenosylmethionine and has a cross reactivity of 10% or less with S-Adenosylhomocysteine, 10% or less with Adenosine and 10% or less with L-Methionine and wherein said antibody has a binding affinity constant for said SAM or an analog thereof of at least $10^6$M$^{-1}$.

As is well known in the litearture, for the reaction: Ab+Ag=AbAg, the rate of formation of the AbAg complex $r_f = k_{forward}[Ab][Ag]$, and the rate at which it breaks down $r_b = k_{backward}[AbAg]$ wherein [Ag]=Concentration of antigen; [Ab]=concentration of antibody; [AgAb]=concentration of AgAb complex. The rate constants $k_{forward}$ and $k_{backward}$ depends on temperature, pH and other conditions. Therefore, at equilibrium, $r_f = r_b$.

The equilibrium or affinity constant Ka or K is defined from the equation:

$$K = \frac{k_{forward}}{k_{backward}} = \frac{[AbAg]}{[Ab][Ag]}$$

Antibody-antigen interactions are in fact more complicated as both the antibody and antigen may have multiple binding sites. Avidity or functional affinity describes the extra tightness achieved by binding though multiple sites, which can be considerably greater than the single-site affinity. In practice, when we measure the binding of an antibody to an antigen, it is an average functional affinity which is measured and we do not worry about the exact number of binding sites. This functional affinity constant has an important bearing on the appropriate concentration of antibody needed for a particular application e.g. diagnostic assay or therapy.

Through the use of monoclonal hybridomally produced antibodies, the present inventors have now simultaneously improved the specificity and the affinity of immunoassays, in all reactions between antiSAM antibodies and SAM. By increasing the affinity binding constant to the high values observed in the present invention, it is possible for the first time to carry out highly sensitive immunoassay procedures using the antibodies of the invention. The combined use of a hybridomally produced antibody and using a SAM analog allows the improvement in performance.

The specificity relates to the lack of cross reactivity or lack of interference in the SAM-antibody reaction by other substances present in the reaction mixture. Hybridomally produced antibodies in general, exhibit an extraordinary specificity since they are directed against a single determinant. However because they are directed against a single determinant, they bind to fewer sites than classically (polyclonally) produced antibodies. This fact had been reflected in an existing fear in the prior art that the extraordinary specificity of monoclonally produced antibodies, would be a detriment to their utilization in sensitive clinically useful immunoassays. The present inventors however have now demonstrated that hybridomally produced antibodies can detect less SAM than the conventionally produced antibodies, despite their extraordinary specificity.

The antibodies of the invention have an affinity constant for said S-adenosyl methionines of at least $10^6$M$^{-1}$ and more preferably in the range of $10^6$M$^{-1}$-$10^{11}$M$^{-1}$.

The invention also provides immunoassays using monoclonal Anti-SAM and SAH antibodies to determine methylation index and the level of SAM in directing and developing SAM treatment regimen and general health evaluation, etc.

The invention further relates to using the methylation index as measured in the present invention as a screen marker in the general state of health of a given subject or population at large.

The antibodies of the invention are also useful in performing immunohistochemical analysis ans flow cytometry analysis.

The instant invention further provides rapid, reliable and inexpensive immunoassays to measure SAM and SAH levels in saliva, urine, serum, plasma and whole blood semi-quantitatively using rapid test strip devices. In an embodiment of the invention, a membrane is pre-soaked with anti-SAM (or anti-SAH) antibody-dye (colloidal gold) conjugate. Secondary antibody is immobilized in the Control zone. Anti-SAM (or anti-SAH) antibody is immobilized in Test zone. Specimen migrates along the membrane. If SAM (or SAH) is present, antigen-antibody complex is formed and will be captured by antibodies in both Test and Control zones, thus pink color is seen in both zones. If SAM (or SAH) is absent, antibody-dye conjugate is only captured by secondary antibody in the Control zone, thus pink band is seen only in control zone, which indicate test has worked correctly and the results from the test lines should be considered valid. Run standards and samples at the same time and compare the signal (color and width of the positive band) strength of test zones to those of standards to roughly determine the concentration of SAM (or SAH), a way to semi-quantify SAM (or SAH).

In a competitive immunoassay similarly as above, Test zone is immobilized with SAM (or SAH). The SAM (or SAH) from specimen competes with the SAM (or SAH) immobilized on Test zone to the limited amount of the antibody-dye conjugates. The more SAM (or SAH) there is from specimen, the less pink line will be seen from Test zone. Extremely low SAM (or SAH) or no SAM (or SAH) from specimen generates two strong lines in both Test and Control zones.

The semi-quantitative assay is ideal for consumers or patients to use before taking SAM-e as treatment for diseases, in the middle of SAM-e treatment, or to determine whether they should stop using SAM-e or not.

The invention also provides a method of personalized medicine for mammal diseases, the method comprising measuring the methylation index in body fluids from a subject having a disease, and proposing a treatment with a likelihood of being effective for said subject based on the methylation index levels in said body fluids.

The invention is also a method for monitoring the efficacy of a cancer treatment in a patient diagnosed with cancer comprising determining the methylation index level in the patient at a first point in time; treating the patient with a cancer treatment; determining the methylation index level in the patient at a second point in time; and comparing the level(s) of the methylation index in the subject at the first point in time with the levels at the second point in time to determine the efficacy of the cancer treatment.

In another aspect the invention provides a method for providing cancer therapy in a mammal afflicted with cancer which method comprises the following steps: (a) determining the methylation index in a biological fluid sample of said mammal afflicted with cancer; (b) correlating said methylation index to disease progression in said mammal; and (c) based on the results of (b) selecting the appropriate cancer therapeutic protocol to treat said mammal afflicted with cancer. The method includes collecting blood samples from patients having stage I, or stage II, or stage III, or stage IV cancer and determining the levels of SAM and SAH, then calculating the methylation index, correlating the methylation index with the cancer stage and then selecting an appropriate therapeutic protocol for treating said mammal.

The invention is also useful in determining how well and effective DNA methyltransferase inhibitors are in treating cancer. The methylation index is the best tool or means to help evaluate how, the extent and specificity of a certain DNA Methyltransferase (DNMT) inhibitors' functions in particular organs or tissues. Accordingly, the measurement of the methylation index can be used in assessing the effectiveness of DNA methyl transferase inhibitors by using the measurements developed as a result of the present invention.

The invention is further directed to a method for predicting prognosis of a patient having a given disease, comprising: obtaining a tissue sample or a biological fluid sample from the patient; and measuring the levels of SAM and SAH and calculating the MI in the sample, wherein the measured levels, or a as compared to a reference levels, is indicative of the prognosis of the disease is said patient.

The invention also provides an in vitro method for determining disease prognosis for a patient suffering from a given disease, said method comprising: (a) providing or obtaining a biological sample said patient; (b) measuring the amounts of SAM and SAH and calculating the MI of said biological sample; and (c) optionally deducing from the result of step (b) the prognosis of said patient.

The invention also provides a method of determining a subject's likelihood of longevity which comprises comparing SAM levels from the subject's plasma with the SAM levels from a control population, a high value of the subject's SAM level compared to the control population indicating that the subject has an increased likelihood of longevity.

The instant invention also provides a method for determining whether an immunocompromised patient is susceptible to *Pneumocystis Carinii* pneumonia (PCP) infection which method comprises: (a) obtaining a biological sample from a patient; (b) determining using an immunoassay the quantity of SAM in said biological sample; (c) comparing the quantity of SAM in said biological sample to the patient's baseline reference; and (d) determining if the quantity of said SAM in said biological sample is indicative of the presence, absence or status of the PCP infection.

The invention further provides:

1. Directed Therapies with SAMe

Both the effective studies on SAMe in treating mild to moderate depression, osteoarthritis (better than nonsteroidal anti-inflammatory drugs), fibromyalgia, and not so beneficial studies on SAMe have been reported. The most possible reason for this is similar to most other diseases and treatments, i.e. certain patients are not good candidates to use SAMe while some other patients are good candidates. To find out beforehand whether patients are good candidates for using certain medicine or not, some measurement has to be performed. Applicants' have discovered that it is desirable to determinine the level of SAM in blood or urine samples before using SAMe for treatment of diseases.

Auxiliary treatment with SAMe in a variety of diseases, e.g. liver disorders, B12 or foliate deficiencies, cancers, Parkinson's patients who take Levodopa (L-dopa) has been accepted because these diseases can cause reduction of SAM level in the body. To be sure whether SAM level is actually reduced, the best way is to directly measure the level of SAM in blood plasma. There exist other situations when SAM level can be brought down due to therapies and diseases themselves. Therefore, monitoring SAM level is very important in improving overall efficacies of therapies whether the therapies include SAMe or not. For situations when SAM level is below certain acceptable level in the middle of other treatment regimen for depression, osteoarthritis, fibromyalgia, Parkinson's, Alzheimer's disease, dementia, liver disorders, bursitis, tendonitis, chronic low back pain, multiple sclerosis, spinal cord injuries, migraine headaches, lead poisoning, and to slow aging etc., supplementing appropriate dosages of SAMe will benefit overall treatment. For cases when treatment has not started, if SAM deficiency is detected, administering SAMe via IV for the diseases above would quickly relieve the symptoms.

On the other hand, as the information on drug or food interactions with SAMe is very limited, plus the fact that SAMe is not without risk of more significant psychiatric and cardiovascular adverse effects, consumers should be instructed to avoid unmonitored consumption of this dietary supplement until sufficient discussion has taken place with their primary healthcare provider (Fetrow, C. W. et al. "Efficacy of the dietary supplement S-adenosyl-L-methionine." Annals of Pharmacotherapy 35 no. 11 (November 2001): 1414-1425). Taking SAMe with prescription antidepressants can cause serotonin syndrome that can be quite dangerous. Immunoassay of SAM as describe in the U.S. Pat. No. 8,344,115 is the best way to allow clinical labs and patients themselves to quickly find out the level of SAM. The immunoassays described in the patent are sensitive, easy, quick, without using costly equipment. The results are comparable between assays. Furthermore, normal SAM concentration in plasma appears to be different, greatly depending on gender (normally, men>women), individual's weight, and maybe ethnicity, and diet, health condition, whether taking medicines or not, etc. Therefore, monitoring SAM level is critical in personalized and directed administration of SAMe to achieve the best result in treatment.

2. Methylation Index in Disease Development and Prognosis

The methylation index is defined as a ratio of concentration of SAM to concentration of SAH. It is important and more accurate to use methylation index instead of the level of SAM itself under certain circumstances. The reasons include (1) SAH+ is the direct end product of SAM methylation reaction after methyltransferase (COMT). The SAHH is reversible enzyme whereas other enzymes are unidirectronal, the equilibrium dynamics of the SAHH reaction strongly favor SAH synthesis over homocystein synthesis (SJ James, et al. Elevation of S-Adenosylhomocysteine and DNA Hypomethylation: Potential Epigenetic Mechanism for Homecysteine-Related Pathology. J. Nutri. 132:2361S-2366S, 2002). The accumulation of SAH inhibits activities of methytransferases, thus, reduces the level of SAM. The moment SAM as the sole donor of methyl group in cells provides methyl group to DAN, RNA, Protein, phospholipids, neurotransmitters, peptides, hormones, etc., SAH is produced. Therefore, the SAM/SAH is more sensitive and accurate in reflecting methylation reactions and an immediate and accurate indicator of methylation status/level of the important molecules in living organs especially when SAM fluctuation is subtle. (2) The level of SAM varies according to race, gender, body weight and diet, etc. Methylation index can reduce the variations caused by these and other factors.

Cancer is considered as both having genetics causes as well as epigenetic diseases. DNA methylation is one of the most important epigenetic modifications. More and more findings are being revealed on the importance of the once-neglected epigenetic influences on many life phenomena, which says the impact of methylation on cancers could be more and significant and in depth than what we know today. The level of DNA methylation in cancer cells varies in different stages of cancer development. Abnormal DNA methylation occurs commonly in cancers in a special format of genome-wide hypo-methylation and regional hyper-methylation. Global DNA hypo-methylation is associated with activation of proto-oncogenes, such as c-JUN, c-MYC, and c-Ha-Ras, and generation of genomic instability. Hyper-methylation on CpG islands located in the promoter regions of tumor suppressor genes results in transcriptional silencing and genomic instability. CpG hyper-methylation acts as an alternative and/or complementary mechanism to gene mutations causing gene inactivation, and it is now recognized as an important mechanism in carcinogenesis. The inactivation of tumor-suppressor genes (e.g. p53 gene) by CpG-island hyper-methylation of the CpG islands located in their promoter regions is related to the cancer progression and poor prognosis. Research results assign both therapeutic and chemo-preventive significance to methylation patterns in human Hepatocellular Carcinoma (HCC) and open the possibility of using molecular targets, including those identified in this study, to effectively inhibit HCC development and progression (Diego F. Calvisi et l. "Mechanistic and Prognostic Significance of Aberrant Methylation in the Molecular Pathogenesis of Human Hepatocellular Carcinoma." J Clin Invest. 2007; 117(9):2713-2722.).

Drugs that are meant to reduce the level of methylation of DNAs—demethylating agents, the promising chemotherapeutics drugs have been used and more are being studies to treat cancers (Esteller M. "DNA methylation and cancer therapy: new developments and expectations." Curr Opin Oncol. 2005 January; 17(1):55-60. 2005 January; 17(1):55-60.).

In the context of the present invention, "cancer" or "tumor" is intended to include any neoplastic growth in a patient, including an inititial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver. As used herein, cancer cells, including tumor cells, refer to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large Bcell lymphoma, malignant lymphoma, plasmocytoma, reticulum cell sarcoma, or Hodgkins disease); and tumors of the nervous system including glioma, meningoma, medulloblastoma, schwannoma or epidymoma.

3. Methylation Index in Embryo Development and Overall Human Health

The levels of SAM and SAH may be involved in the control of somatic embryogenesis by affecting the level of DNA methylation, which in turn might cause differential changes in gene activation. An increase in the level of SAM may be a prerequisite for progression of embryogenesis and the development of complete embryos (Munksgaard D, et al. "Somatic embryo development in carrot is associated with an increase in levels of S-adenosylmethionine, S-adenosylhomocysteine and DNA methylation." Physiologia Plantarum, Volume 93, Issue 1, Article first published online: 9 Oct. 2008).

Methylation Index in General Human Health Evaluation and Screening

The levels of SAM and SAH may be involved in the control of somatic embryogenesis by affecting the level of DNA methylation, which in turn might cause differential changes in gene activation. An increase in the level of SAM may be a prerequisite for progression of embryogenesis and the development of complete embryos (Munksgaard D, et al. "Somatic embryo development in carrot is associated with an increase in levels of S-adenosylmethionine, S-adenosylhomocysteine and DNA methylation." Physiologia Plantarum, Volume 93, Issue 1, Article first published online: 9 Oct. 2008).

Methyltransferase (MT) plays an important role in human disease development. The Dopamine (DA) Hypothesis associated with the cause of Schizophrenia describes an overactive DA pathway in Schizophrenia patients. Catechol-O-methyltransferase (COMT) degrades DA in central nervous system. Inhibitors of COMT lay the foundation for treatment of Schizophrenia (Renson J et al "Action of the inhibitors of catechol ortho-methyl transferase on the adrenal catecholamines in the rat." Arch Int Physiol Biochim. 1960

May; 68:534-7.). There are over 30 different kinds of MT that work on various substances critical to the functions of human being.

Methylation index is considered as an important indicator/marker for human general health, "vitality" indicators or "wellness" markers.

Furthermore, normal SAM concentration in plasma appears to be different greatly depending on gender (normally, men>women), individual's weight, and maybe ethnicity/race, and diet, etc. Similarly dependency exists for SAH concentrations since SAM and SAH are closely tied together metabolically. By utilizing the ratio of [SAM] and [SAH] it is likely these variables can be eliminated or diminished.

Connection of SAM and SAH to cardiovascular disease, depression, cancer and aging-related diseases such as Alzheimer's disease is well documented. Methylation is highly critical in fetus development, in differentiation, in epigenetic regulation of protein expression mainly via DNA, RNA and the histone methylation. The valuation of the S-adenosylmethionine and methylation capacity index is in their scientific basis as "vitality" indicators or "wellness" markers.

In the present invention, non-invasive sample collection included urine and saliva sample collection. Measuring SAM and SAH levels from normal subject were carried out with saliva sample as well. Oral micro biome is a complex ecological system where about 700 species of micr-oorganisms that have been identified (Palmer Jr., et al. Community Development in Bacterial Biofilms of the Oral Cavity. Microscopy and Microanalysis, 2008). Some of the predominant groups present in the mouth include *Streptococcus*, Neisseriaand and other obligate anaerobes (Avila, M., et al. The Oral Microbiota: Living with a Permanent Guest. DNA & Cell Biology, 2009). Oral organisms keep a mutual relationship with the host by preventing pathogenic species from adhering to the mucosal surface. Some oral microflorae can cause dental plaques and are also a common cause dental caries and periodontal disease. Oral disease in an individual can be caused due to a combination of lack of oral hygiene and factors influencing the oral microbial community structure, such as diet (Gibbons, R. J. et al. Bacterial Adherence in Oral Microbial Ecology. Annual Review of Microbiology, 1975; Marsh, P. D. Role of the Oral Microflora in Health Microbial Ecology in Health and Disease, 2000). An understanding of the oral environment and microbial interactions leads to understanding the main causes for oral diseases. Genetic factors determine metabolic profiles of each individual. It is anticipated that broad ranges or big standard deviations among samples exist for many metabolites. The Examples 23-27 below indicated that both saliva and plasma samples have a relatively broad range of values. The best practice is to keep some factors such as diet, whether or not taking certain medicines much similar between tests of SAM and SAH and collect these samples at a fixed time of a day.

In the normal course of a physical examination, people have blood tests without prior knowledge of diseases. They think they are disease free or not sure whether they have any diseases or not. The MI indicator would give them some idea of whether something has gone wrong or not within themselves, but not confirming what could be wrong. The lower the MI is from the individual's baseline reference MI, the stronger it is to recommend further testing or visiting doctors. It is proposed for the purpose of health screening or disease prevention efforts.

The invention is of particular importance as it provides:
1. Direct, accurate and quantitative measurement of methylation index with all types of bio-samples.
2. Direct, accurate and quantitative measurement of methylation index in all types of lab settings.
3. Direct, accurate and quantitative measurement of methylation index in relating to the evaluation of overall health conditions; cancer prediction and prognosis; treatment (with or without SAMe) evaluation of all diseases.
4. Direct, accurate and quantitative measurement of methylation index in relating to differential diagnosis of cancers.
5. Direct, accurate and quantitative measurement of methylation index in relating to chemotherapy resistance in cancer patients.
6. Direct, accurate and quantitative measurement of methylation index in relating to the evaluation of fetal development, differentiation and aging processes.
7. Semis-quantitative and qualitative immunoassay of methylation index with stripes or other media for use conveniently and easily by consumers in relating to reasons described in 1-6 above.
8. Semis-quantitative and qualitative immunoassay of SAM with stripes or other media for use conveniently and easily by consumers who take over-the-counter or prescribed SAMe for various situations and diseases.
9. Semis-quantitative and qualitative immunoassay of SAM with stripes or other media for use conveniently and easily by consumers with urine and blood samples.
10. Quantitative assay of SAM in relating to the directed medication of SAM-e for various reasons or purposes.
11. Direct, accurate and quantitative measurement of methylation index with all types of bio-samples in relating to general health evaluation.
12. Direct, accurate and quantitative measurement of methylation index with all types of bio-samples in all types of lab settings.
13. Direct, accurate and quantitative measurement of SAM level with all types of bio-samples in assisting in determining or adjusting SAMe treatment schemes.

As shown in Examples 23 and 24 of the present invention, there are significant differences in SAM content, SAH content and MI between healthy people and people with disease, and accordingly the immunoassays of the invention have substantial value in the clinical evaluation and health status of people. More in particular as shown in Table 16 of Example 24, the summary shows the ranges and average of MI for the identified cases. It is consistent with the t-test results that normal people has significantly higher MI (averagely 2.2) than diseased patients (average <1.56). The obvious difference between normal and diseased group can also been seen from the maximum MI.

In the cases of cancers, we can see some samples had MI values fell between 4 and 6, therefore the average MI in cancer groups were relatively higher than other diseased groups. The relatively higher MI in cancer samples is due to relatively higher SAM. This is consistent with a report by Alissa K. et al (Chest. 2007. 132(4): 1247-1252.) in which serum SAM levels were elevated in patients with lung cancer as compared to smokers with benign lung disorders and healthy nonsmokers. There were no significant correlations between SAM levels and tumor cell types, nodule size, or other demographic variables. The temporarily high SAM levels may be caused by release of intracellular SAM from cells into blood stream (as can be confirmed by IHC staining of SAM from cancer cells) at some stage of cancer progression. Therefore, in our cancer samples, we could see wide ranges of MI values observed in all types of cancers. As only certain stage of cancer development that SAM release is significant, once release is completed, SAM level in blood stream won't maintain at the high level, which contributes to the big ranges of SAM levels observed for all cancer types.

In the case of 68 cases of cerebrovascular diseases, there is only one sample has MI as 5.67. All others were less than 2.09. If we consider that sample as an outlier, therefore remove it, the average MI for that group would be less than 1. Therefore, cerebrovascular diseases would be among other diseases in evaluating the range and average value of MI.

The invention also provides therapy with SAM-e and combination of SAM-e with multiple therapeutic drugs. The invention is intended to include compositions containing SAM-e and other therapeutic methods.

The present invention also provides an improved synthetic method for making the Azaadenosyl(deamino)methionine hapten which is used to make antibodies against SAM. The synthetic method is outlined in scheme 1 below and in FIG. 1.

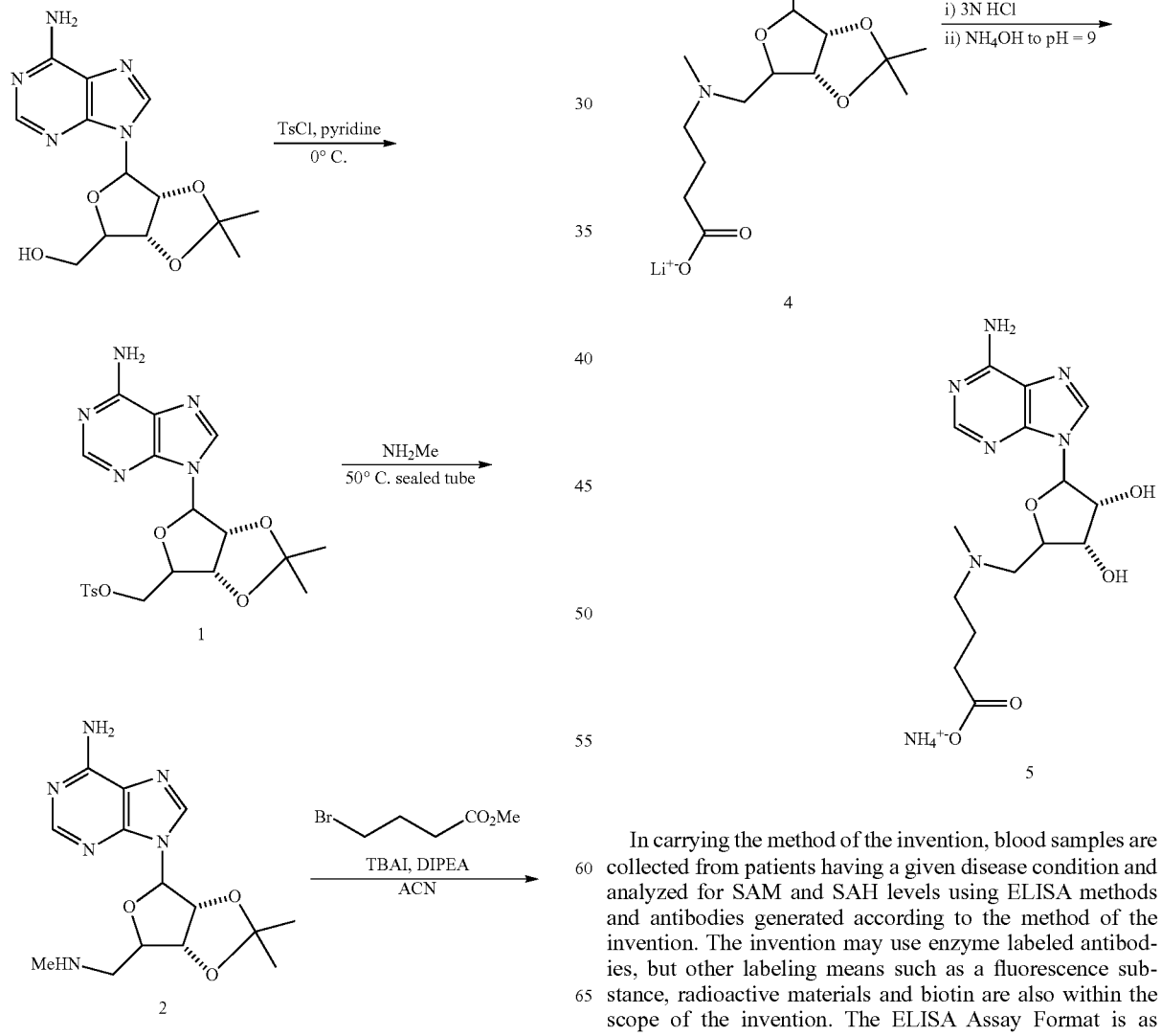

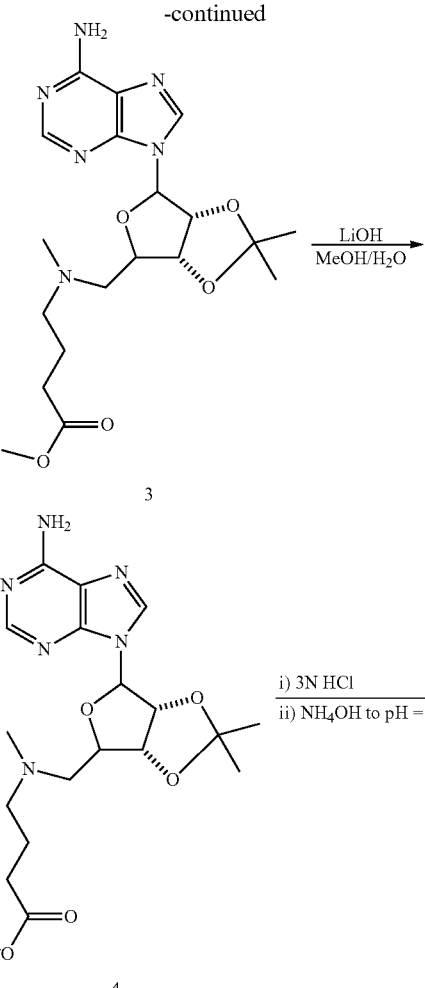

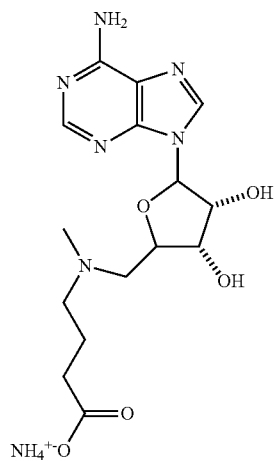

In carrying the method of the invention, blood samples are collected from patients having a given disease condition and analyzed for SAM and SAH levels using ELISA methods and antibodies generated according to the method of the invention. The invention may use enzyme labeled antibodies, but other labeling means such as a fluorescence substance, radioactive materials and biotin are also within the scope of the invention. The ELISA Assay Format is as follows:

Format 1:

Sample or calibrator(s), (2) Antibody, (3) Hapten-Enzyme Conjugate, (4) Secondary antibody coated strips/microtiter plates, (Examples of secondary antibody: goat-anti-mouse antibody or goat-anti-rabbit antibody) (5) Wash solution, (6) Substrate(s). (7) Stopping reagent (optional if "end point" mode is used; for "rate" mode there is no need of a stopping reagent.)

Format 2:

(1) Sample or calibrator(s), (2) Antibody, (3) Secondary antibody-Enzyme Conjugate, (4) Immunogen (Hapten-carrier protein) coated strips/microtiter plates, (5) Wash solution, (6) Substrates and, (7) Stopping reagent (optional if end point mode is used; for "rate" mode there is no need of a stopping reagent.

Format 3:

(1) Two paired antibodies against two different epitopes of a molecule, (2) Sample or calibrator(s), (3) One antibody in (1) is conjugated with enzymes. (4) Wash solution, (5) Substrate(s). (6) Stopping reagent (optional if "end point" mode is used; for "rate" mode there is no need of a stopping reagent.)

The present invention also provides test kits which are based on an immunoassay (e.g., the ELISA test) for the immunological detection of SAM which contain in addition to antibody against S-adenosylmethionine. The ELISA test kits can be in the any of the ELISA formats above. For example, the following components: (a) secondary Ab attached to solid phase; (b) immobilized hapten, hapten derivatiave, immunogen or alike; (c) enzyme substrate(s) in solid or dissolved form; (d) labeled hapten or derivatives (tracer or enzyme conjugates); (e) buffering and washing solutions; (f) additives to prevent, for example, nonspecific adsorption and aggregation; and (g) pipettes, incubation vessels, reference standards, calibration curves, and color tables.

Once the levels of SAM and SAH are determined, the methylation indeces are calculated and used to determine the state of health of the individual.

Generally speaking the average levels of SAM in healthy individuals was about 147±16 nM, the SAH level was 29±11 nM based on measurements from 11 healthy individuals. The methylation index was 5±1. The normal methylation index is above 4.

The average level of SAM for cancer patients was 103±52 nM.

The average level of SAM was 113±15 nM on patients with atherosclerosis. Preliminary results from SAH quantitative ELISA using rabbit monoclonal antibody against SAH showed substantially higher levels for SAH therefore, the SAM/SAH is reduced significantly in patients with Artherosclerosis.

The average level of SAM in plasma is 45±8 nM (from 26 samples) for patients with liver disorders and therefore much lower than that of normal people.

The ratio of SAM and SAH level is calculated and called methylation index, which is a more accurate and convincing measure to evaluate general health, disease status, development and prognostics than a single value of either SAM or SAH. Normally the methylation index is >4. In some pathological situations, it is less than 4 or even less than 1 due to decreased SAM level and increased SAH level. The reduced methylation index in turn will affect the methylation processes of many important molecules such as DNA, RNA, peptides, hormone, neurotransmitters, etc.

The methylation index is used to determine a chemotherapeutic protocol. Cancer patients with significantly reduced methylation index levels are treated with more aggressive protocols. The methylation index is correlated with the stage of the cancer to select an appropriate therapy for each patient.

In another aspect of the invention, We are able to produce a sensitivity detecting cutoff for SAM around 50 nM with the test strip method. The cutoff value for SAH strip is around 200-500 nM. The sensitivity itself is not essential compared to clinically meaningful cutoff values for particular clinical purposes, yet having the ability to obtain higher sensitivity is always good and have other uses.

Rapid test strips are made in the form of cassette and stick for testing SAM and SAH simultaneously or individually. When the product is made with SAM strip alone, it is used for quickly testing SAM level in blood and urine to be used as a way to direct SAM treatment, assist in disease diagnostics and prognostics, and very likely act as a general health indicator. When the product is made with SAH strip alone, it is used in evaluating status of diseases when hyperhomocysteinemia or hyper-S-adenosylhomocysteinemia is considered as a concern or is suspected of. When assembling both SAM and SAH strips in one unit, methylation index strip is made. When the cutoff of methylation index is established, qualitatively measuring the methylation index is an accurate and better way of interpreting perturbation and problems of methionine cycle in human body and other organisms.

EXAMPLES

The following examples are intended to demonstrate the usefulness of the methods and therapeutic compositions of the present invention and should not be construed to limit the scope of the invention in anyway. In the present specification the term biological sample is intended to include saliva, urine, blood, serum, plasma, brain fluids, cerebrospinal fluids, tissue samples and cells or anything derived from the body of a mammal including a human.

Example 1

Generation of Monoclonal and Polyclonal Antibodies Against SAM and SAH

Reagents:
AdaM: Azaadenosyl(deamino)methionine
ASAM: Aza-SAM, or Nitrogen (N)-adenosylmethionine
BgG: Bovine gamma globulinBSA: Bovine serum albumin
BTG: Bovine thyroglublulinC SAM: Carbon (C)-adenosylmethionine or 6(s)-Methyl-6-deaminosinefungindaH: Deamino-5-adenosylhomocysteinedaHSO: daH sulfoxide
DCC: N,N'-dicyclohexylcarbodiimide
DMF: Dimethylformamide
EDAC: 1-Ethyl 3-(3-Dimethylaminopropyl)carbodiimide
ELISA: enzyme-linked immunosorbant assay GAM plate/strip: goat-anti-mouse IgG coated microplate or stripGAR plate/strip: goat-anti-rabbit IgG coated microplate or stripHRP: horse radish peroxidaseIB: Incubation buffer-
KLH: Keho lympet hemocyanine
NHS: N-Hydroxysuccinamide
PBS: phosphate-buffered saline
RT: retention time (for HPLC) or room temperature
SAH: S-Adenosylhomocysteine
SAM: S-Adenosylmethionine
KLH: Keyhole Limpet Hemocyanin
EDC: 1-Ethyl-3-(3-Dimethylaminopropyl) Carbodiimide
BSA: Bovine Serum Albumin PLL: Poly-lysine
HRP: Horse Radish Peroxidase 1. Preparation of AdaM-NHS: To a flask containing overnight vacuum-died AdaM (15.1 mg, ca. 0.041 mmole) was added 21.7 mg (0.107 mmole) of DCC and 7.2 mg (0.061 mmole) NHS. The solid mass was left on vacuum line for 3-4 hr drying. Approximately 1.5 mL dry DMF was then added to the flask under nitrogen atmosphere, and then seal the flask. The solution was stirred at RT overnight. TLC (10% MeOH in CH2Cl2) analysis indicated the formation of the NHS ester.

2. Preparation of AdaM-BSA: Weighed out 59.8 mg BSA to a round bottomed flask and added 5 ml freshly prepared 100 mM sodium phosphate solution, pH 8.25. Place the BSA solution in a 4° C. water bath with vigorous stirring. The AdaM-NHS prepared as described above was then slowly added in 10 µl aliquot every few minutes. After a total of 150 µl was added, the conjugation mixture became turning cloudy. One milliliter of DMSO solution was added to aid dissolution. Upon addition of another 50 µl AdaM-NHS in DMF, the mixture turned cloudy again. Water bath sonication was then applied for 5 minutes after every 10 µl×5 of AdaM-NHS was added. At the conclusion of 150 µl in total of AdaM-NHS in DMF was added, the mixture was sonicated for 20 minutes. To insure the conjugate was free from any hapten, the pool was dialysis against PBS (1.5 liter×4) over 2 days. The final volume of the conjugate is approximately 36 ml, at estimated 1.66 mg/ml BSA.

3. Preparation of AdaM-KLH: Using the method above, weighed out 17.5 mg KLH, AdaM 15.1 mg. The final volume after dialysis is 29.5 ml with concentration of 0.6 mg/ml.

4. Preparation of AdaM-PLL: AdaM 4.72 mg was dissolved in 1 ml DMF, EDC.HCl 6.5 mg and NHS 4.0 mg were added, then the mixture was well-sealed, stirred at room temperature in dark overnight. Weighed out 1.5 mg PLL dissolved with 1 ml 1.0 mM PBS pH 8.2. The activated AdaM was then added slowly to the PLL solution and the mixture was left overnight in dark. Dialyzed the reaction mixture for 48 hours with 10 mM PBS pH 7.3. The final volume after dialysis is 3.5 ml with concentration of 1.4 mg/ml.

5. Preparation of SAH-BSA: SAH (Sigma) 3.8 mg, was dissolved in 1.5 ml PBS, EDC HCl 10 mg and NHS 4.5 mg were added, the mixture was well-sealed, stirred at room temperature in dark for 24 hours. Weighed out 12.9 mg BSA dissolved with 2 ml 10 mM PBS pH 7.8. The SAH solution was added slowly to the BSA solution and the mixture was left at 4° C. in dark overnight with stir. Dialyzed the reaction mixture for 72 hours with 1.0 mM PBS pH 7.3. The final volume after dialysis is 8.4 ml with concentration of 1.4 mg/ml.

6. Preparation of SAH-PLL: SAH 1.5 mg was dissolved in 1 ml PBS, EDC.HCl 4 mg and NHS 2 mg were added, then the mixture was well-sealed, stirred at room temperature in dark overnight. Weighed out 1.5 mg PLL dissolved with 4.7 ml 50 mM PBS pH 9.6. The activated SAH was then added slowly to the PLL solution and the mixture was left overnight in dark. Dialyzed the reaction mixture for 48 hours with 10 mM PBS pH 7.3. The final volume after dialysis is 7.0 ml with concentration of 0.93 mg/ml.

Preparation of AdaM-HRP: The procedure for HRP conjugation is similar to that of AdaM-BSA. Weight out 13.8 mg HRP powder (Sigma-Aldrich.) and dissolve it in 2 ml 100 mM sodium bicarbonate buffer, pH. 8.96, in a round bottomed flask. 10 ul aliquot of AdaM-NHS in DMF (10 mg AdaM, EDC 28.2 mg, NHS 10 mg were dissolved in 2 ml DMF, stirred mix for at least 30 minutes) was then added slowly with stir. After about 40 minutes, two solutions were mixed, and further dialyzed with PBS (1.5 liter×4) over 2-3 days.

7. General Procedure for Generating Monoclonal Antibodies Against SAM and SAH:

Mouse monoclonal production is a common practice, based on the procedure developed by the pioneer work of Kolher and Milstein (Nature, 256, 495-497, 1975), Balb/c mice were used for monoclonal antibody immunization and ascites production. Immunization (1 ml total volume) was carried out with subcutaneous injections at multiple sites, initial injection utilizes 1:1 mixture of complete Freund Adjuvant and AdaM-BSA as well as AdaM-KLH conjugate solutions in PBS upon emulsification. Subsequent injections use incomplete Freund adjuvant.

Blood was collected periodically from immunized animals and cells were removed by centrifugation. Antisera thus obtained were then evaluated to determine the immune response and the antibody titer. Depending on application, antibody may be used directly. When necessary, they can be further purified to immunoglobulin level with ammonium sulfate or sodium sulfate or by protein A column chromatography, etc.

For monoclonal antibody, once the clone is obtained it can be injected into host for ascites production. Antibody was then purified from the ascites fluids by protein A affinity column. The hybridoma clone can also be cultured on hollow fiber method to produce antibody.

Mice were primed with intravenous injection of immunogen three days prior to its termination. The spleen of the mouse was harvested and homogenized with a French Press. The spleen cells were then fused with myeloma NS-1 cells in 5:1 ratio. The fused cell suspension was then plated out on 96 wells microtiter plates. The hybridoma cell lines were grown on RPMI1640 enriched with 18% fetal bovine serum, HAT and HT supplements and screened. Clones that are positives to AdaM-PLL conjugate were selected for further studies. Final selection was based on assay performance and cross activity profile. Selected clones were then injected into mice to produce ascites fluid.

Figure 2:
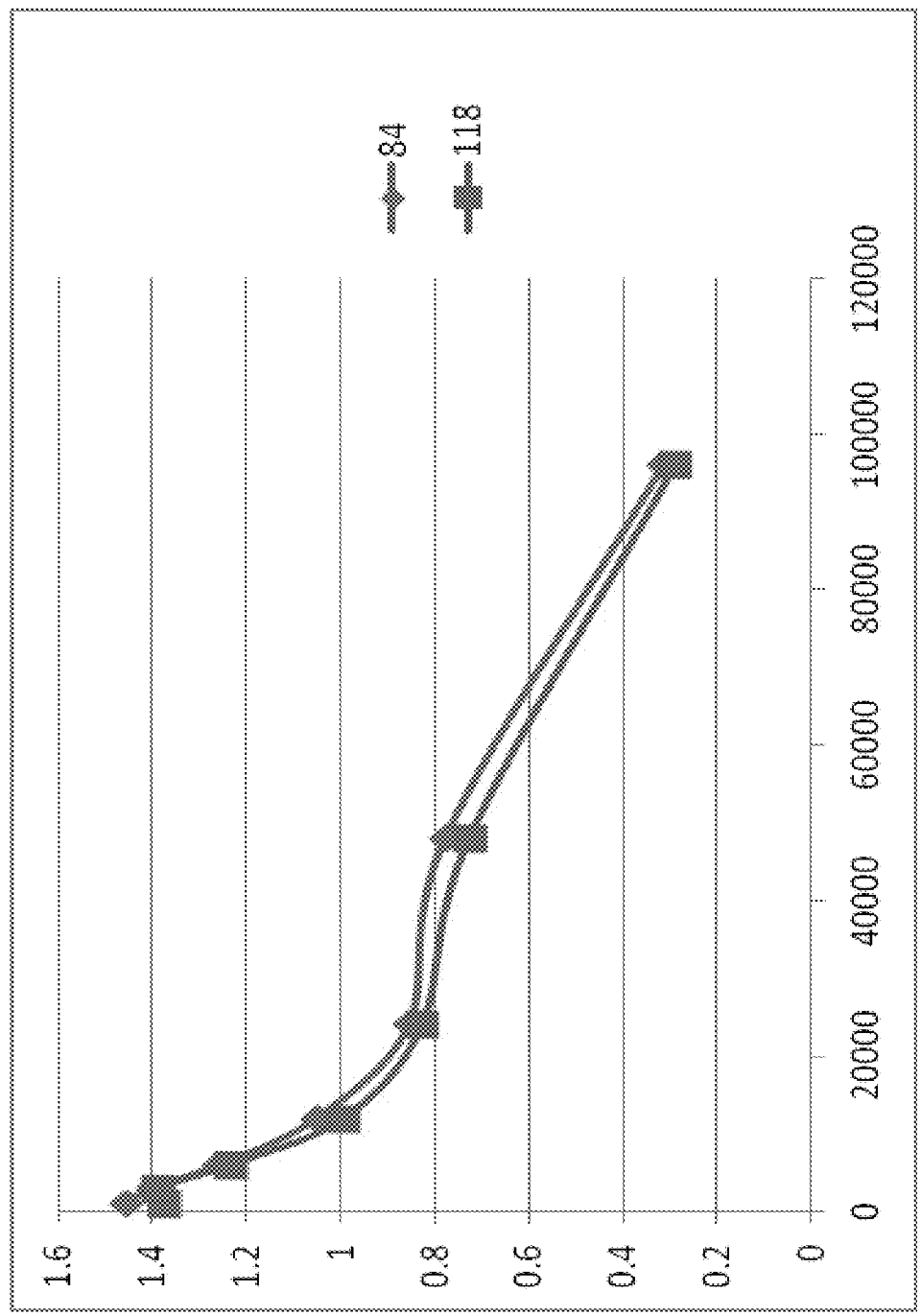
FIG. 2 shows the titers of two monoclonal antibody clones measured by ELISA. The y-axis shows the $OD_{450}$ values. The x-axis shows the dilutions of the purified ascites made at 1 µg/µl.

Through serial screening and selection, we identified a few clones that have a better specificity and less cross reaction with other analogs. The titers of two monoclonal antibodies were tested and the results are shown in FIG. 2.

8. Rabbit Polyclonal Antibodies Against SAM and SAH

New Zealand White rabbits were used for polyclonal antibody production. Immunization (1 ml total volume) was carried out with subcutaneous injections at multiple sites. The immunization process is the same as when immunizing mouse for monoclonal production. The rabbit antiserum was test and the titer was above 1:12000 for both anti-SAM and anti-SAH seria before seria were collected.

Regarding titer of monoclonal antibody, the concentration of the monoclonal antibody is adjusted to 1 mg/ml. Using Immunoassay with HRP, we have got different titers depending on the amount of antigen used and at what OD level the best condition is considered. The titers in the range of 1:1000 to 1:500,000 have been tested.

Figure 3A:
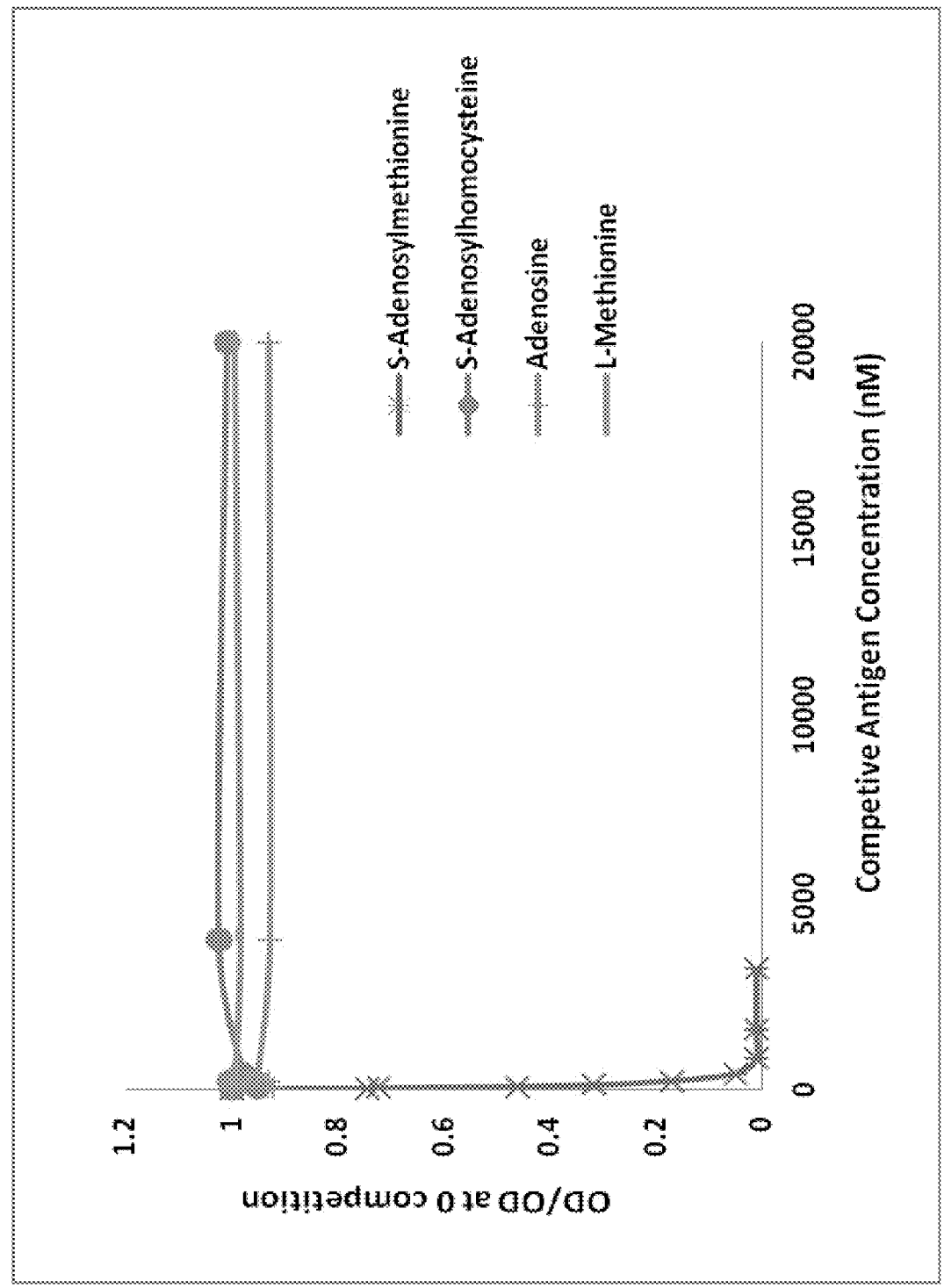
FIG. 3A shows the results of specificity of antibody clone #84-3. Cross reaction with analogs is less than 1%. A sample of the subject hybridoma clone 84-3 was deposited at the China Center For Type Culture Collection (CCTCC) Address: Wuhan University, Wuhan Zip code: 430072 on Sep. 16, 2017, and has been assigned the CCTCC number C2017178.
Figure 3B:
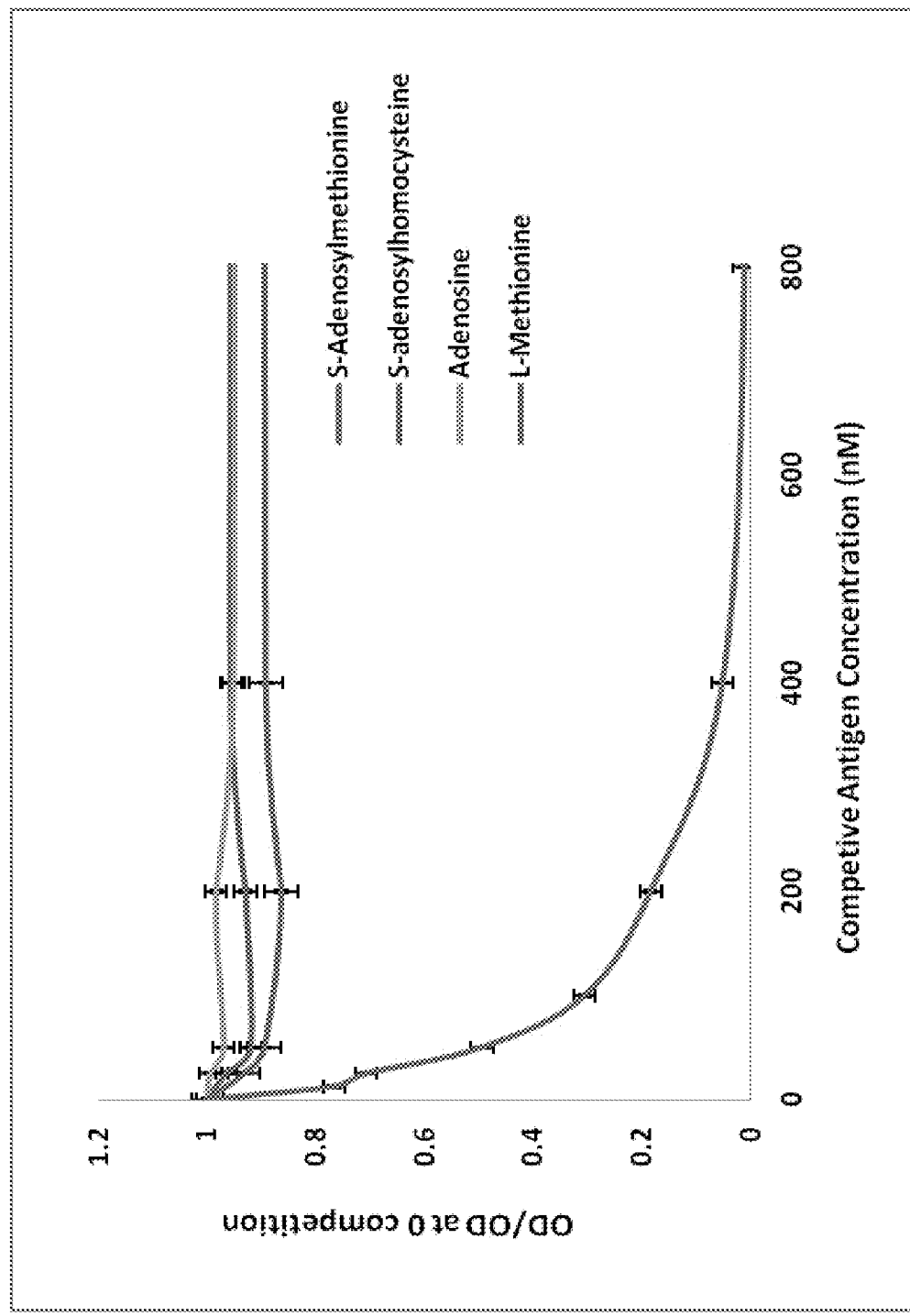
FIG. 3B shows the results of specificity of antibody clone #118-6. Cross reaction with analogs is less than 1%. A sample of the subject hybridoma clone 118-6 was deposited at the China Center For Type Culture Collection (CCTCC) Address: Wuhan University, Wuhan Zip code: 430072 on Sep. 16, 2017, and has been assigned the CCTCC number C2017179.

In our experiments, hundreds of thousands of hybridoma cell lines were obtained, each was tested for its specificity to SAM, SAH, Ade, Met. Binding of the monoclonal antibodies to SAM was much favored over other three analogs mentioned above. Using competitive ELISA, cross reaction to the analogs were analyzed in reference to reaction to SAM. Cross reaction to SAH at 10% and below were tested. FIG. 3A and FIG. 3B show the two monoclonal antibody ones 84-3 (deposited on Sep. 16, 2017 at the China Center For Type Culture Collection as number C2017178) and 118-6 (deposited on Sep. 16, 2017 at the China Center For Type Culture Collection as number C2017179) with the lowest cross reaction to SAH.

Example 2

Antibody Specificity

To further test the specificity of the clones, cross reactions of clone #84 (similar results on #84 sub-clones) with all tested analogs including with SAH, methionine and with adenosine are very low, all <1% (could go further lower) (See FIG. 3A). Three analogs used in the cross reaction are SAH, methionine and adenosine. About 100 folds higher dosages of analogs than that of SAM was used in competitive ELISA. At 10 µM dosage of the SAH, methionine and adenosine, competition of coated antigen did not occur. However, no inhibition was seen by three analogs, the inhibition was clearly seen when SAM was added at a much lower dosage than those of the analogs.

Figure 4:
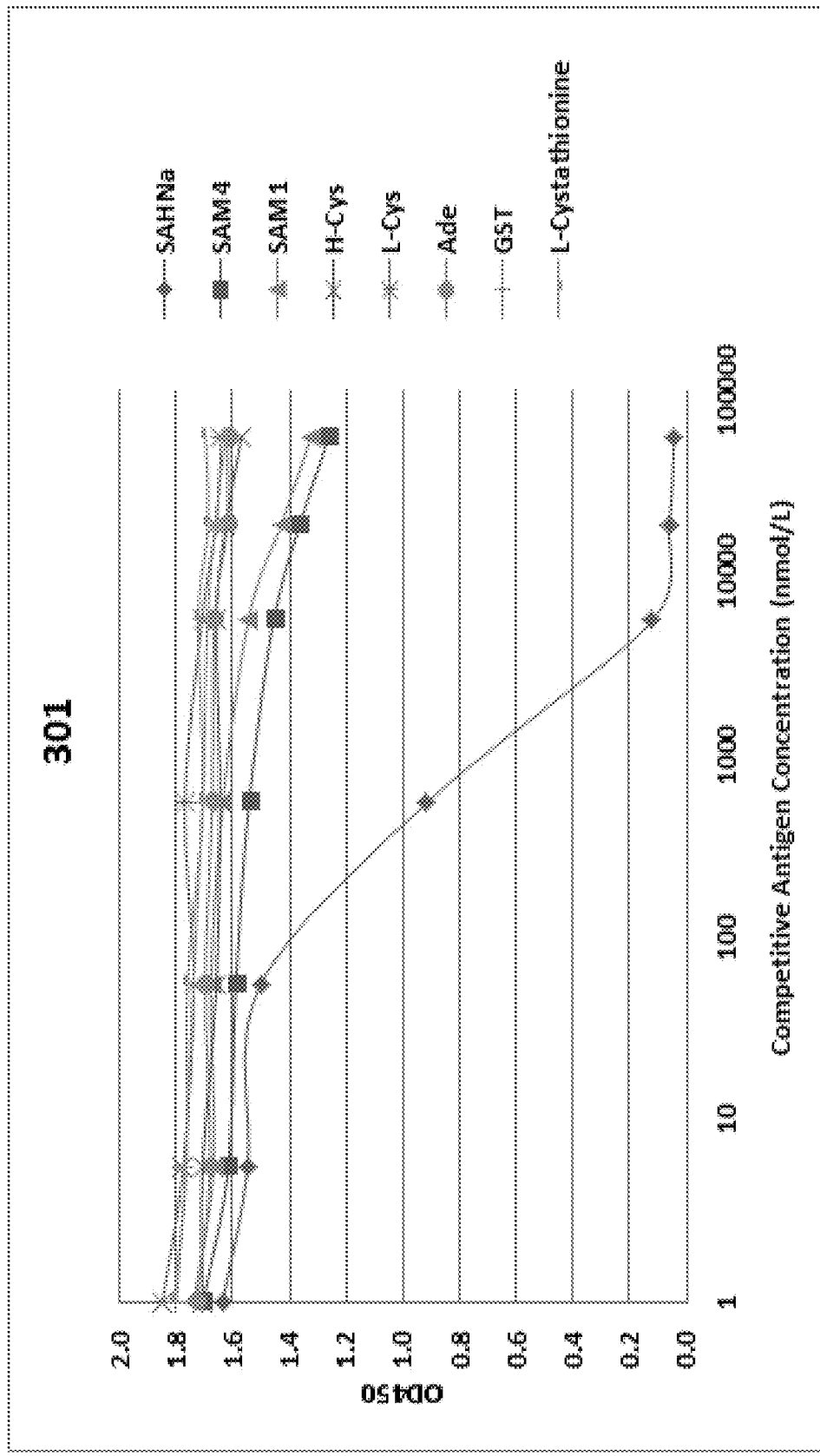
FIG. 4 shows the results of specificity of antibody clone #301-1. Cross reaction with analogs is less than 3%.

Cross reactions of clone #118-6 (deposited on Sep. 16, 2017 at the China Center For Type Culture Collection as number C2017179) (similar results with other #118 sub clones) with all tested analogs including with SAH, methionine and with adenosine are very low, all <1% (could go further lower) (FIG. 3B). The results were similar as clone #84-3 (deposited on Sep. 16, 2017 at the China Center For Type Culture Collection as number C2017178) (similar results with other #84-3 sub-clones). FIG. 4 showed the specificity characterization data for mouse anti-SAH antibody clone #301 (similar for any #301 sub-clones). The calculated cross reaction to SAM is less than 3%, to other tested analogs including with Homocysteine (H-Cys), L-Cysteine (L-Cys), Adenosine (Ade), Glutathione (GST), L-Cystathionine (L-CTT) are very low, all <1% (could go further lower).

Example 3

Antibody Sensitivity

The sensitivity, the lowest detectable value in sample that is defined by the antigen concentration corresponding to the OD450 values that is calculated by adding OD 450 value of blank wells plus 2 or 3 folds of the standard deviation, is about 3 nM (data not shown). Table 1A and Table 1B showed sensitivity experiment using clone #118-6 (deposited on Sep. 16, 2017 at the China Center For Type Culture Collection as number C2017179) and #84-3 (deposited on Sep. 16, 2017 at the China Center For Type Culture Collection as number C2017178), respectively. Table 1A shows cELISA result with 0.05 µg/ml PLL-aza-SAM coated micro-titer plate, HRP-anti-118-6 at dilution of 1:10,000 in PBS incubation system. Different amounts of coating antigen, antibody, and incubating buffer will give slightly different minimum detection limits. The data below showed the minimum detection limit, which was calculated by OD (when antigen=0)−2×Standard deviation=0.65205−2×0.072761=0.5065, was about 7.8125 nM. The results from Table 1B was calculated by OD (when antigen=0)−2× Standard deviation=1.00275−2×0.01223=0.97829, was between 7.8125 to 15.625 nM. With other detecting technology, e.g. chemiluminescent assay and radioactive labeling technology, sensitivity may be further increased.

TABLE 1A

SAM Standard curve (#118-6) (deposited on Sept. 16, 2017 at the China Center For Type Culture Collection as number C2017179)

| Standard (nM) | OD 450 | OD450 |
|---|---|---|
| 0 | 0.6006 | 0.7035 |
| 3.90625 | 0.6390 | 0.6405 |
| 7.8125 | 0.4320 | 0.5738 |
| 15.625 | 0.4033 | 0.4063 |
| 31.25 | 0.2752 | 0.3879 |
| 62.5 | 0.2039 | 0.2123 |
| 125 | 0.1547 | 0.1561 |
| 250 | 0.0866 | 0.1012 |

TABLE 1B

SAM Standard curve (#84-3) (deposited on Sept. 16, 2017 at the China Center For Type Culture Collection as number C2017178)

| Standards (nM) | OD450 | OD450 |
|---|---|---|
| 0 | 0.9927 | 1.0128 |
| 3.90625 | 0.8498 | 0.9258 |
| 7.8125 | 0.8769 | 0.9386 |
| 15.625 | 1.0222 | 1.0265 |
| 31.25 | 0.6903 | 0.5367 |
| 62.5 | 0.3895 | 0.3915 |
| 125 | 0.5111 | 0.4804 |
| 250 | 0.3106 | 0.2383 |

TABLE 1C

SAH Standard curve

| SAH (nM) | OD450 | OD450 | OD450 | Mean | Stdev |
|---|---|---|---|---|---|
| 250 | 0.4116 | 0.4426 | 0.442 | 0.4321 | 0.0177 |
| 125 | 0.5421 | 0.6358 | 0.5372 | 0.5717 | 0.0555 |
| 62.5 | 0.6055 | 0.7115 | 0.6444 | 0.6538 | 0.0536 |
| 31.25 | 0.7285 | 0.8199 | 0.7545 | 0.7676 | 0.0471 |
| 15.625 | 0.8045 | 0.8273 | 0.7975 | 0.8098 | 0.0156 |
| 7.8125 | 0.7602 | 0.8113 | 0.7708 | 0.7808 | 0.0270 |
| 3.906 | 0.7722 | 0.9144 | 0.7786 | 0.8217 | 0.0803 |
| 0 | 0.877 | 0.8992 | 0.8329 | 0.8697 | 0.0337 |

The cELISA result from Table 1C with obtained from 0.5 µg/ml BSA-SAH coated micro-titer plate, HRP-anti-301-1 at dilution of 1:1000 in PBS incubation system. Different amounts of coating antigen, antibody, and incubating buffer will give slightly different minimum detection limits. The data showed the minimum detection limit, which was calculated by OD (when SAH Na=0)−2×Standard deviation=0.8697−2×0.033747=0.8022, was around 15.625 nM.

The titers were tested and were in the range of 1:1000 to 1:500,000 for the mouse anti-SAM antibodies and 1:4000-8000 for mouse anti-SAH antibody with purified antibodies at 1 mg/ml. We have got different titers depending on the amount of antigen used and at what OD level the best condition is judged, etc.

Example 4

Antibody Affinity

To measure the affinity, high (0.1 µg/ml) and low (0.05 µg/ml) concentrations of PLL-aza-SAM (AdaM-PLL) to coat 96-well micro-plate (Costa polystyrene flat bottom 96-well high bind stripwell clear microplate) were used, antibodies are diluted as shown in Table 2 from 1 mg/ml stock concentration. The OD450 were read after HRP-anti-mouse IgG or HRP-anti-rabbit IgG and TMB substrates were added.

TABLE 2A

Anti-SAM antibodies (118-6) (deposited on Sept. 16, 2017 at the China Center For Type Culture Collection as number C2017179) binding to different amount of antigen

| Dilution | Monoclonal anti-SAM 118-6 PLL-aza-SAM | |
| --- | --- | --- |
|  | 0.1 μg/ml | 0.2 μg/ml |
| 100 | 4.4974 | 4.59425 |
| 200 | 4.2144 | 4.71145 |
| 400 | 4.0508 | 4.82100 |
| 800 | 3.9753 | 4.89140 |
| 1600 | 3.8187 | 4.86745 |
| 3200 | 3.6592 | 4.78590 |
| 6400 | 3.3300 | 4.77320 |
| 12800 | 3.2063 | 4.24435 |
| 25600 | 2.6556 | 3.60425 |
| 51200 | 1.8867 | 2.44935 |
| 102400 | 1.2460 | 1.60970 |
| 204800 | 0.7552 | 0.98320 |
| 409600 | 0.4396 | 0.54150 |
| 819200 | 0.2514 | 0.28610 |

From Table 2A, for 118-6 (deposited on Sep. 16, 2017 at the China Center For Type Culture Collection as number C2017179) antibody, when coating antigen was at 0.2 μg/ml, half the maximum OD was seen at about 1:54800. The corresponding antibody concentration was $[Ab]=(1\ mg/ml/160,000\ g/mol)/54800=1.14\times10^{-10}$, where 160,000 is the molecular weight of antibody. When coating antigen was at 0.1 μg/ml, half the maximum OD was observed at about 1:44300. The corresponding antibody concentration was $[Ab]_t=(1\ mg/ml/160,000\ g/mol)/44300=1.41\times10^{-10}$.

$n=(0.1\ \mu g/ml)/(0.05\ \mu g/ml)=2$ $Ka=(n-1)/2*(n[Ab]-[Ab]_t)=5.75\times10^9\ L/mol=1.74\times10^{-10}M$

TABLE 2B

Anti-SAM antibodies (84-3) (deposited on Sept. 16, 2017 at the China Center For Type Culture Collection as number C2017178) binding to different amount of antigen

| Dilution | Monoclonal anti-SAM 84-3 PLL-aza-SAM | |
| --- | --- | --- |
|  | 0.05 μg/ml | 0.1 μg/ml |
| 1000 | 3.3764 | 4.7244 |
| 2000 | 3.2469 | 4.5207 |
| 4000 | 3.1591 | 4.5844 |
| 8000 | 2.9176 | 4.3432 |
| 16000 | 2.6605 | 4.2673 |
| 32000 | 2.1978 | 3.7642 |
| 64000 | 1.6954 | 3.1152 |
| 128000 | 1.2151 | 2.3332 |

For 84-3 (deposited on Sep. 16, 2017 at the China Center For Type Culture Collection as number C2017178) antibody, when coating antigen was at 0.1 μg/ml, half the maximum OD was seen at about 1:130000. The corresponding antibody concentration was $[Ab]=(1\ mg/ml/160,000\ g/mol)/130000=4.807\times10^{-11}$. When coating antigen was at 0.05 μg/ml, half the maximum OD was seen at about 1:7000. The corresponding antibody concentration was $[Ab]_t=(1\ mg/ml/160,000\ g/mol)/7000=8.92\times10^{-11}$.

$n=(0.1\ \mu g/ml)/(0.05\ \mu g/ml)=2$ $Ka=(n-1)/2*(n[Ab]-[Ab]_t)=7.29\times10^{10}\ L/mol=1.37\times10^{-11}M$

TABLE 2C

Anti-SAM polyclonal antibodies binding to different amount of antigen

| Dilution | Polyclonal anti-SA R3 PLL-aza-SAM | |
| --- | --- | --- |
|  | 0.05 μg/ml | 0.1 μg/ml |
| 25 | 4.9225 | 4.9514 |
| 50 | 4.8524 | 4.9929 |
| 100 | 4.3849 | 5.1149 |
| 200 | 3.8518 | 4.8695 |
| 400 | 3.0971 | 4.1802 |
| 800 | 2.2404 | 3.3979 |
| 1600 | 1.5083 | 2.4903 |
| 3200 | 1.0336 | 2.0391 |

From Table 2C, when coating antigen was at 0.1 μg/ml, half the maximum OD was seen at about 1:1500. The corresponding antibody concentration was $[Ab]=(1\ mg/ml/160,000\ g/mol)/1500=4.167\ 10^{-9}$. When coating antigen was at 0.05 μg/ml, half the maximum OD was seen when R3 was diluted at about 1:800. The corresponding antibody concentration was $[Ab]_t=(1\ mg/ml/160,000\ g/mol)/800=7.812\times10^{-9}$.

$n=(0.1\ \mu g/ml)/(0.05\ \mu g/ml)=2$ $Ka=(n-1)/2*(n[Ab]-[Ab]_t)=9.58\times10^8\ L/mol=1.04\ nM$

TABLE 2D

Anti-SAH antibodies (301-1) binding to different amount of antigen

| Dilution from 2 mg/ml | BSA-SAH 1 μg/ml | BSA-SAH 0.5 μg/ml |
| --- | --- | --- |
| 25 | 4.5476 | 4.1062 |
| 50 | 4.775 | 3.5835 |
| 100 | 4.5725 | 3.2796 |
| 200 | 4.2861 | 2.9537 |
| 400 | 4.0144 | 2.6701 |
| 800 | 3.2889 | 2.2375 |
| 1600 | 2.4796 | 1.7737 |
| 3200 | 1.6566 | 1.2864 |
| 6400 | 0.9619 | 0.783 |
| 12800 | 0.4866 | 0.4297 |
| 25600 | 0.2505 | 0.2283 |
| 51200 | 0.1156 | 0.1137 |
| 102400 | 0.0652 | 0.0589 |
| 204800 | 0.0292 | 0.0296 |

From Table 2D, when coating antigen was at 1 μg/ml, half the maximum OD was seen at about 1:1900. The corresponding antibody concentration was $[Ab]=(2\ mg/ml/160,000\ g/mol)/1900=6.58\times10^{-9}M$, where 160,000 is the molecular weight of antibody. When coating antigen was at 0.5 μg/ml, half the maximum OD was observed at about 1:1100. The corresponding antibody concentration was $[Ab]_t=(2\ mg/ml/160,000\ g/mol)/1100=1.136\times10^{-8}M$.

$n=(1\ \mu g/ml)/(0.5\ \mu g/ml)=2$ $Ka=(n-1)/2*(n[Ab]-[Ab]_t)=2.787\times10^8\ L/mol=3.6\times10^{-9}M$

Example 5

Competitive ELISA Assay

Reagents:
IB: 10 mM phosphate, 150 mM NaCl, 0.2% BSA, 0.1% Tween 20, 0.1% Proclin, pH 7.4. Samples: (a) SAM toluenesµlfonate (tosylate) disulfate (Sigma) (b) SAH sodium (MW 406.39) (c) Adenosine (Sigma) (d) Methionine (Sigma). HRP-Goat-Anti-Mouse IgG (H+L) (EarthOx, San Francisco, Calif.). HRP substrate: one reagent substrate solution NeA-blue Tetramethyl-benzidine Substrate. Antigen dilution buffer: D3 with 0.5% BSA. Coating buffer: 50 mM carbonate butter pH 9.6. Washing buffer: PBS, pH 7.5, 0.1% Tween-20.

(1). AdaM-BSA coated micro-plate was blotted, decanted and then competitive SAM, SAH, methionine and adenosine were added in 40 µl antigen dilution butter. The 44 µl of 0.025 µg/ml purified monoclonal antibody against SAM and 16 µl of IB+Tris (100 mM) buffer, pH 8.5 was added and together incubated at 37° C. for 1-2 hours.

(2). The micro-titer plate was washed three times with PBST and blot dry.

(3). To each well was then added 100 µl of properly diluted IMP-goat-anti-mouse antibody and incubated at 37° C. for 20 minutes.

(4). The assay mixture was then decanted, washed, and blot dry.

(6). To each well was added 100 µl/well of HRP substrate and incubate for 10-15 min.

(7). Stop the substrate development with 50 µl/well of 2N $H_2SO_4$.

(8). $OD_{450}$ was recorded.

In order to quantify the amount of SAM in bio-samples, competitive ELISA was developed.

The standards curve for competitive ELISA of SAM and SAH in competitive ELISA is shown in FIG. 4.

The LOGIT is defined as $Ln(A/A0)(1-A/A0)$ where A is the $OD_{450}$ value of a sample or the standard, A0 is the $OD_{450}$ value of the control well. The negative LOGIT value indicates that A/A0 is less than 50% and inhibition rate (1−A/A0) is over 50%, which is an abnormal situation that should not be evaluated normally.

The standard in the amount of 12.60 mg is accurately weighed and was dissolved in small amount of DMF and then thoroughly dissolved in 0.1 mM HCl with 250 ml flask. From it, the 5 µg/ml. 2.5 µg/ml, 1.25 µg/ml, 0.625 µg/ml, 0.3125 µg/ml and 0.15625 µg/ml standard solutions were made in 100 ml flasks respectively.

Figure 5:
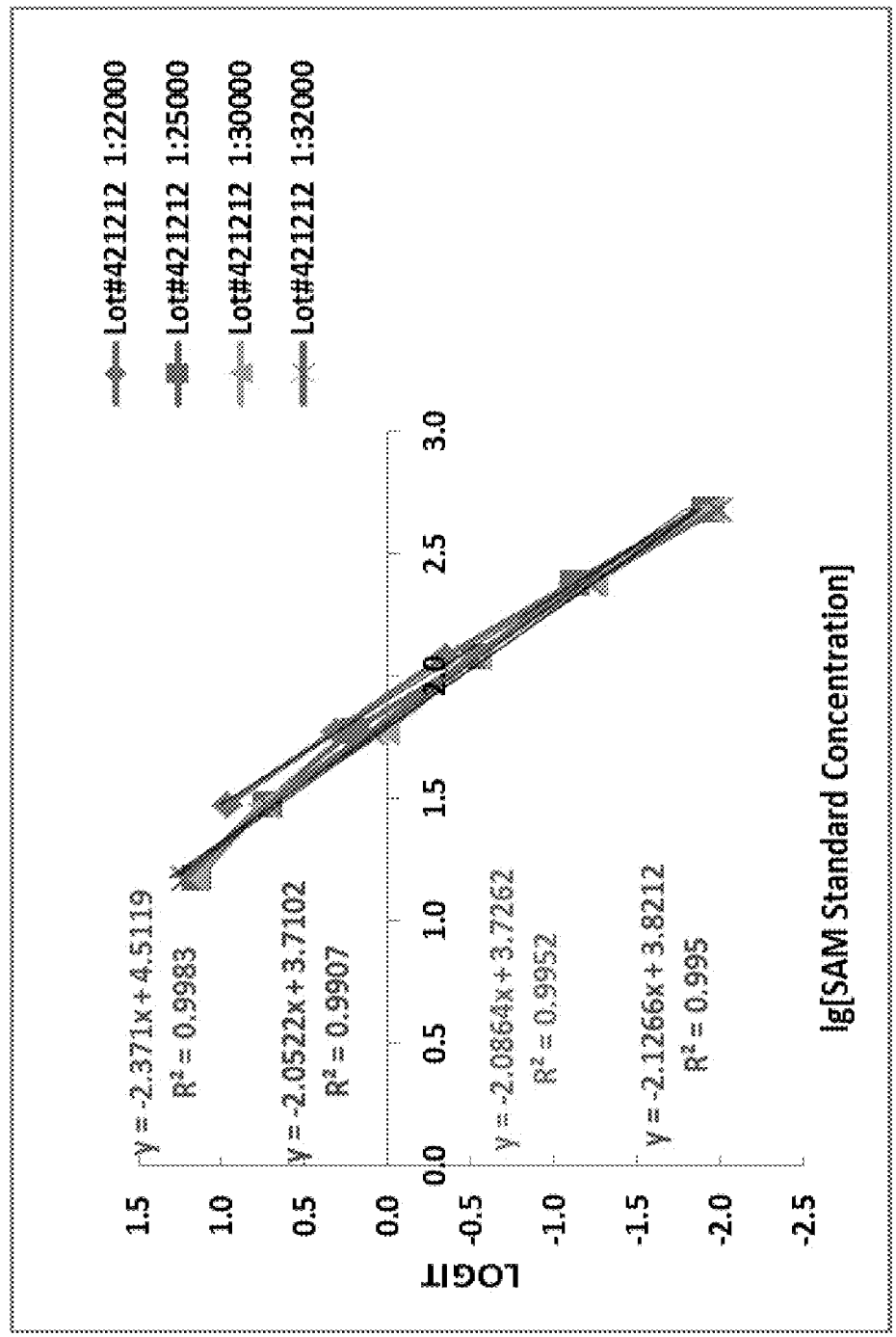
FIG. 5 shows the titer of HRP-anti-SAM (clone 118-6 deposited on Sep. 16, 2017 at the China Center For Type Culture Collection as number C2017179). The 0.25 µg/ml of AdaM-PLL was coated on micro-titer wells. The HRP-anti-SAM was serially diluted and added to the wells. After incubation for about 60 minutes, substrates were added and OD450 was measured.

HRP conjugated monoclonal antibodies against SAM and SAH were generated (FIG. 5). Direct and indirect competitive ELISA methods were developed to quantitatively measure SAM and SAH.

Example 5A

Competitive ELISA Assay Using Rabbit Polyclonal

Using the procedures as outlined in Example 3, competitive ELISA with anti-S-Adenosylmethionine polyclonal antibody [R3] was performed. The Adenosylmethionine AdaM-PLL was coated into 96 wells. Serial dilution of AdaM, S-Adenosylhomocysteine (SAH), Adenosine (Ade), L-Methionine (Met) and 1:15000 of rabbit anti-SAM serum was added. HRP conjugated Goat anti-Rabbit IgG antibody was used to develop the color.

Example 5B

Competitive ELISA Using Anti-S-Adenosylmethionine Monoclonal Antibody [84-3] (Deposited on Sep. 16, 2017 at the China Center For Type Culture Collection as Number C2017178)

The Adenosylmethionine AdaM-PLL was coated into 96 wells. Serial dilution of AdaM, S-Adenosyl-homocysteine (SAH), Adenosine, L-Methionine and 1:35000 of monoclonal antibody purified from hybridoma clone 84-3 were added. HRP conjugated Goat anti-Mouse IgG antibody was used to develop the color.

Example 5C cELISA Using Anti-S-Adenosylmethionine Monoclonal Antibody [118-6] (Deposited on Sep. 16, 2017 at the China Center For Type Culture Collection as Number C2017179)

Figure 6:
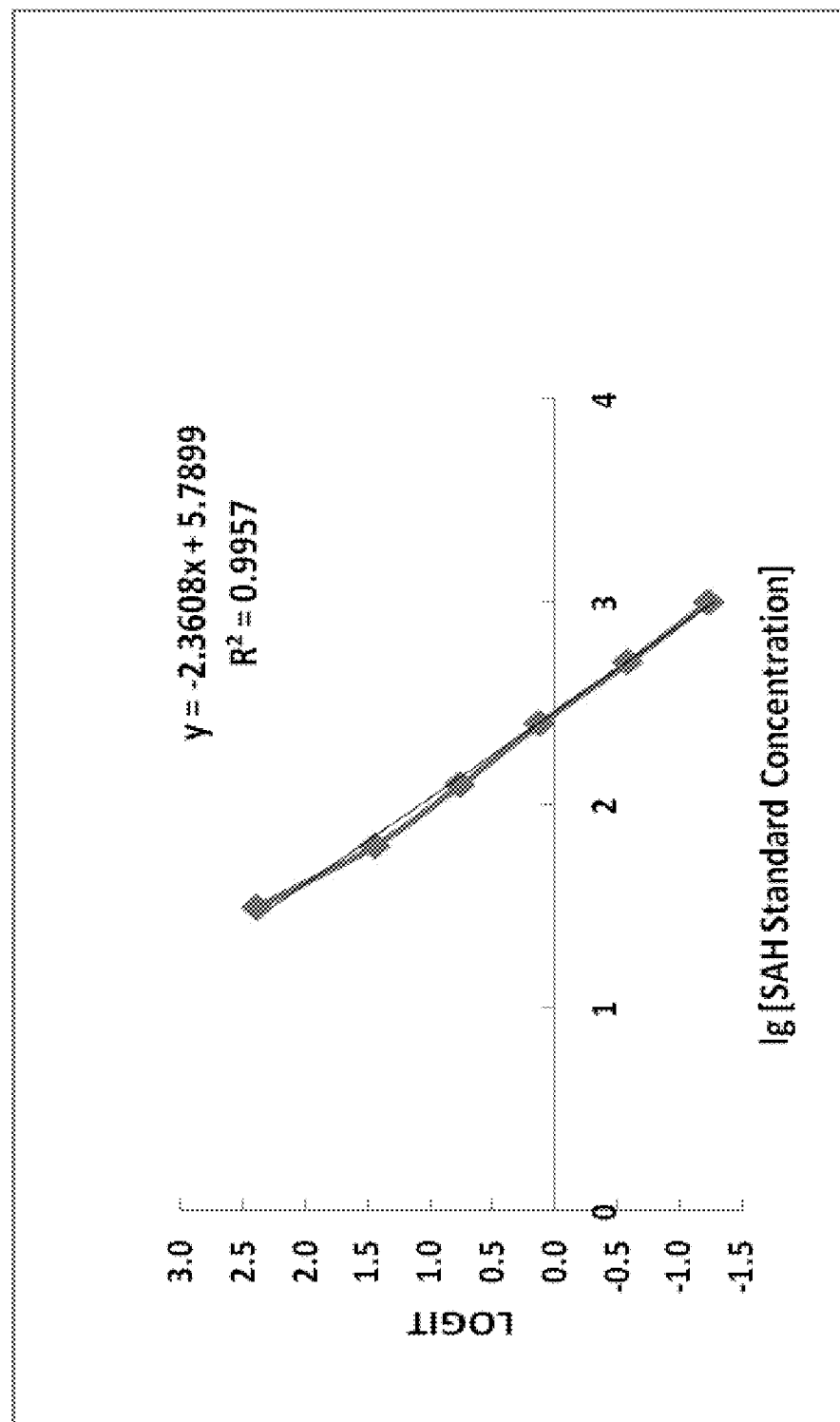
FIG. 6 Standard curve from direct competitive ELISA to quantify SAM. Lot #421212 is one batch of HRP-anti-SAM antibody 118-6 (deposited on Sep. 16, 2017 at the China Center For Type Culture Collection as number C2017179) used. Different dilution of HRP-anti-SAM (1:22000 to 1:32000) gave similar standard curves.

The AdaM-PLL was coated into 96 wells. Serial dilution of SAM standards and HRP conjugated mouse-anti-SAM antibody clone #118-6 at dilution of 1:22000 to 1:32000 was added. After incubation at 37° C. for 60 minutes, plate was washed three times and then TMB substrate was added. After reaction at 37° C. for 10-15 minutes, stop the reaction before measuring OD 450. FIG. 6 shows the standard curve of SAM in direct cELISA. $LOGIT=Ln(A/AS0/(1-A/AS0))$, where A is the OD450 value of a sample or the standard, AS0 is OD450 value of the control well or when no antigen was added. The negative LOGIT value indicates that A/A0 is less than 50% and inhibition rate (1−A/A0) is over 50%.

Example 5D cELISA Using Anti-S-Adenosylhomocysteine Monoclonal Antibody [301-3].

Figure 7:
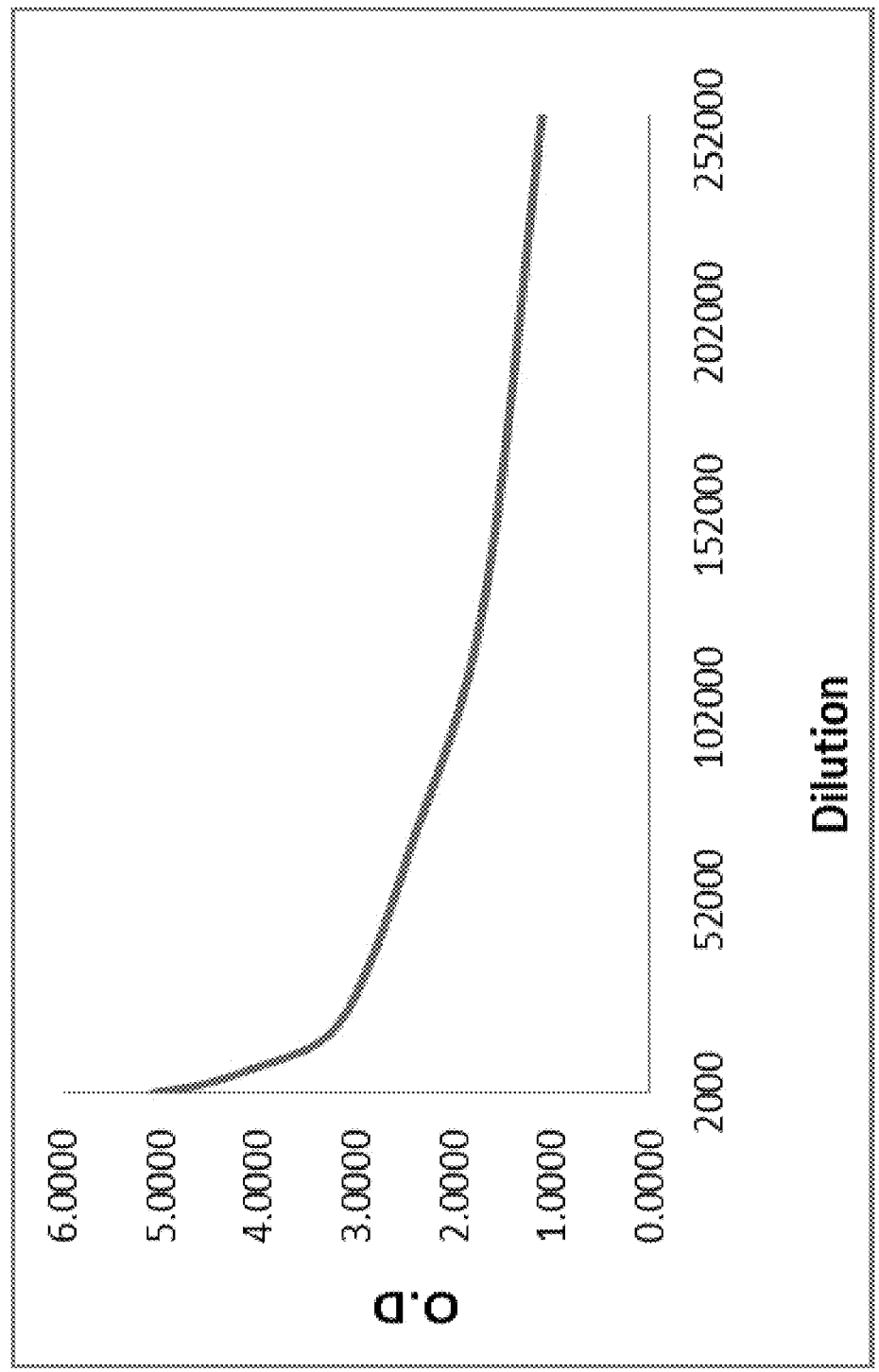
FIG. 7 Standard curve from direct competitive ELISA to quantify SAH. HRP-anti-SAH antibody 301-3 was diluted at 1:2000 for the best result.

BSA-SAH was coated into 96 wells. Serial dilution of SAH-Na standards and HRP conjugated mouse-anti-SAH antibody clone #301-3 at dilution of 1:2000 was added. After incubation at 37° C. for 60 minutes, plate was washed three times and then TMB substrate was added. After reaction at 37° C. for 10-15 minutes, stop the reaction before measuring OD450. FIG. 7 shows the standard curve of SAH in direct cELISA. $LOGIT=Ln(A/AS0/(1-A/AS0))$, where A is the OD450 value of a sample or the standard, AS0 is OD450 value of the control well or when no antigen was added. The negative LOGIT value indicates that A/A0 is less than 50% and inhibition rate (1−A/A0) is over 50%.

Example 6

Compound 1: 2',3'-O-Isopropylideneadenosine (25 g, 82 rnrnol, 1 equivalent) and dry pyridine (200 mL) were placed into a single neck, 500 mL round bottom flask along with a magnetic stir bar then placed under nitrogen atmosphere. The flask was then heated with a heat gun while stirring vigorously. After approximately 5 minutes all solids dissolved. Once in solution, the mixture was cooled in an ice-water bath and stirred for 20 minutes. Tosyl-CI was added as a solid in 8 small portions over 1 hour to prevent a significant exotherm. The mixture was kept at 0° C. for 5 days. Once the reaction was complete by TLC, the mixture was diluted with 100 mL H$_2$O and 300 mL of ethyl acetate. The mixture was transferred to a separatory funnel and 100 mL of 3N HCl was added. The layers were separated and the organic layer was washed with five 200 mL portions of water to remove excess pyridinium hydrochloride. The organic layer was concentrated under reduced pressure then the residue was taken up in 100 mL of dichloromethane. This was slowly added to a stirring solution of heptane (1.12 L) via addition funnel. The off-white precipitate was filtered off to give 31.1 grams of pure product confirmed by mass spec and 1H NMR.

Example 7

Compound 2: Compound 1 (32.2 g, 70 mmol) was added to a 300 mL sealed tube along with a magnetic stirbar. Around 200 mL of a 2M solution of methylamine in THF was poured into the tube and the tube was sealed. The vessel was submerged into a 50° C. oil bath then stirred for two days. The reaction vessel was taken out of the oil bath and then placed into an ice-water bath and stirred for 30 minutes. The cap was then removed and the excess methylamine was blown out by sparging with a gentle stream of nitrogen. The residue was then transferred to a round bottom flask and concentrated under a reduced pressure. The gum-like residue was purified by flash column chromatography (5% MeOH in DCM) to give 3.51 grams of 2. The structure was confirmed by 1H NMR.

Example 8

Compound 3. Amine 2 (5.0 g, 15.6 mmol, 1 equivalent) was placed into a single necked 500 mL round bottom flask. 150 mL of dry acetonitrile was added followed by diisopropyl-ethylamine (2.1 g, 16.38 mmol, 1.05 equivalents) and stirred at 35° C. for 30 minutes. Bromobutyrate (2.55 g, 14.1 mmol, 0.9 equivalents) was added drop-wise via syringe, followed by tetrabutylammonium iodide (288 mg, 0.78 mmol, 5 mol %). The mixture was stirred at 40° C. for 5 days. The reaction mixture was then concentrated under reduced pressure and purified by flash chromatography (5% MeOH in DCM) to provide 5.36 grams of the desired product in 82% yield.

Example 9

Compound 4. Methylester 3 (7.76 g, 18.4 mmol, 1 equivalent) was placed in a 250 mL round bottom flask and taken up in 15 mL of methanol and 15 mL H$_2$O and stirred for 10 minutes. Solid lithium hydroxide (1.55 g, 36.8 mmol, 2 equivalents) was added and the mixture was stirred for approximately 2 hours (until TLC and LCMS showed the complete disappearance of starting material). The crude mixture was concentrated to dryness and then carried on to the next step without further purification.

Example 10

Compound 5: Approximately 7 grams of the crude lithium salt 4 was dissolved 150 mL of 3N HCl and stirred at ambient temperature for 4 hours (until starting material completely disappeared on TLC and LCMS). The crude mixture was filtered through filter paper then concentrated to dryness under reduced pressure. The crude residue was purified in 5 portions on a 120 gram reverse phase column eluting the product at a gradient of 40% methanol in water. The purified fractions were pooled and then concentrated to dryness under high vacuum at 40° C. The product was a brown foam that collapsed back to a brown oil upon standing. The product was confirmed by HPLC. MS. and 1H NMR. 4.8 grams of 99.55% pure (HPLC) product was then divided and transferred into 9 vials with a 1:1 mixture of methanol and water. Each sample was then concentrated to dryness under high vacuum at 40° C. until the mass remained constant.

Example 11

Blood Sample Collection Procedure

Blood samples were obtained from normal volunteers and patients with consent. For plasma sample collection, peripheral venous blood was drawn into tubes with EDTA and mixed well. The tubes were cooled immediately at 4° C. and centrifuged at 2000 g for 15 minutes within 30 minutes after blood collection to obtain plasma. The plasma was either used in measurement or frozen under −20° C. to −70° C. for future use. For serum sample collection, peripheral venous blood was drawn into serum separating tubes and was placed in the refrigerator for about 2 hours till blood coagulation was obviously visible. To help collect serum properly, the serum tubes were centrifuged at 2000 g for 15 minutes at 4° C. The serum was either used in measurement or frozen under −20° C. to −70° C. for future use.

Example 12

Blood samples were obtained from cancer patients who were hospitalized for chemotherapy. The samples were measured with direct competitive ELISA assay for SAM and SAH levels. The average level of SAM for cancer patients was 103±52 nM, and the SAH level was 250±90 nM from 12 samples. The average methylation index was less than 0.5. More samples and observations with diagnostic details, symptoms, cancer stages, progression, treatment, relapse and prognostic information are being conducted to generate a complete profile of the human methylation index and its relationship to various aspect of cancer at different levels. Blood samples are also collected from various patients with other types of cancers before and after chemotherapy. The DNA methylation level will be measured from the white blood cells as well. The relationship between particular DNA methylation disorders from cancer patients and methylation index or DNA global methylation is also expected to provide further impact on state of health and therapeutic protocols.

Example 13

Blood samples were obtained from patients having liver disorders such as contagious hepatitis (some accompanying bile problems including Cholestasis), liver cirrhosis, fibrosis and then analyzed for SAM and SAH levels with direct competitive ELISA. The average level of SAM in plasma was 45±8 nM from 26 samples. The level of SAM in liver disorders was much lower than that of normal people. The SAH level was 342±129 nM, however, higher than that of normal people. The methylation index was about 0.13.

Example 14

Blood samples were obtained from patients having been diagnosed as depression and then analyzed for SAM as follows:

Blood samples from depressed patients will come from The Second Xiangya Medical College Hospital Psychiatric Institute of Health for those depressed patients without obvious organic damages or diseases, as well as from The Second Ningbo Hospital Neurology Department and Rehabilitation Department for those depressed patients with some organic diseases. We especially compare SAM and SAH levels in depressed patients who take SAM-e or other medicines before and after treatment of depression. The level of SAM was 20±18 nM and SAH was 340±180 nM from 10 samples. The methylation index was around 0.064. SAM or methylation index can be a good indicator to personalize depression therapy and aids in prognostic prediction. Qualitative and semi-quantitative SAM rapid test strips are convenient choices available for patients who need to decide whether to take SAM-e or other anti-depression medicines. This helps direct patients to choose the medicines that best fit them.

Example 15

Patients with stage 1 cancer are examined and their SAM levesl and SAH levels are measured and the methylation indeces are calculated. Pateints with methyltion indecss of less than 2 are started with SAM once a day while they are udnergoing chemotherapy.

Example 16

Measuring methylation index from urine (or blood sample if urine cannot be used normally because of some special components in it or the concentration of SAM in urine is too low) is a good way to personalize depression therapeutics. SAMe therapeutical protocol may look like this:
For adult patients, depending on the severity of the mood and other health problems, many regimens have been used, for example:
Daily doses of 800-L600 mg of SAMe by mouth for up to 6 weeks.
Doses of SAMe have been given through IV or injected into the muscle, ranging from 200 to 400 mg daily at most 8 weeks.
Doses of 1,000-1,600 mg have been taken by mouth daily for 15 days to 6 weeks.
Doses of 150-400 mg given through IV daily for 3-4 weeks are most common.
A dose of 400 mg of s-adenosyl-L-methionine 1,4-butane-disulphonate stable salt (Knoll Farmaceutici S.p.A., Liscate, Milan, Italy) has been injected into the muscle daily.
Doses of 75-200 mg of SAMe have been injected into the muscle for 14-30 days.
Doses of 200-400 mg of SAMe per 250 milliliters of saline have been given through IV during the first three days of treatment, followed by 400 mg of SAMe daily on days 4-14.
Use the methylation index ELISA kit developed in this invention to measure methylation index once every 3-5 days for patients who take higher dosage (more than 400 mg daily) to adjust the dosages of SAMe timely. If the methylation index increases too fast (increase 5 folds between measures or by 0.5 or when patients can experience obvious symptoms associated with using SAMe.), reduce dosage is recommended especially for patients who have high blood pressure or other cardiovascular problems. High risk groups should have methylation index tested daily or use the SAM and SAH rapid test kid to qualitatively or semi-quantitatively test SAM and SAH levels in blood or urine daily to ensure the safety of SAM administration to avoid any side effects.

For those who take SAM-e less than 400 mg daily by mouth, have methylation index tested, or at least SAM tested when needed, or just have it tested weekly to get some idea of whether the dosage is right for the patient as well as when to stop taking the medicine.

Do not stop SAM medication unless methylation index is back to normal and stabilized for a week or two.

For those depression patients who have normal or close to normal methylation index, do not use SAMe as the first choice of therapeutics. Instead, use other type anti-depression medicines. But methylation index may still be a good marker to monitor the effectiveness of other treatment. Have methylation index tested regularly is still important to determine when the treatment can be stopped.

Example 17

Measuring methylation index from urine (or blood sample if urine cannot be used normally because of some specially components in it or the concentration of SAM in urine is too low) is a good way to personalize liver and/or cholestasis therapeutics. SAM-e therapeutical protocol may look like this:

For adult patients, depending on the severity of the liver and/or cholestasis and other health problems, many regimens have been used, for example: 1,600 mg of SAMe has been taken by mouth daily for 2 weeks.
A dose of 1,000 mg has been injected into the vein (IV) daily for 4 weeks.
To treat bile flow problems in pregnancy, 500 mg of Transmetil® has been given by slow infusion twice daily for 14 days, followed by 500 mg of SAMe taken by mouth twice daily until or after delivery. A dose of 600 mg of Samyr® has been taken by mouth alone.
A dose of 1,800 mg of Samyr® has been taken by mouth together with beta-mimetics daily.
A dose of 500 mg has been taken by mouth twice daily.
Doses of SAW that have been given include: 1,000 mg injected into the muscle daily until delivery, 200 or 800 mg given through IV daily for 20 days; 800 mg given through IV daily in two divided doses until delivery; 800 mg given through IV; and 800 mg given through IV over three hours for 20 days. A dose of 800 mg of disulfate-p-toluene sulfonate stable salt (BioResearch, S.p.A, Milan, Italy) has been given through IV daily.
Use the methylation index ELBA kit developed in this invention to measure methylation index once every 3 days for patients who take higher dosage (more than 600 mg daily) to adjust the dosages of SAMe timely. If the methylation index increases too fast (increase 5 folds between measures or by a certain number when patients can experience obvious symptoms associated with using SAMe.), reduce dosage is recommended especially for patients who have high blood pressure or other cardiovascular problems. High risk groups should have methylation index tested daily or use the SAM and SAH rapid test kid to qualitatively or semi-quantitatively test SAM and SAH levels in blood or urine daily to ensure the safety of SAM administration to avoid any side effects.

For those who take SAM-e less than 600 mg daily by mouth, have methylation index tested, or at least SAM tested when needed, or just have it tested weekly to get some idea of whether the dosage is tight for the patient as well as when to stop taking the medicine.

Do not stop SAM medication unless methylation index is back to normal and stabilized for a week or two.

Example 18

Flow Cytometry Procedure

About 1 million L-02 and Hep G2 cells were washed and fixed with 4% Paraformaldehyde for 1 hour at 4° C. Then 0.2% Triton X-100 was added for 15 minutes at 4° C. After washing, the cells was incubated with 1:200-1:400 diluted anti-SAM monoclonal antibodies or polyclonal antibody in buffer containing goat serum at 4° C. overnight. Alexa Fluor® 488 Goat Anti-Mouse IgG (H+L) antibody was added after washing with PBS for 40 minutes at room temperature. Washed again with TBS and PBS twice before adding 1% Paraformaldehyde, then cells were run and analyzed using Becton Dickinson flow cytometry instrument.

Use of Anti-SAM Antibodies in Flow Cytometry (FCM)

Flow Cytometry (FCM) was carried out with normal human liver cell line L02 and hepatocyte carcinoma cell line Hep G2 cells. Two anti-SAM monoclonal antibodies 84-3 and 118-6 (deposited on Sep. 16, 2017 at the China Center For Type Culture Collection as number C2017179) as well as polyclonal antibody R3 were used in the FCM assays. FIG. 11A-14 show results from two of the assays using monoclonal antibodies.

Figure 8:
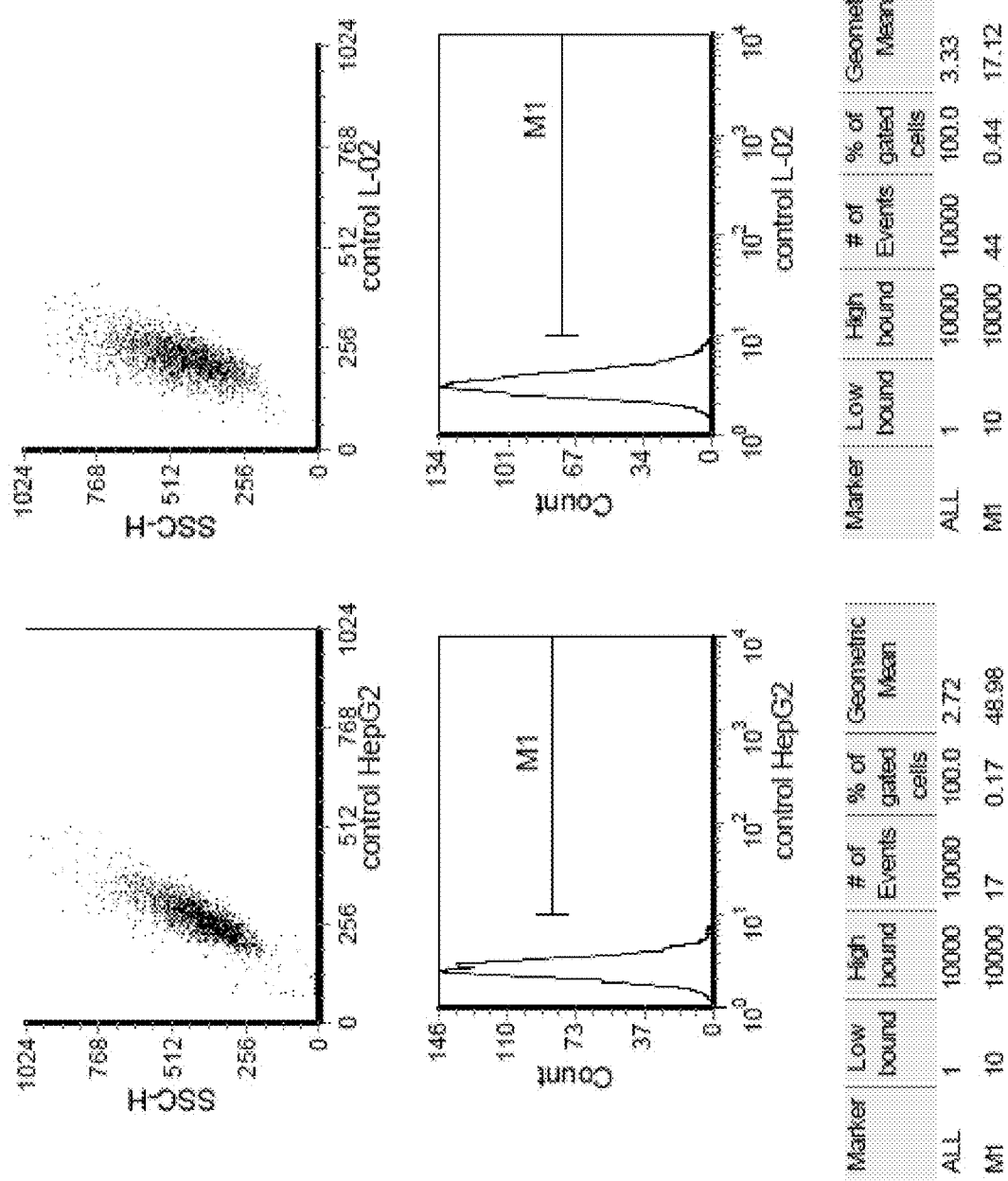
FIG. 8 illustrates the FCM results from normal liver cell line L02 and hepatocyte carcinoma cells line Hep G2 not stained with any antibody (FCM analysis control).

FIGS. 8A and 8B show the FCM analysis control in an assays with anti-SAM antibody. A and B showed results from two independent experiments. Normal liver cells L02 and carcinoma cells Hep G2 were stained with the buffer without any antibody.

Figure 9:
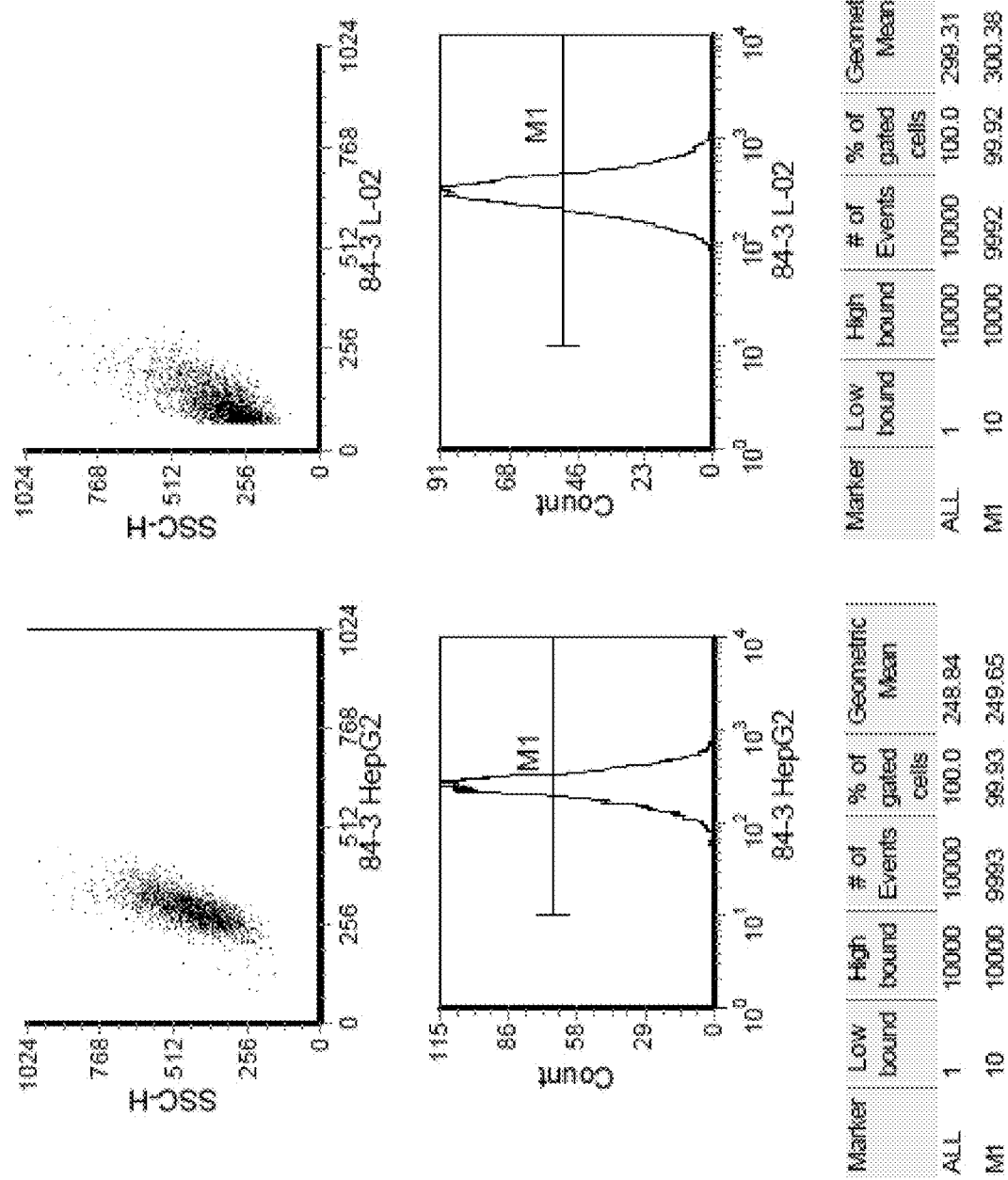
FIG. 9 illustrates the FCM results from normal liver cell line L02 and hepatocyte carcinoma cells line Hep G2 stained with anti-SAM monoclonal antibody from clone 84-3 (deposited on Sep. 16, 2017 at the China Center For Type Culture Collection as number C2017178).

FIGS. 9A and 9B illustrate the FCM results from normal liver cell line L02 and hepatocyte carcinoma cells line Hep G2 stained with anti-SAM monoclonal antibody from clone 84-3 (deposited on Sep. 16, 2017 at the China Center For Type Culture Collection as number C2017178). A and B showed results from two independent experiments. Average fluorescence signal in Hep G2 cells was reduced compared to that in L02 cells, indicating SAM level is reduced during carcinogenesis.

Figure 10:
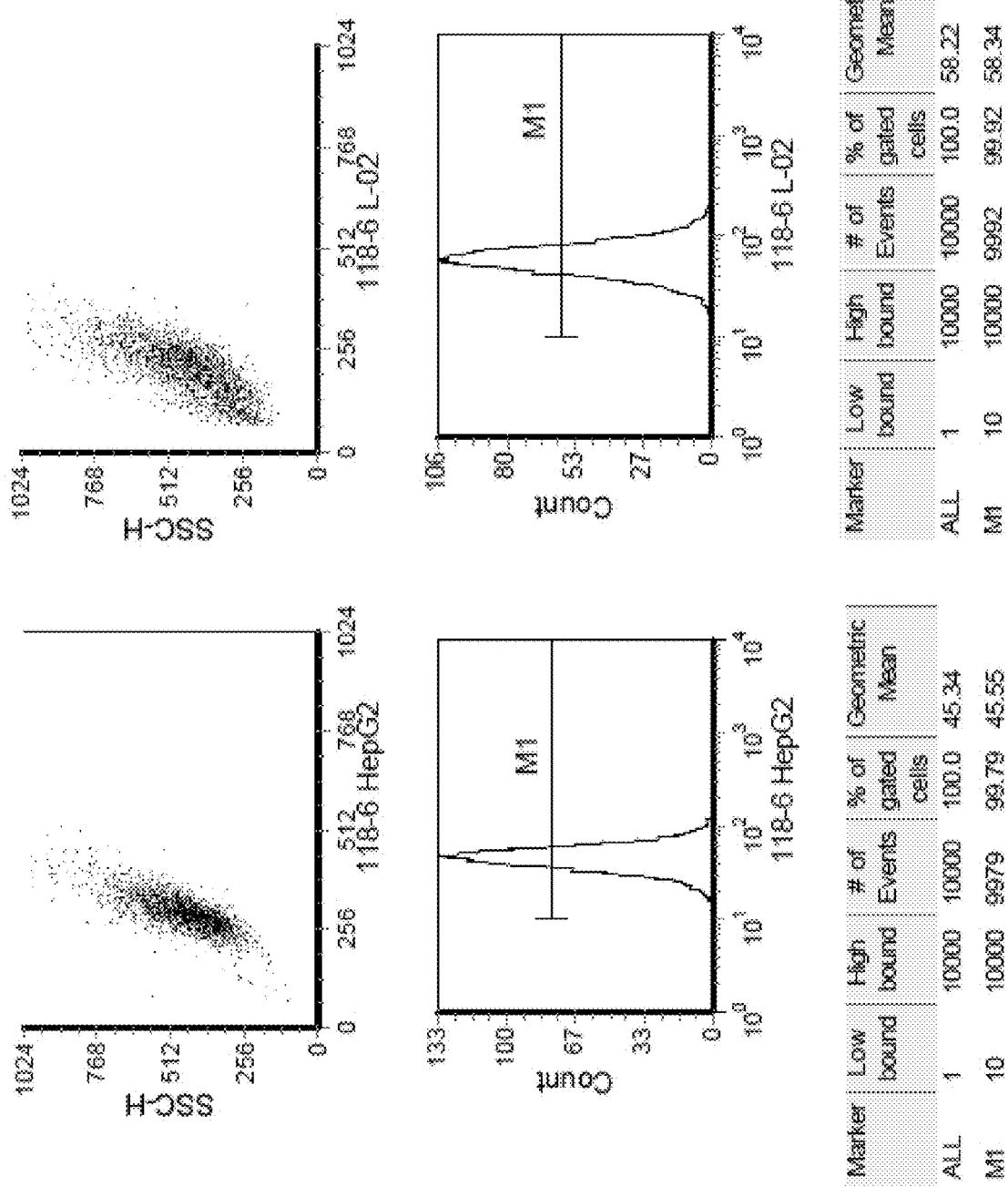
FIG. 10 shows the FCM results from normal liver cell line L02 and hepatocyte carcinoma cell line HepG2 stained with anti-SAM monoclonal antibody from clone 118-6 (deposited on Sep. 16, 2017 at the China Center For Type Culture Collection as number C2017179).

FIGS. 10A and 10B show the FCM results from normal liver cell line L02 and hepatocyte carcinoma cell line stained with anti-SAM monoclonal antibody from clone 118-6 (deposited on Sep. 16, 2017 at the China Center For Type Culture Collection as number C2017179). A and B showed results from two independent experiments. Average fluorescence signal in Hep G2 cells was reduced compared to that in L02 cells, indicating SAM level is reduced during carcinogenesis.

Figure 11:
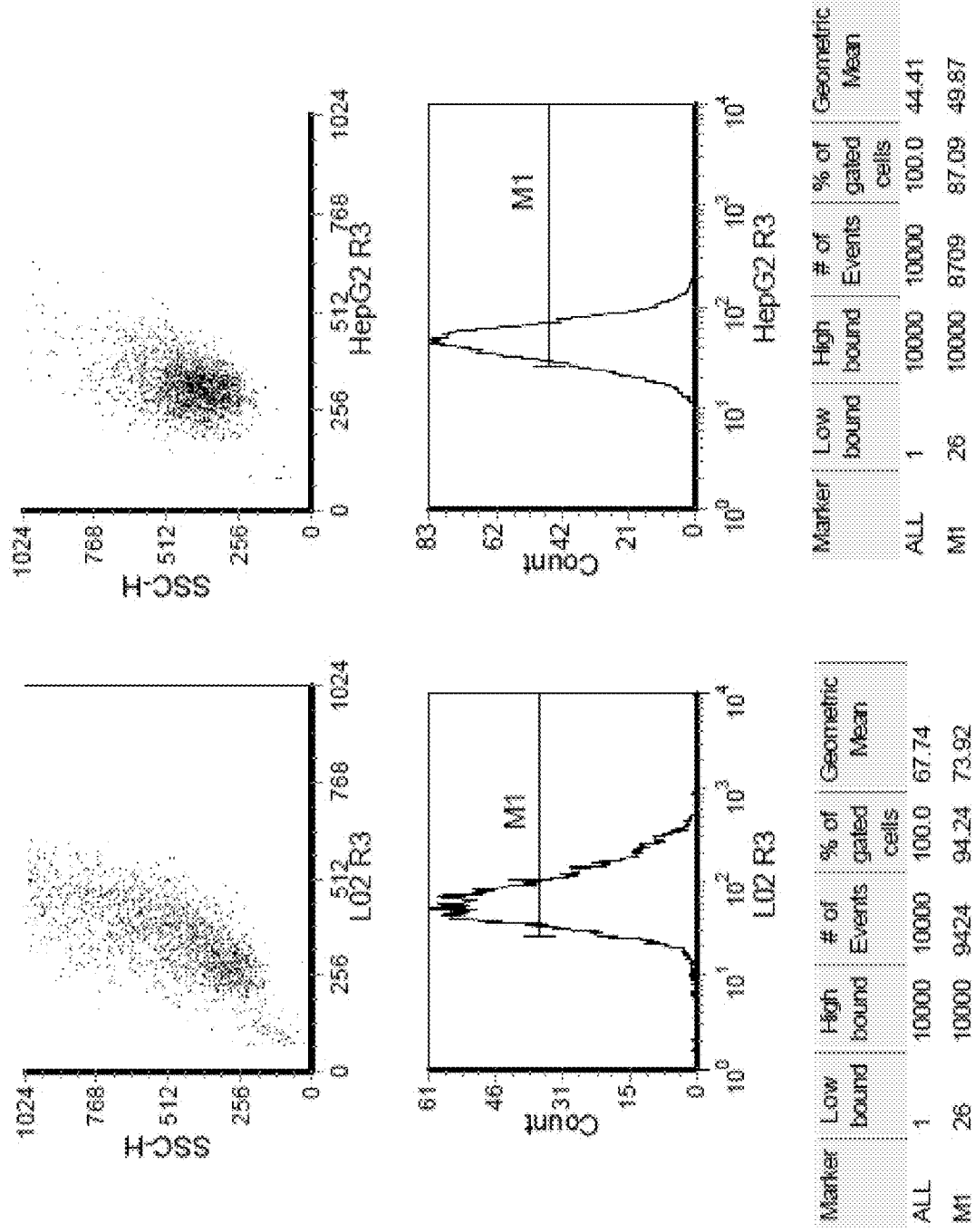
FIG. 11 illustrates the FCM results from normal liver cell line L02 and hepatocyte carcinoma cell line Hep G2 stained with anti-SAM polyclonal antibody R3.

FIG. 11 illustrates the FCM results from normal liver cell line L02 and hepatocyte carcinoma cell line Hep G2 stained with anti-SAM polyclonal antibody R3. Average fluorescence signal in Hep G2 cells was reduced compared to that in L02 cells, indicating SAM level is reduced during carcinogenesis.

Figure 12:
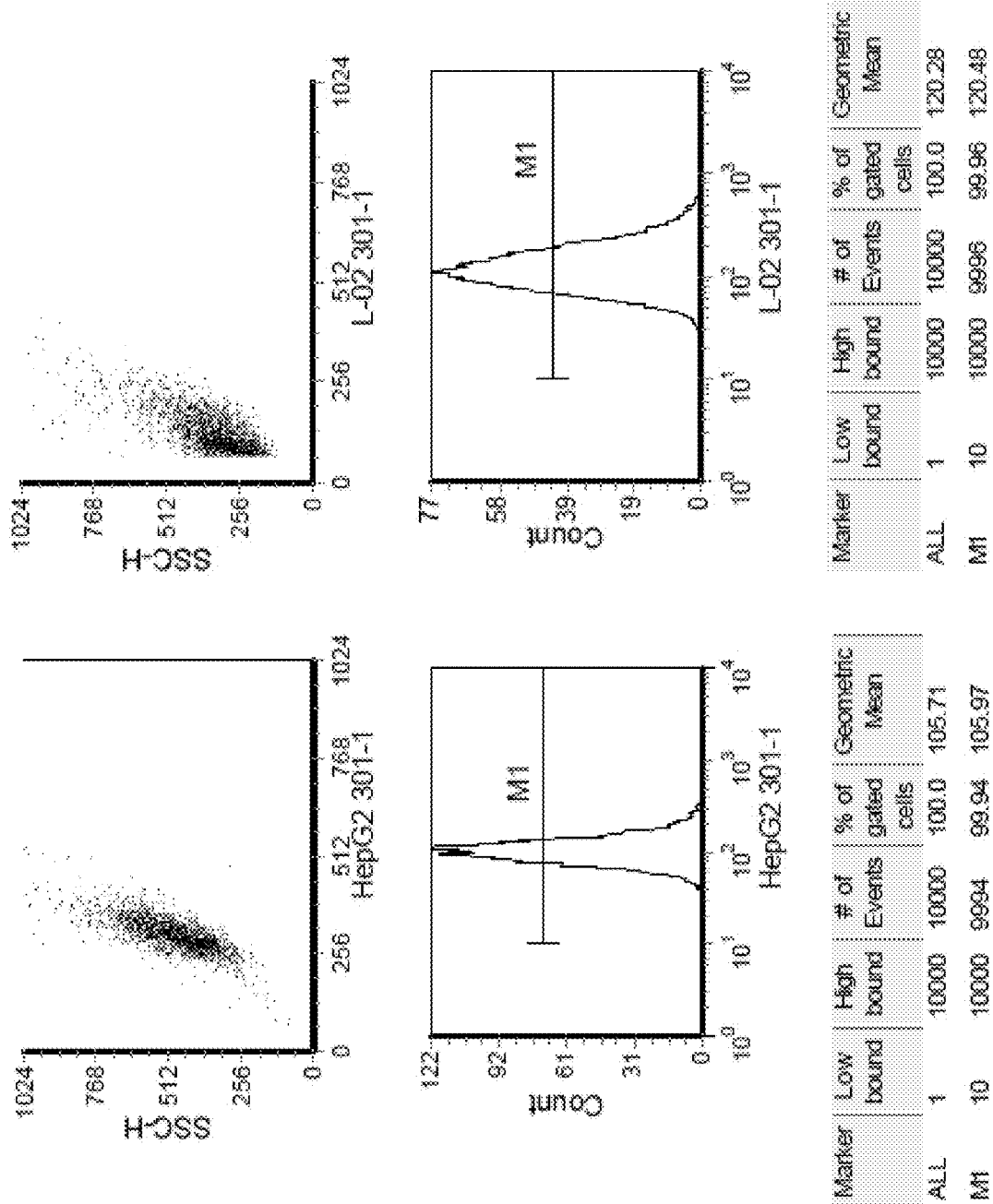
FIG. 12 show the FCM results from normal liver cell line L02 and hepatocyte carcinoma cell line stained with anti-SAH monoclonal antibody from clone 301-1.

FIG. 12 illustrates the FCM results from normal liver cell line L02 and hepatocyte carcinoma cell line HepG2. Cells were stained with mouse anti-SAH monoclonal antibody 301-1. Average fluorescence signal in HepG2 cells was reduced compared to that in L02 cells, indicating SAH level is reduced during carcinogenesis.

After deducting the fluorescence values from the control samples, average geometric means for the 1 million cells injected, Table showed the averages of fluorescent geometric means of 2 FCM tests. Meanwhile we observed that the monoclonal antibody from clone 84-3 (deposited on Sep. 16, 2017 at the China Center For Type Culture Collection as number C2017178) has much higher fluorescence values than the monoclonal antibody from clone 118-6 (deposited on Sep. 16, 2017 at the China Center For Type Culture Collection as number C2017179) and polyclonal antibody, suggesting there may exist some additional or different properties of monoclonal antibody from clone 84-3 and the properties do not exist in monoclonal antibody from clone 118-6 (deposited on Sep. 16, 2017 at the China Center For Type Culture Collection as number C2017179) and the polyclonal antibody.

TABLE 3

Averages of geometric means from FCM

| Antibody | L02 | HepG2 | Decrease (%) |
|---|---|---|---|
| Mouse anti-SAM (84-3) | 164.81 | 48.74 | 70 |
| Mouse anti-SAM (118-6) | 36.08 | 13.44 | 64 |
| Rabbit anti-SAM (R3) | 34.57 | 9.72 | 72 |
| Mouse anti-SAH (301-1) | 103.36 | 56.99 | 45 |

Example 19

Immunohistochemistry Procedure

To stain cells or tissue sections, slides are blocked with blocking buffer (1% BSA in PBS) for 30 minutes at room temperature and incubated with 1:10-1:20 diluted anti-SAM monoclonal antibodies or polyclonal antibodies. After rinsing twice with TBST (50 mM Tris/HCl pH 7.6, 150 mM NaCl, 0.05% Tween-20), slide was incubated with HRP labeled goat-anti-mouse IgG for 2 hours. After twice with TBST, slides were treated with Diaminobenzidine (DAB) reagents to visualize staining. Slides can then be counter-stained with hematoxylin, dehydrated (if required), and mounted for microscopy examination.

Use of Anti-SAM Antibodies in Immunohistochemistry (IHC)

Using the procedure above several normal cells and cancer cells as well as sections from different organs were stained.

Figure 13:
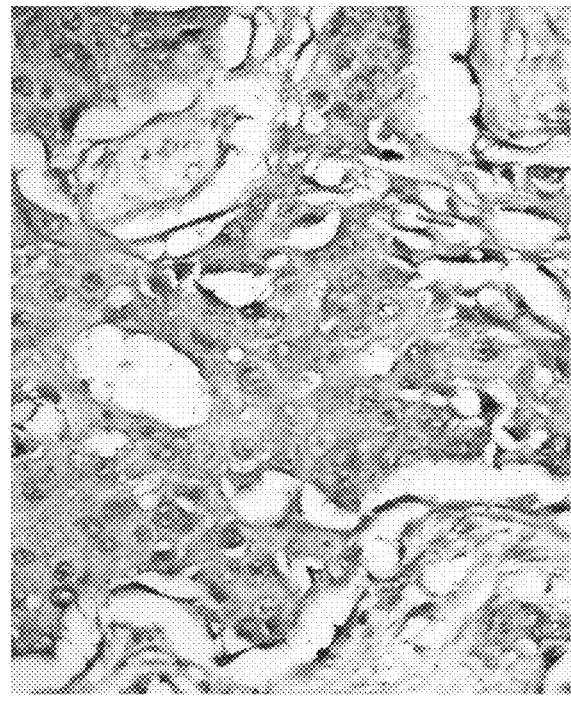
FIG. 13 shows the use of anti-SAM monoclonal antibody from clone 118-6 (deposited on Sep. 16, 2017 at the China Center For Type Culture Collection as number C2017179). in performing IHC with normal and cancerous breast pathological slide.
Figure 13:
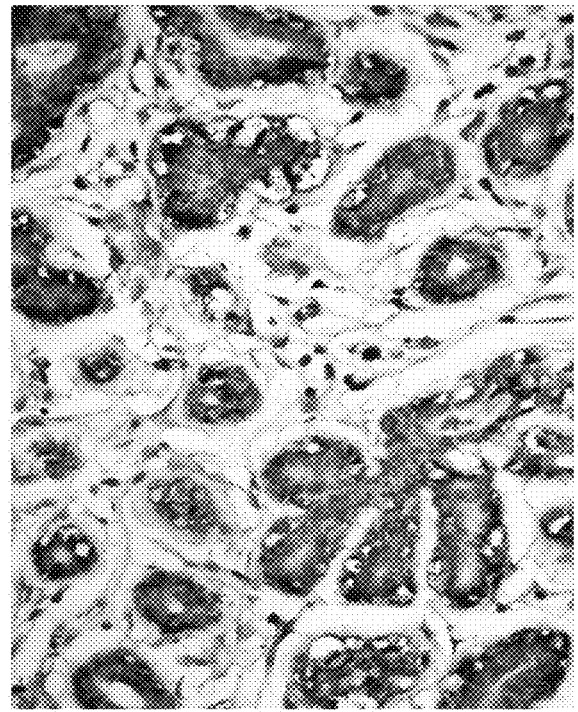

FIG. 13 shows use of anti-SAM monoclonal antibody from clone 118-6 (deposited on Sep. 16, 2017 at the China Center For Type Culture Collection as number C2017179) in performing IHC with normal and cancerous breast pathological slide. The results indicated dramatically reduced cytoplasmic and nuclear SAM specific staining (brown color indicates where SAM is) in carcinoma cells compared to the surrounding normal breast tissue. Cytoplasmic and nuclear areas from B showed negative or much weak or background staining. A (left): benign breast cancer adjacent to cancer region shown in B; B (right): breast cancer tissue (×400). Antibody was diluted at 1:200.

Figure 14:
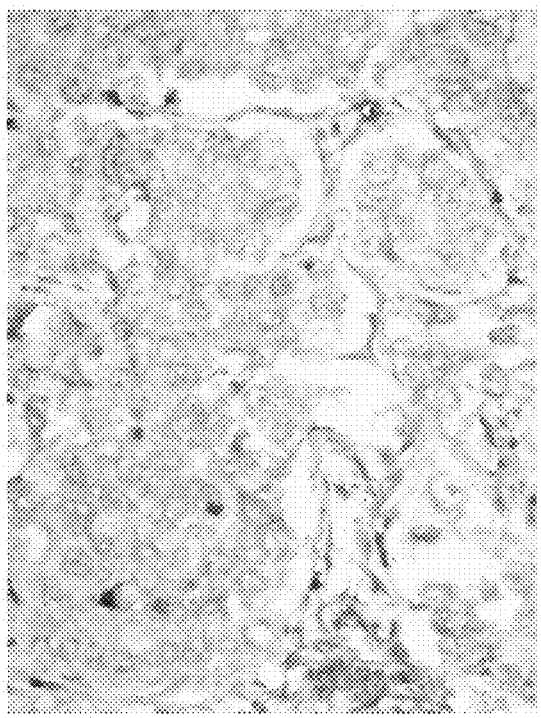
FIG. 14 illustrates use of anti-SAM monoclonal antibody from clone 118-6 (deposited on Sep. 16, 2017 at the China Center For Type Culture Collection as number C2017179), in performing IHC with normal and cancer lung pathological slides.
Figure 14:
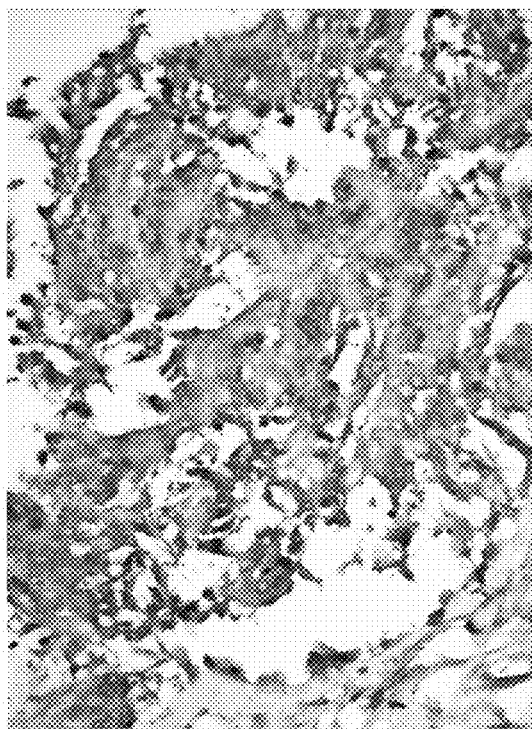

FIG. 14 illustrates use of anti-SAM monoclonal antibody from clone 118-6 (deposited on Sep. 16, 2017 at the China Center For Type Culture Collection as number C2017179) in Performing IHC with normal and cancer lung pathological slides. The results indicated a dramatically reduced cytoplasmic and nuclear SAM specific staining (brown color indicates where SAM is) in carcinoma cells compared to the surrounding normal lung tissue. Cytoplasmic and nuclear areas from Picture B showed negative or background staining. Picture A (left): benign lung cancer adjacent to cancer region shown in Picture B; Picture B (right): lung cancer tissue (×400). Antibody was diluted at 1:200.

Figure 15:
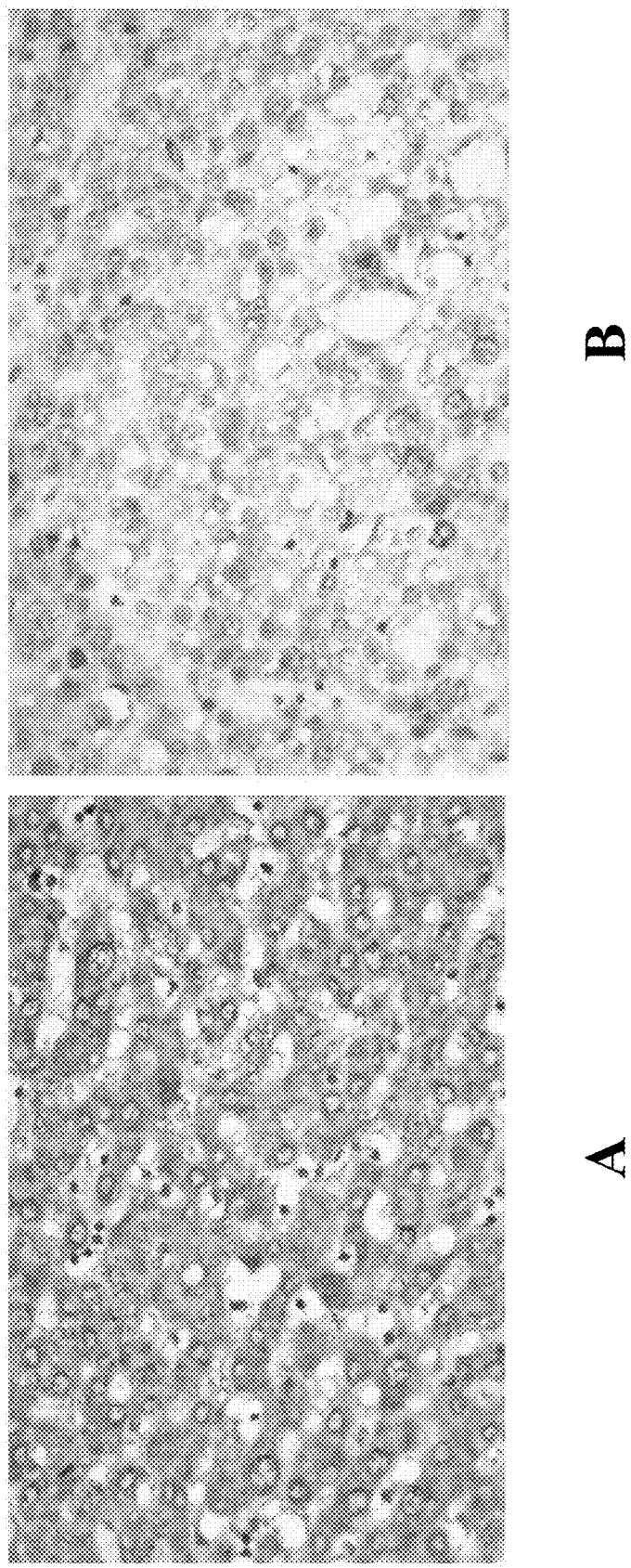
FIG. 15 shows the use of anti-SAM monoclonal antibody from clone 118-6 (deposited on Sep. 16, 2017 at the China Center For Type Culture Collection as number C2017179) in performing IHC with normal and cancerous liver pathological slides.

FIG. 15 shows the use of anti-SAM monoclonal antibody from clone 118-6 (deposited on Sep. 16, 2017 at the China Center For Type Culture Collection as number C2017179) in performing IHC with normal and cancerous liver pathological slides. The results indicated a dramatically reduced cytoplasmic and nuclear SAM specific staining in carcinoma cells compared to the surrounding normal liver tissue. Cytoplasmic and nuclear areas from Picture B showed negative staining. A (left): benign liver cancer adjacent to cancer region shown in Picture B; Picture B (right): liver cancer tissue (×400). Antibody was diluted at 1:200.

Figure 16:
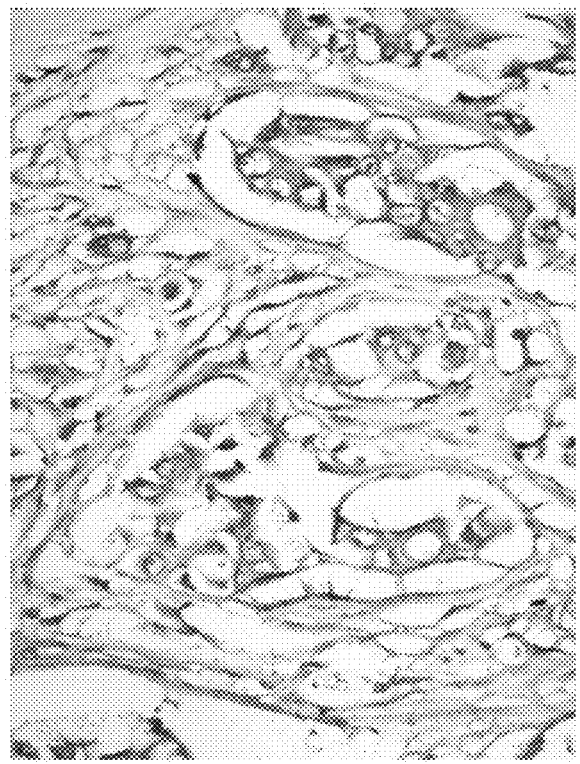
FIG. 16 illustrates the use of anti-SAM polyclonal antibody R3 in performing IHC with normal and cancerous breast pathological slide.
Figure 16:
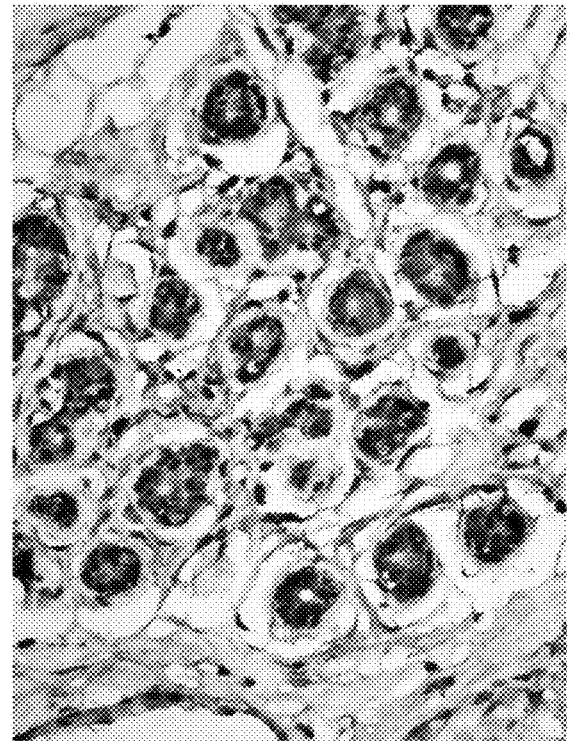

FIG. 16 illustrates the use of anti-SAM polyclonal antibody R3 was used in performing IHC with normal and cancerous breast pathological slide. The results indicated a dramatic reduce in cytoplasmic and nuclear SAM specific staining in carcinoma cells compared to the surrounding normal breast tissue. Cytoplasmic and nuclear areas from Picture B showed negative staining. Picture A (left): benign breast cancer adjacent to cancer region shown in Picture B. Picture B (right): breast cancer tissue (×400). Antibody was diluted at a ratio of 1:20.

Figure 17:
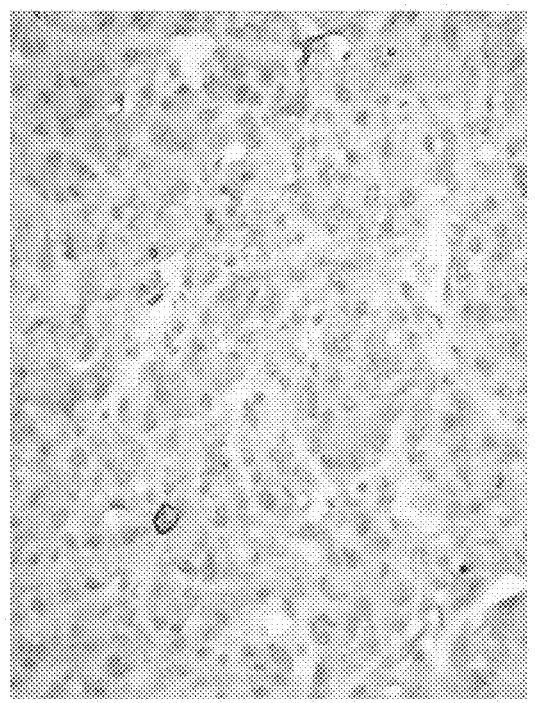
FIG. 17 shows the use of anti-SAM monoclonal antibody from clone 118-6 (deposited on Sep. 16, 2017 at the China Center For Type Culture Collection as number C2017179) in performing IHC with normal and cancerous nephritic pathological slide.
Figure 17:

FIG. 17 shows the use of anti-SAM monoclonal antibody from clone 118-6 (deposited on Sep. 16, 2017 at the China Center For Type Culture Collection as number C2017179) in performing IHC with normal and cancerous nephritic pathological slide. There were not much change in the SAM specific staining in the carcinoma cells compared to the surrounding benign nephritic tissue. Picture A (left): benign kidney tissue adjacent to cancer region shown in Picture B. Picture B (right): kidney cancer tissue. Antibody was diluted at 1:200.

Figure 18:
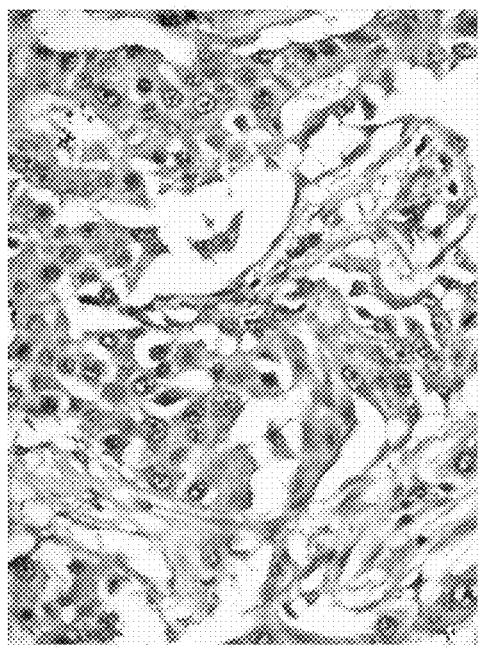
FIG. 18 shows the use of anti-SAH monoclonal antibody from clone 301-1 in IHC with normal and cancerous breast pathological slides.
Figure 18:
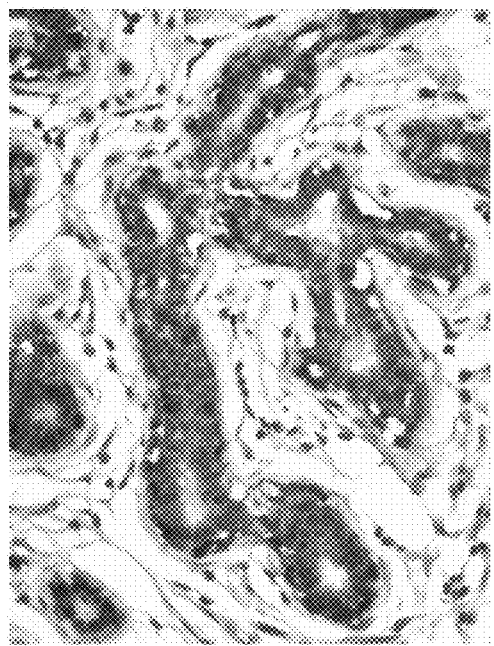

FIG. 18 shows the use of anti-SAH monoclonal antibody from clone 301-1 in IHC with normal and cancerous breast pathological slides. The results indicated dramatic decrease in cytoplasmic and nuclear SAH specific staining in carcinoma cells compared to the adjacent normal breast tissue. Cytoplasmic and nuclear areas from picture B showed reduced staining. Picture A (left): normal breast tissue adjacent to cancer region shown in picture B. Picture B (right): breast cancer tissue. Antibody was diluted at 1:50.

It is foreseeable that different cancer cases may give different results because each case is different, e.g. different stages, overall health condition, treatments used and complications of other diseases, and so on. Benign tissues stained with anti-SAM antibody were positive to a different degree but the malignant tissues all showed negative or reduced intracellular SAM concentration.

Immunofluorescence (IF) and IHC assays of SAM molecule of culture cells, tissue sections, biopsy cells, peripheral blood cells, and even exfoliated cells of various tissues or origins are helpful in giving us insights in evaluating pathological status of cells examined. High SAM level indicates healthy condition or benign progression or disease improvement is under way. Though qualitative in nature, the difference is so obvious that qualitative methods still serve the purpose.

On the other hand, FCM is a good way to quantify the level of SAM by calculating the geometric means of a population of a million cells, which may provide a better statistic result than what can be seen from a slide or cell smear. The usage area of FCM is relatively narrow. It is mostly used in in vitro studies of culture cells, human peripheral blood white blood cells and biopsy cells from experimental animals.

Our investigation showed the results from FCM are consistent with the results found in IHC and IF that intracellular SAM level is drastically reduced in carcinoma cells whereas SAM is abundant in normal cells. More studies are needed to better quantify the extent to which SAM level changes with various situations and factors.

Example 20

Competitive Rapid Test Strip Procedure (Direct Method)
(1) Monoclonal antibodies against SAM and SAH were labeled with colloidal gold, subsequently were sprayed evenly onto a glass fiber mat, dried at 50° C. for 12 hours. (2) 0.2 mg/ml BSA or PLL labeled SAM analogs or SAH (or SAH sodium salt) was evenly scribed into the nitrocellulose membrane, dried at 50° C. for 1 hour. (3) The absorbent paper, nitrocellulose membrane (NC membrane) from step (2), colloidal gold mat from step (1) and sample pad (to absorb and filter samples) were aligned and placed evenly one layer after the other. Strips were cut into 3 mm wide with chop cutting machines. (4) To detect samples, first test the control by inserting the strip into 100 µl sample dilution buffer. In about 5 minutes, an obvious purple-like band was developed. Dipped the strips into sample solution, when the SAM or SAH levels from the samples were higher than the predetermined cutoff values, the bands were not shown or lightly shown, whereas if the SAM or SAH levels were lower than cutoffs, the color bands showed up like in the control band.

Competitive Rapid Test Strip Procedure (Indirect Method)
(1) Goat anti-mouse IgG was labeled with colloidal gold, subsequently were sprayed evenly on colloidal gold mat, dried at 50° C. for 12 hours. (2) 0.2 mg/ml BSA or PLL labeled SAM analogs or SAH (or SAH sodium salt) was evenly evenly scribed into nitrocellulose membrane, dried at 50° C. for 1 hour. (3) The absorbent paper, nitrocellulose membrane (NC membrane) from step (2), colloidal gold mat from step (1) and sample pad (to absorb and filter samples) were aligned and placed evenly one layer after the other. Strips were cut into 3 mm wide with chop cutting machines. (4) Negative control was tested by inserting the strip into 100 µl sample dilution buffer. In about 10 minutes, there was no band developed, indicating the system behaved correctly. (5) Positive control was tested by diluting monoclonal antibodies against SAM and SAH properly (e.g. 5 ng/ml), dipped the strips into it. The obvious purple-like blue bands were developed. (6) To detect SAM or SAH from samples, mixed 50 µl monoclonal antibodies against SAM and SAH in doubled concentration of those used in step (5) and 50 µl unknown samples, dipped the strip into it. The results were read in about 10 minutes. If the band was clearly seen, then the SAM or SAH levels from the samples were lower than the predetermined cutoff values. If the bands were not shown or lightly shown, it indicated that the SAM or SAH levels were higher than cutoff values.

Example 21

Thermal Stability of SAM and SAH

The stability of SAM and SAH at different temperatures, as well as their stability in acid and base environment were tested. The 310 human plasma samples were placed at room temperature for 2 hours. Compared to the same samples that were continuously placed under 4° C., the levels of SAM were reduced by 33.81%±19.43%, the levels of SAH were increased by 21.05%±83.31%. The increased SAH was due to de-methylation of SAM in ex vivi situation within a few hours of blood withdrawal. Possible reasons for the increased standard deviation from SAH assays might include SAH value varies significantly among samples, competitive ELISA assay per se (very sensitive to subtle changes) as well as variations of assay on different days using different assay plates.

Additional SAM thermal stability experiments were performed with normal plasma from volunteers (our lab scientists). Volunteers' information is as follows:

TABLE 4

Normal Plasma Samples used in Stability Study

| Identification | Gender | Age | BMI | General Health |
|---|---|---|---|---|
| S1 | Male | 33 | 25.26 | Very Good |
| S2 | Male | 28 | 19.60 | Very Good |
| S3 | Male | 55 | 22.04 | OK |
| S4 | Female | 23 | 20.55 | Very Good |
| S5 | Male | 53 | 22.49 | Very Good |
| S6 | Female | 21 | 17.63 | OK |
| S7 | Female | 24 | 19.80 | Very Good |
| S8 | Mixed unknown number of plasma from blood center | | | |

Results from stability study for different temperature conditions, i.e. 4° C., 15° C. (room temperature), 37° C. and 56° C., were obtained mainly on SAM and partially on SAH measurements. Plasma from 4 individual samples S3, S4, S5 and S6 were used in 4° C., 15° C. and 37° C. experiments. The results were shown in FIG. 19 A-F.

Degradation rate under 4° C. showed big variety among individuals (FIG. 19 A-B). However, when samples were placed at room temperature (~15° C.) and 37° C., SAM was degraded rapidly especially at 37° C., SAM degradation rate reached a maximum at about 4-6 hours under 37° C. SAH levels showed increase with time goes by. FIG. 19D showed levels of plasma SAM and SAH change over time at 15° C. At about 6 hours after blood withdrawal, SAM level was reduced whereas SAH level was increased. The values of SAH were recorded as >1000 nM from 6 hours to 3 days, thus SAH leaks were not shown. The level of SAH was maintained at a high level for about 3 days before it started to drop. SAM level went down continuously. It indicated that methyltransferases were still active and the process of converting SAM into SAH may last for a couple of days after blood withdrawal if left under fairly cold environment. It cannot be ruled out that inhibition of SAH converting to other metabolites or degradation also existed causing it to stay high for quite some time. It meant to show the dynamics of SAM and SAH for this particular sample. Difference among samples exists. Samples S1, S2, S3 and S4 were used in 56° C. experiments. The results are shown in FIG. 19F-G. SAM was quickly undetectable in 10 minutes at 56° C., whereas SAH was dramatically degraded in 10 minutes and fully undetectable after about 4 hours at 56° C. SAH level was dramatically decreased within the first 10 minutes, which indicated that existing plasma SAH was first degraded, then more newly generated SAH contributed the slight increase, and SAH level went down again due to the high temperature condition which caused faster degradation.

Figure 19A:
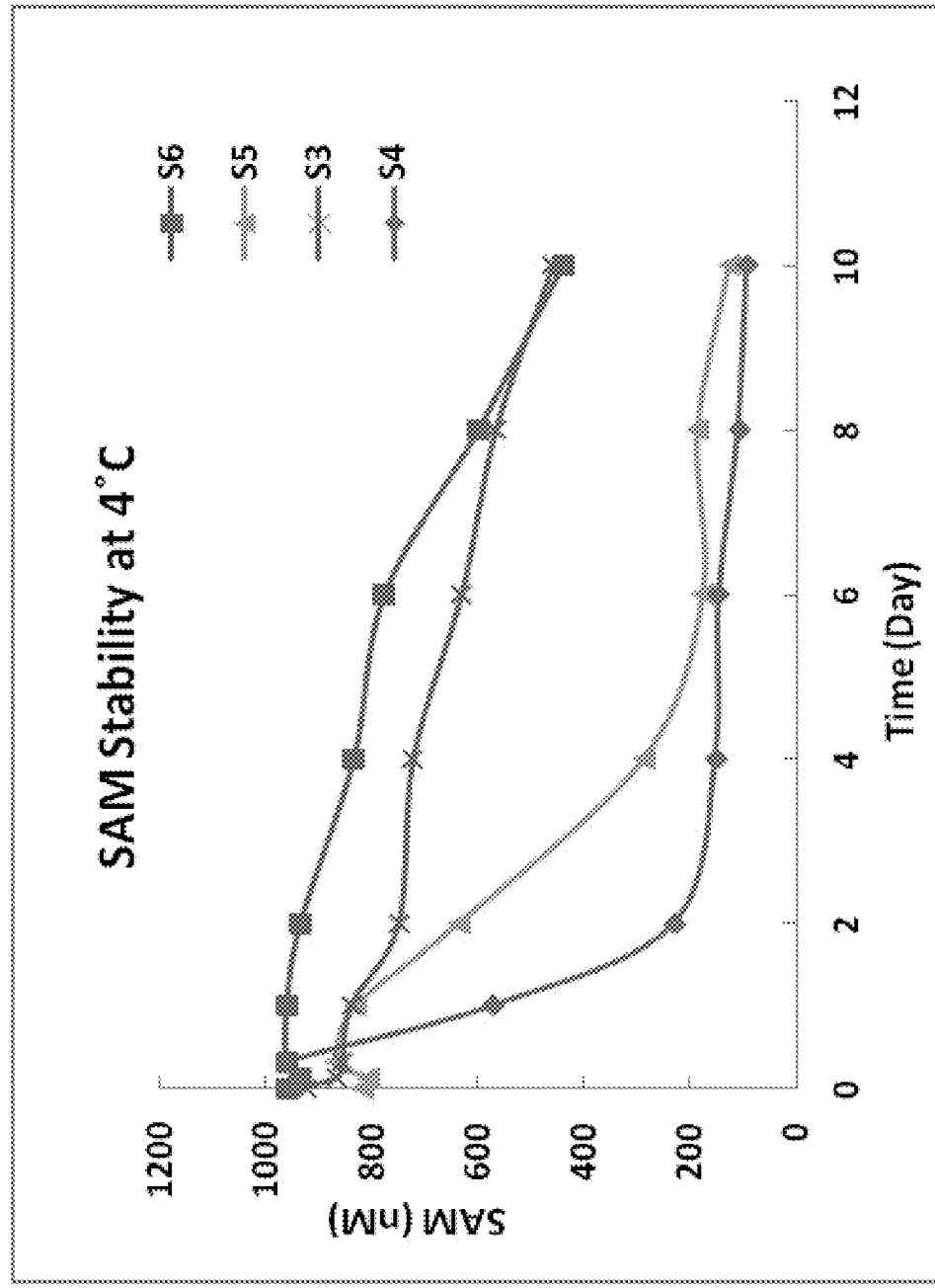
FIG. 19A shows the SAM level for plasma samples from 4 normal volunteers stored at 4° C. over 10 days. The SAM level varied among individuals.
Figure 19B:
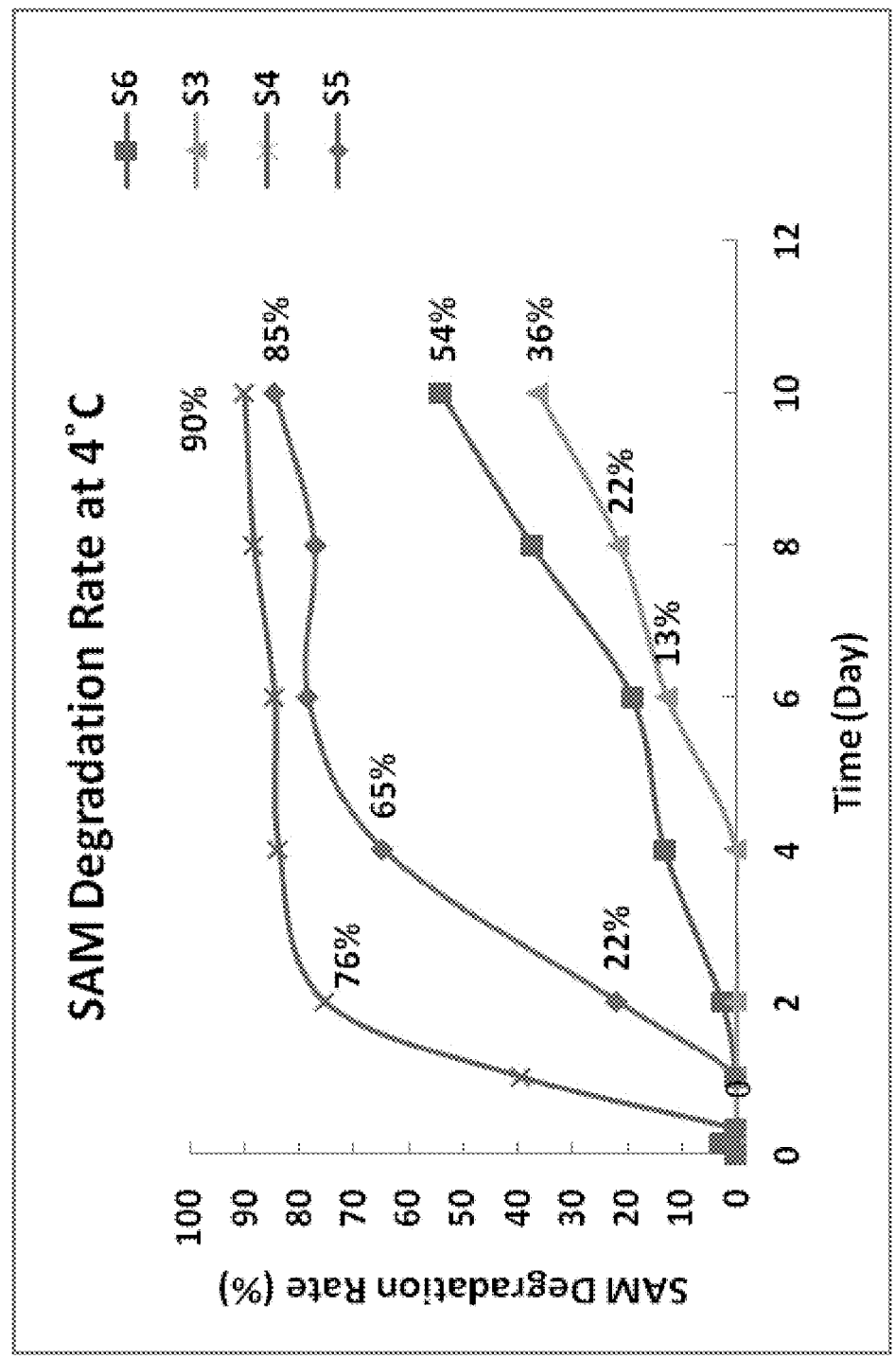
FIG. 19B describes the percentage of SAM degradation of plasma samples from 4 normal volunteers stored at 5° C. over 10 days. SAM degradation varied among individuals.
Figure 19C:
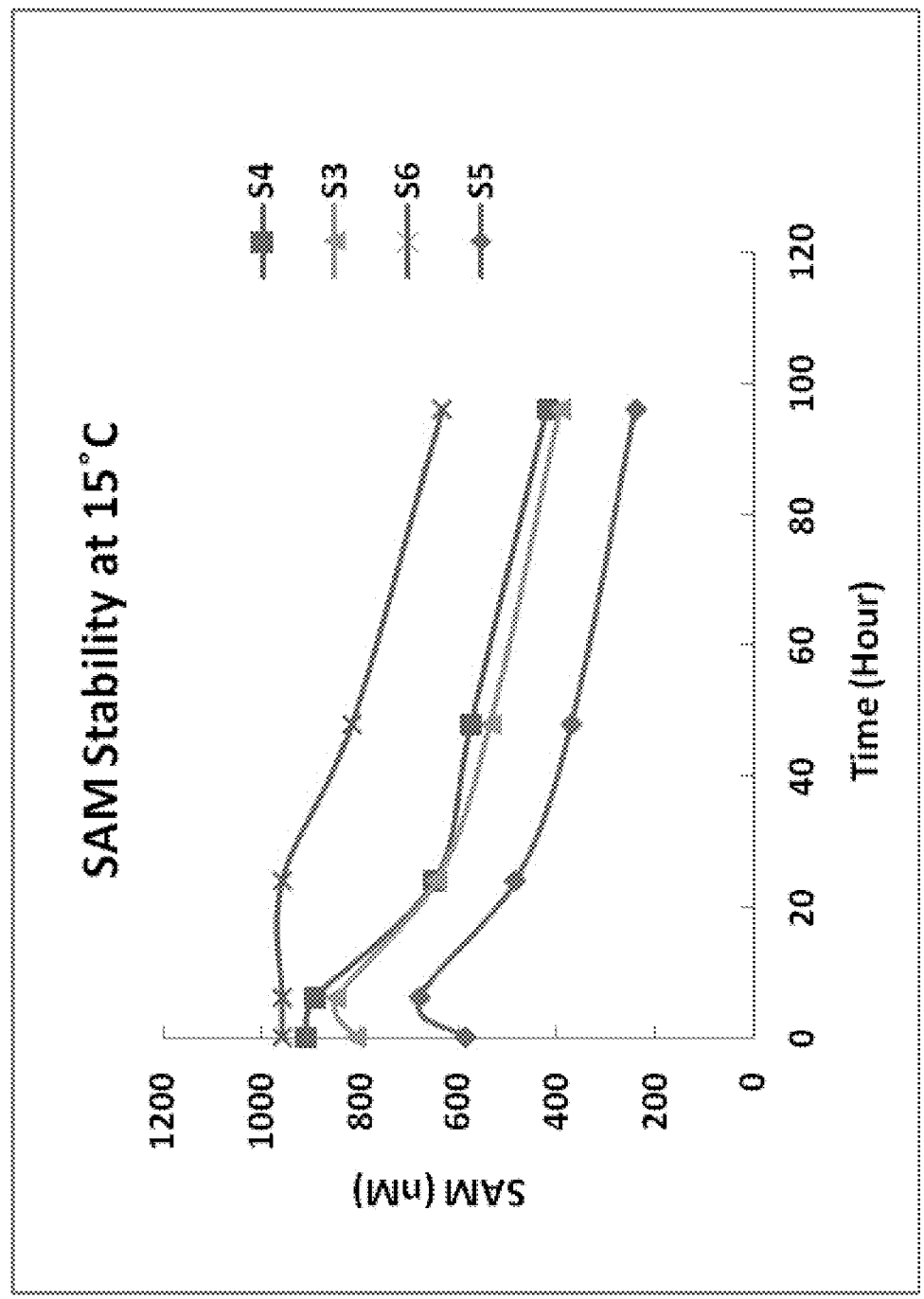
FIG. 19C illustrates the SAM level for plasma samples from 4 normal volunteers stored at 15° C. over 4 days. The SAM level varied among individuals. SAM levels were reduced faster compared to the samples stored at 4° C.
Figure 19D:
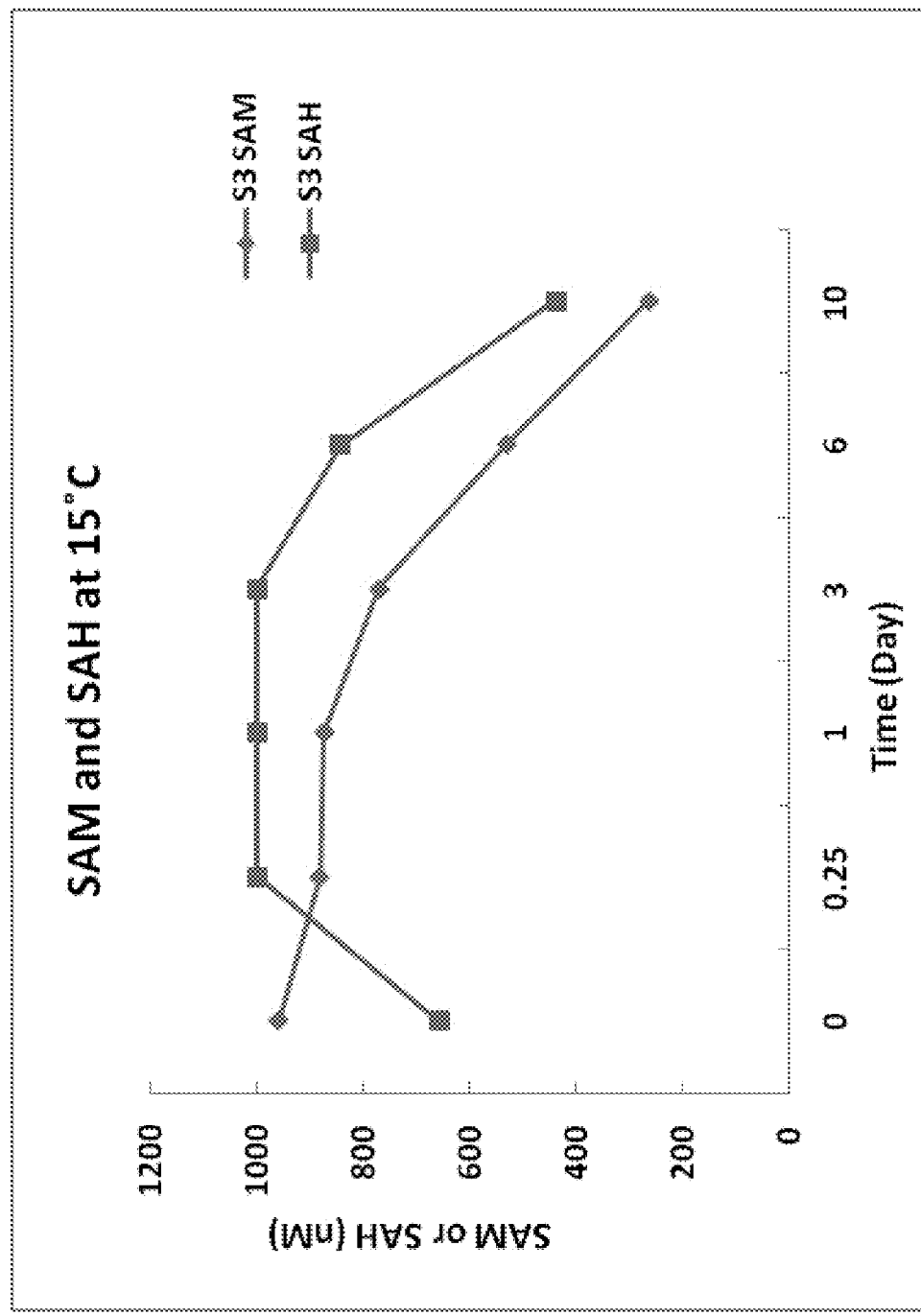
FIG. 19D shows the SAM and SAH levels at 15° C. over 10 days. Within 6 hours, SAM was decreased while SAH was increased to more than 1000 nM. After about 3 days, both SAM and SAH started decreased fairly quickly.
Figure 19E:
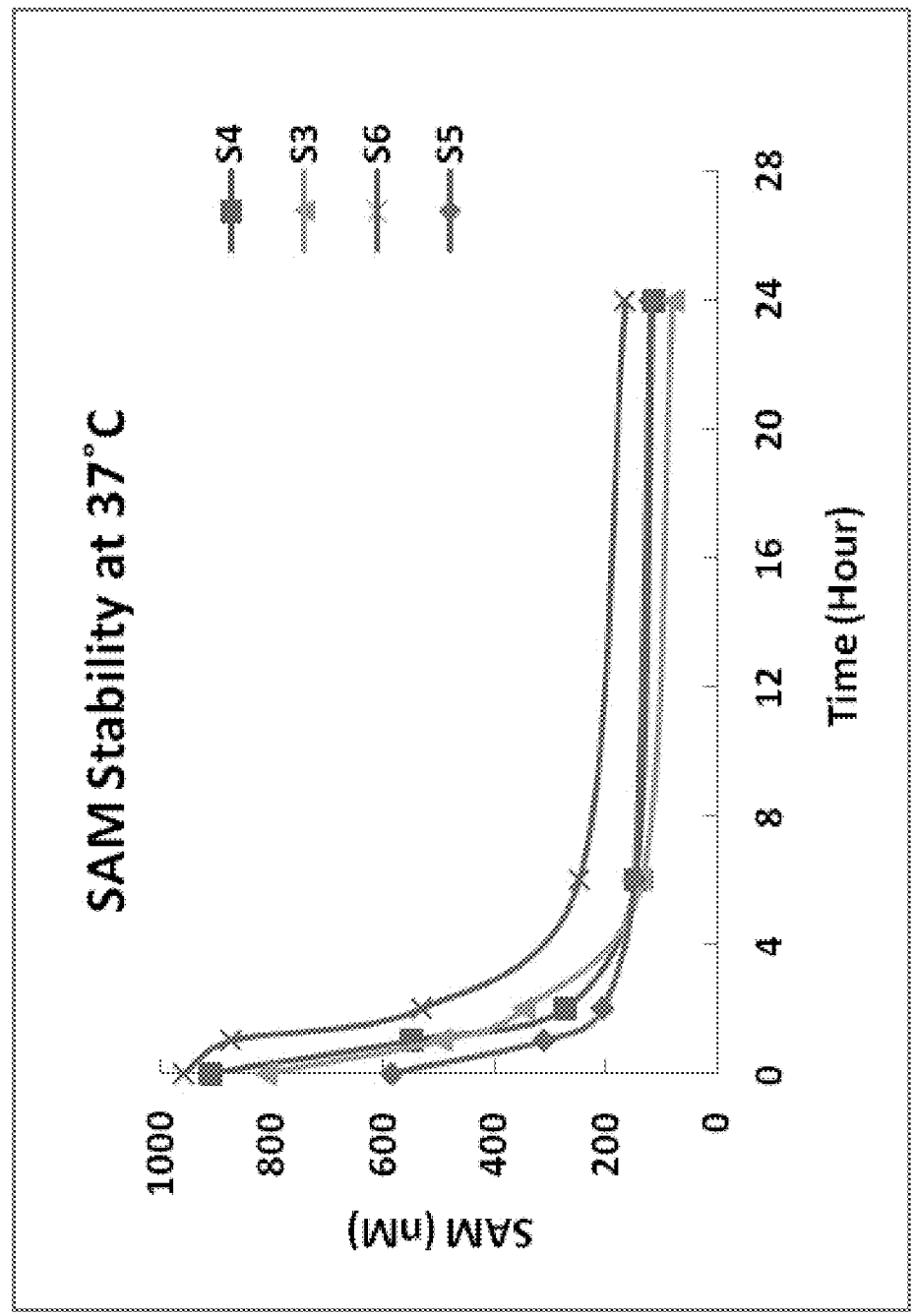
FIG. 19E relates to the stability of SAM at 37° C. SAM was reduced quickly in all samples.
Figure 19F:
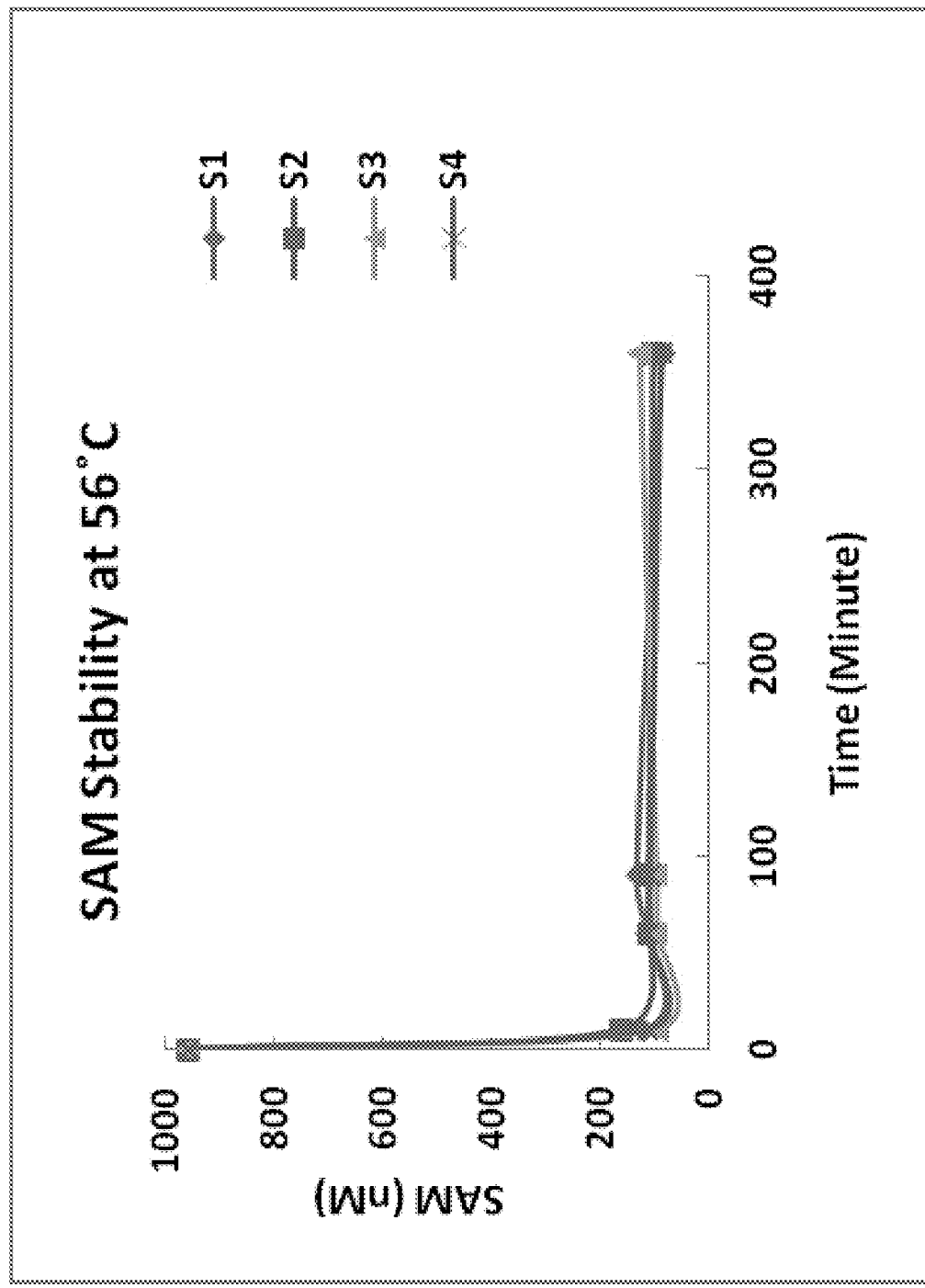
FIG. 19F illustrates the stability of SAM at 56° C. SAM was reduced even faster than at 37° C. in all samples.
Figure 19G:
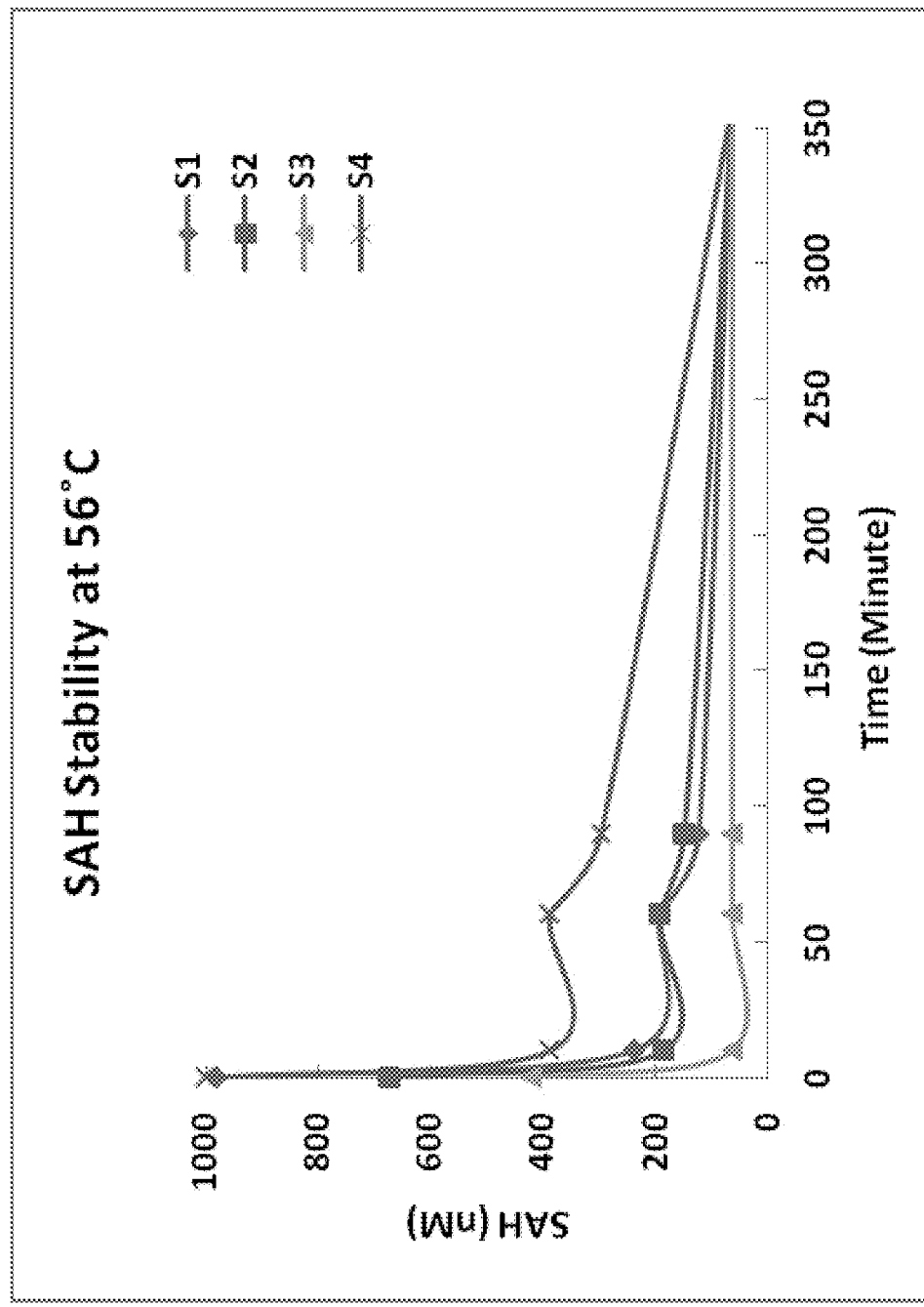
FIG. 19G describes the stability of SAH at 56° C. SAH was first reduced quickly and then slightly increased around 1 hour, followed by further decrease.

The chemical processes and dynamics of SAM and what forms in human plasma are not clear. It is possible that SAM exists as both free molecule and in association with other bio-molecules. The results of immunoassays reveal both free and binding forms of SAM in plasma. The thermal stability of free and binding forms of SAM could be different, and each individual may have different portions of free or combine/conjugated form, which partially explains why SAM from some samples persisted relatively longer at 4° C. than that from other participants (FIG. 19A). The study on the stability as measured by the direct competitive ELISA indicated variation among participants. We do not know which form of SAM or SAH is more stable than the other form. Other possibility, e.g. certain partially degraded SAM may also be able to bind mouse anti-SAH antibody. Further investigated is needed to clarify this.

To distinguish whether there are conjugated form of SAM and SAH in human plasma, we used dialysis bags to dialyze plasma samples at different temperature for 24 hours with at least two changes of dialyzing buffer (20 mM PB, pH7.4), then measured the SAM and SAH levels before and after dialysis.

Figure 20A:
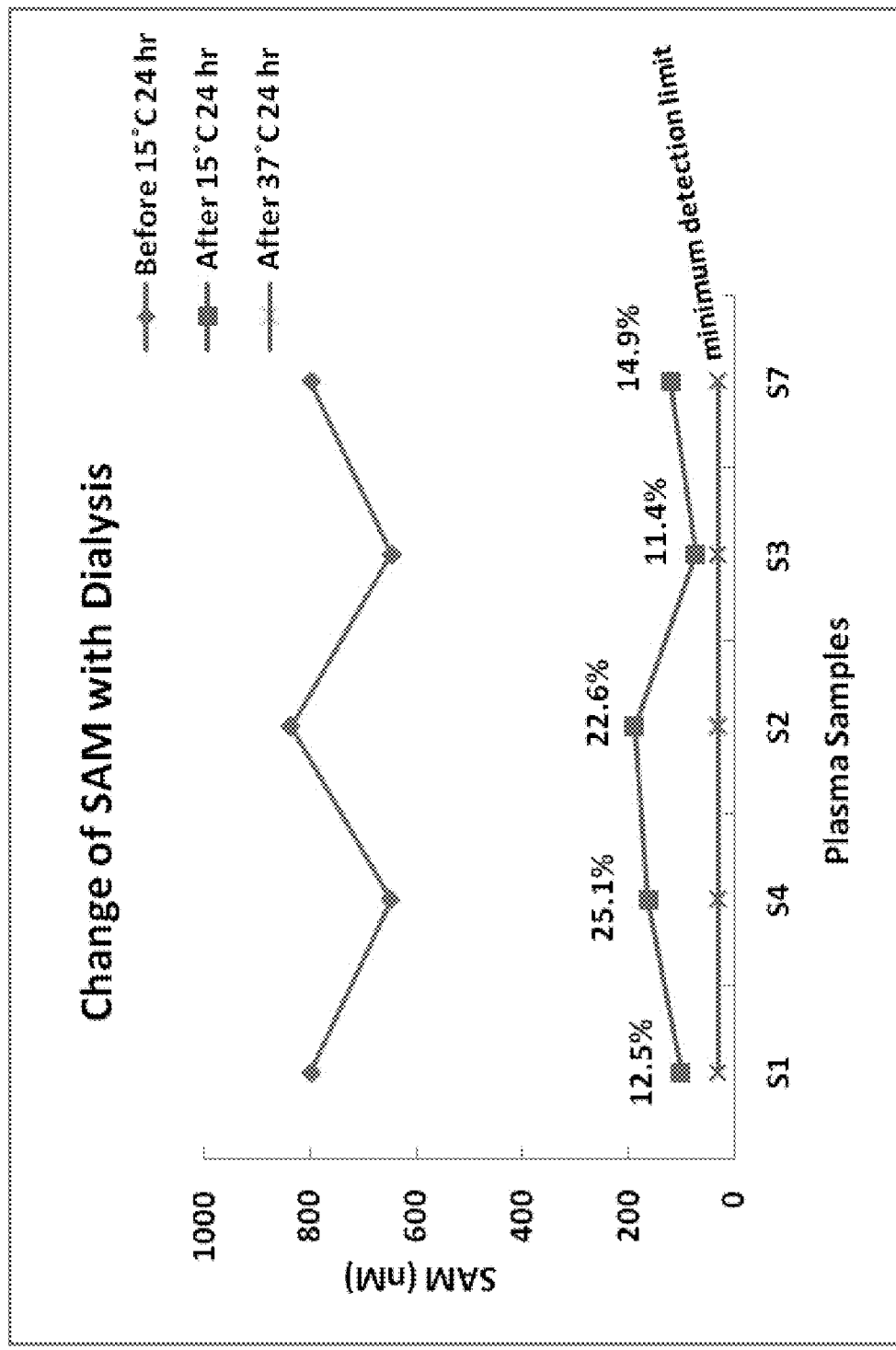
FIG. 20A illustrates that SAM level was significantly reduced after dialysis with 20 mM phosphate buffer, pH 7.4. The curve for 37° C. dialysis for 24 hours showed the minimum detection value of 30 nM, which should be considered as trial or no SAM left.
Figure 20B:
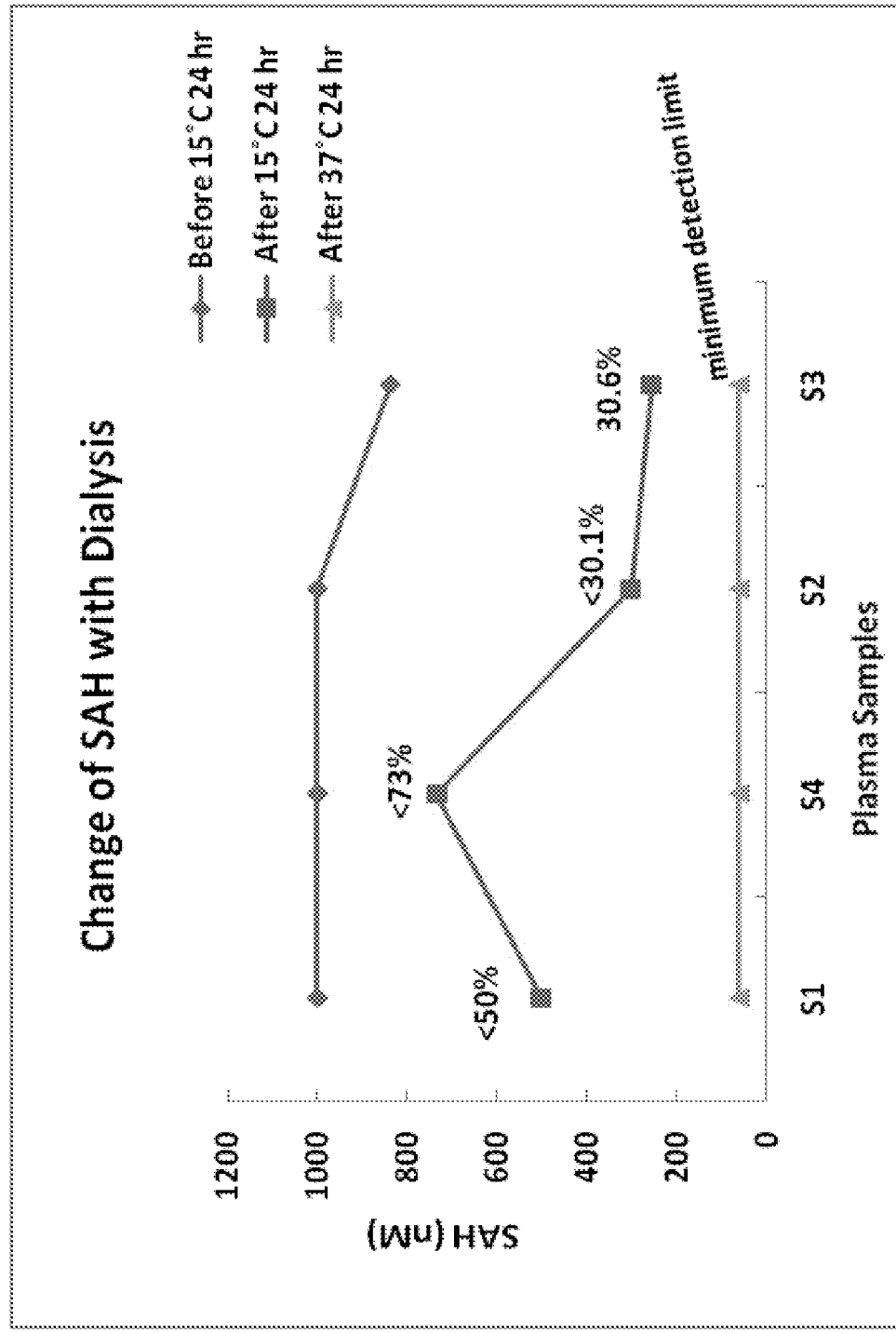
FIG. 20B shows that SAH level was significantly after dialysis with 20 mM phosphate buffer, pH 7.4. The curve for 37° C. dialysis for 24 hours showed the minimum detection value of 62.5 nM, which should be considered as trivial or no SAH left.

FIGS. 20A and 20B shows that SAM and SAH were all detected at reduced levels after dialysis compared to the controls without dialysis. Notice that for those SAH data which were greater than or equal to 1000 nM, only 1000 nM was used in the figure. Therefore, it is obvious that the immunoassays used in this invention can bind free SAM and SAH from human plasma. The differences of SAM or SAH as measured before and after dialysis (20 mM phosphate buffer, pH 7.4) for each sample represented the free SAM or SAH molecules that escaped from the dialysis bag (MW 14,000, Biosharp, USA) into the dialysis buffer, therefore they could not be detected from the sample collected from dialysis bag.

FIGS. 20A and 20B also show the percentages of SAM and SAH that were left within the dialysis bag after dialysis at 15° C. for 24 hours, which represented the amount of non-free SAM and SAH respectively. This observation indicated that the non-free form of SAM was 11-25% and non-free form (conjugated with proteins bigger than 14,000 Dalton) of SAH was around 30%. The lines at the bottoms of FIG. 20A and FIG. 20B showed the minimum detection limit, whereas the values should be less than the minimum detection limits and should be considered trivial or no SAM and SAH left after being exposed to 37° C. for 24 hour.

As we know each individual has very different metabolite profile from others. Many factors including genome, neuroendocrine, environment, health factors play roles in the outcomes of blood tests. Each individual has his or her unique fluid environment, for example pH, electrolyte, blood viscosity, plasma normal and abnormal components such as drugs, etc. This may partially explain why SAM and SAH from each individual have different degrees of thermal stability. For example, an individual with high pH plasma may show an increased SAM and SAH degradation rate than another individual who has a relatively lower pH plasma environment.

Example 22

Stability of SAM and SAH at Different pH Values

The stability of SAM and SAH was also tested in acidic and basic conditions at 15° C. Normal mixed plasma sample (S8) (with pH 7.84), samples S1, S2, S3, S4 (pH 7.0-7.5) were used in the experiments. 10 µl 5M HCl was added to 1260 µl plasma to adjust its pH to 5.5-6.0. In another set of samples, 2 µl 5M NaOH was added to 1260 µl plasma to adjust its pH to 8.0-8.5. Before using these acidic or basic samples to conduct the immunoassay, 1.1 µl 5M NaOH was added to 180 µl acidic samples; 0.376 µl 5M HCl was added to 180 µl basic samples to make them neutral. Meanwhile, standards were also added the same amount of acid and base as the samples. All samples have the same trend, FIGS. 21A and 21B only showed the dynamic SAM and SAH with pH from one sample S2.

Figure 21A:
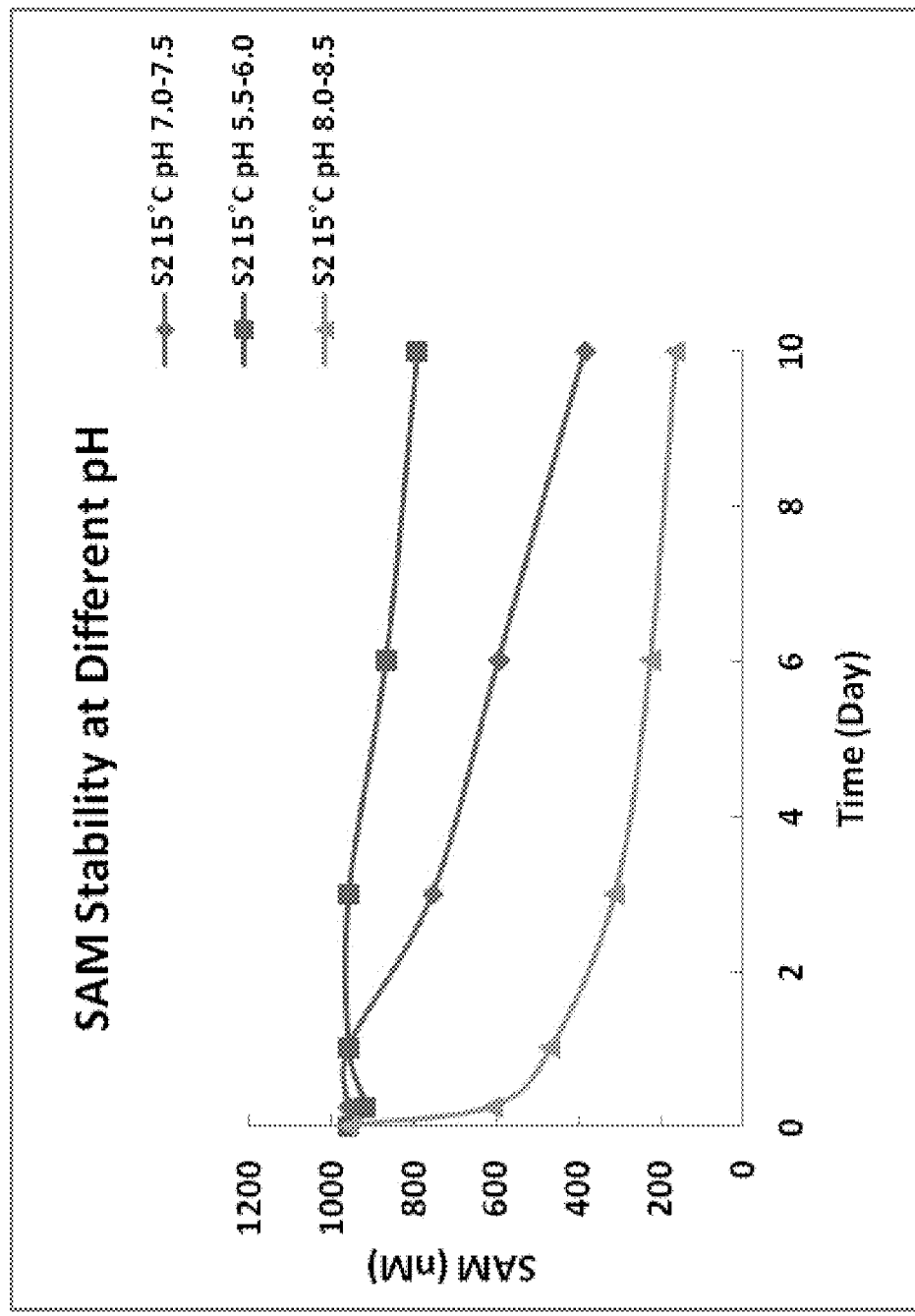
FIG. 21A relates to the stability of SAM at different pH. Low pH (acidic environment) helped prevent SAM from quick degradation. Basic environment speeded up SAM degradation.
Figure 21B:
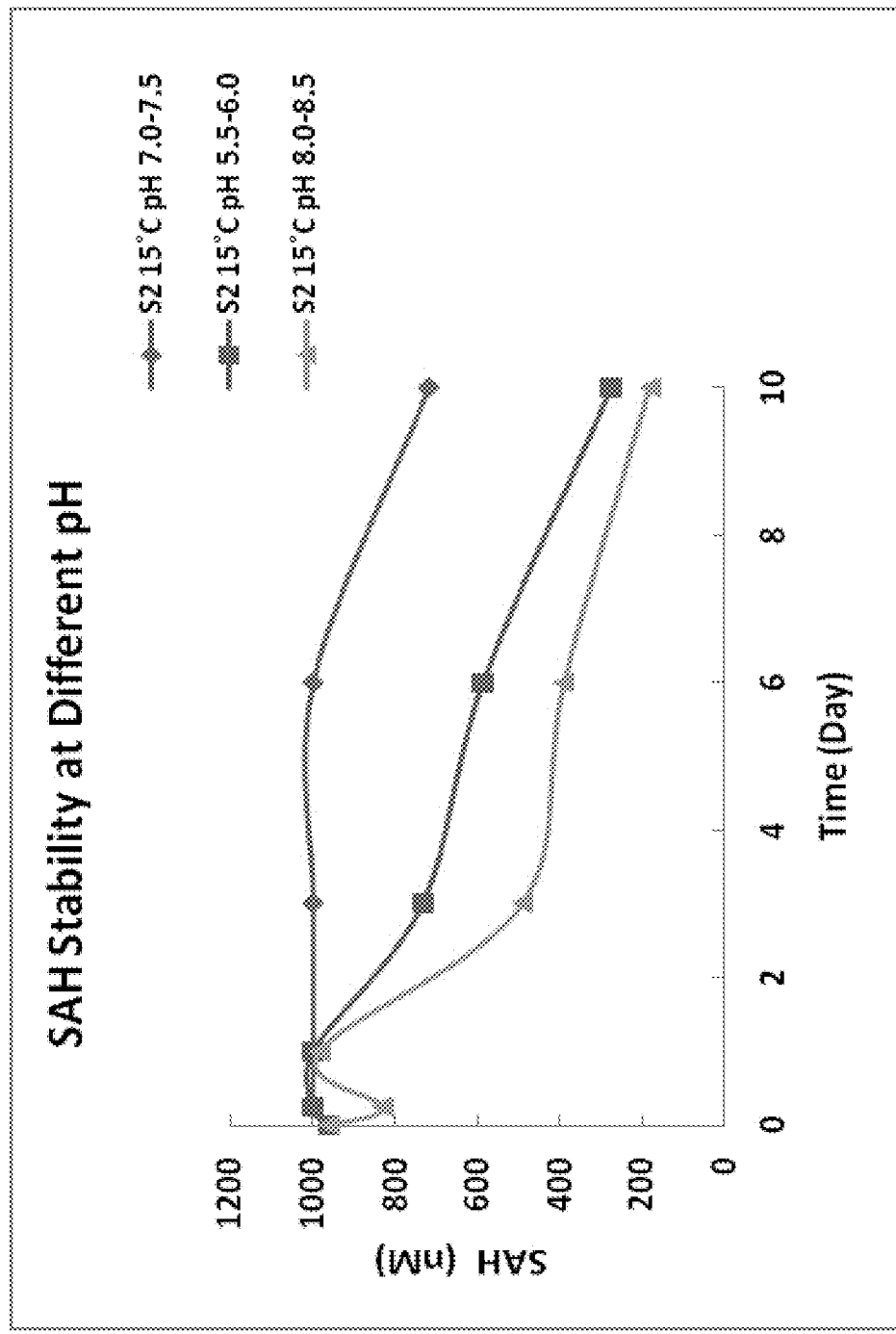
FIG. 21B shows the stability of SAH at different pH. Both acid and base increased the speed SAH was degraded. Notice the SAH values at 1 day time point could be higher than 1000 nM. The experiment only showed the maximum detection limit of 1000 nM, which caused the SAH spikes not shown for pH 7.0-7.5 and pH 5.5-6.0 curves.

In FIG. 21A, SAM shows degradation rate increased with pH values. This observation was consistent with a prior publication regarding pH stability of SAM (Parks, L W, et al. jbc.org Aug. 23, 1957). It indicated that acidic environment slowed down SAM degradation. FIG. 21B indicated both acidic and basic environment speeded up plasma SAH degradation. However basic environment has a stronger impact than acidic environment. The SAH data at 1 day time point, the SAH levels for pH 7.0-7.5 and pH 5.5-6.0 curves were measured to be greater than 1000 nM. The experiment has maximum detection limit as 1000 nM, only 1000 nM points were plotted, therefore the spikes at 1 day time point could not been see for pH 7.0-7.5 and pH 5.5-6.0 curves. This figure is meant to show the dynamics of SAH level for this particular sample. Difference among samples exists.

Example 23

Healthy Human Plasma SAM and MI as a Function of Gender and Age (Study #2)

Normal samples were strictly evaluated through series of examination and proven disease free. Normal human serum was collected and frozen within 2 hours with serum separator tubes or SSTs. Serum samples were stored frozen at −80° C. The samples were analyzed according to the immunoassays of the present invention.

TABLE 5

SAM Level and Methylation Index (MI) in Normal Subjects

| Case # | % of SAM > 240 nM | % of SAM > 120 nM | Avg. ± Stdev | % of MI > 2 | % of MI > 1 | % of MI < 0.5 |
|---|---|---|---|---|---|---|
| Male (41) | 56.09 | 90.24 | 340.51 ± 211.70 | 43.90 | 43.41 | 12.20 |
| Female (40) | 82.50 | 100 | 433.96 ± 213.02 | 52.50 | 72.50 | 5.00 |
| Total (81) | 69.14 | 95.06 | 386.66 ± 216.20 | 46.91 | 67.90 | 8.64 |

Table 5 shows that about 56.09% of males whose SAM levels were higher than 240 nM whereas 82.50% of females whose SAM levels were higher than 240 nM. Methylation Index (ratio of SAM and its de-methyl product S-adenosylhomocysteine, SAH) was also higher in females than in males. When methylation index was less than 0.5, it is considered as sub-health or disease condition. There are only 5% of female whose MI was less than 0.5 whereas there were 12.20% of males whose MI was less than 0.5. It is believed that SAM is a health indicator: the higher the SAM, the better the health status one could be at. SAH is just the opposite, the higher the SAH, the worse the health status one could be. Normal females have higher SAM level and methylation index than normal male individuals. How does this relate to the fact that females have a relatively longer lifespan and better disease-resistance capability, which remains to be further investigated.

Figure 22A:
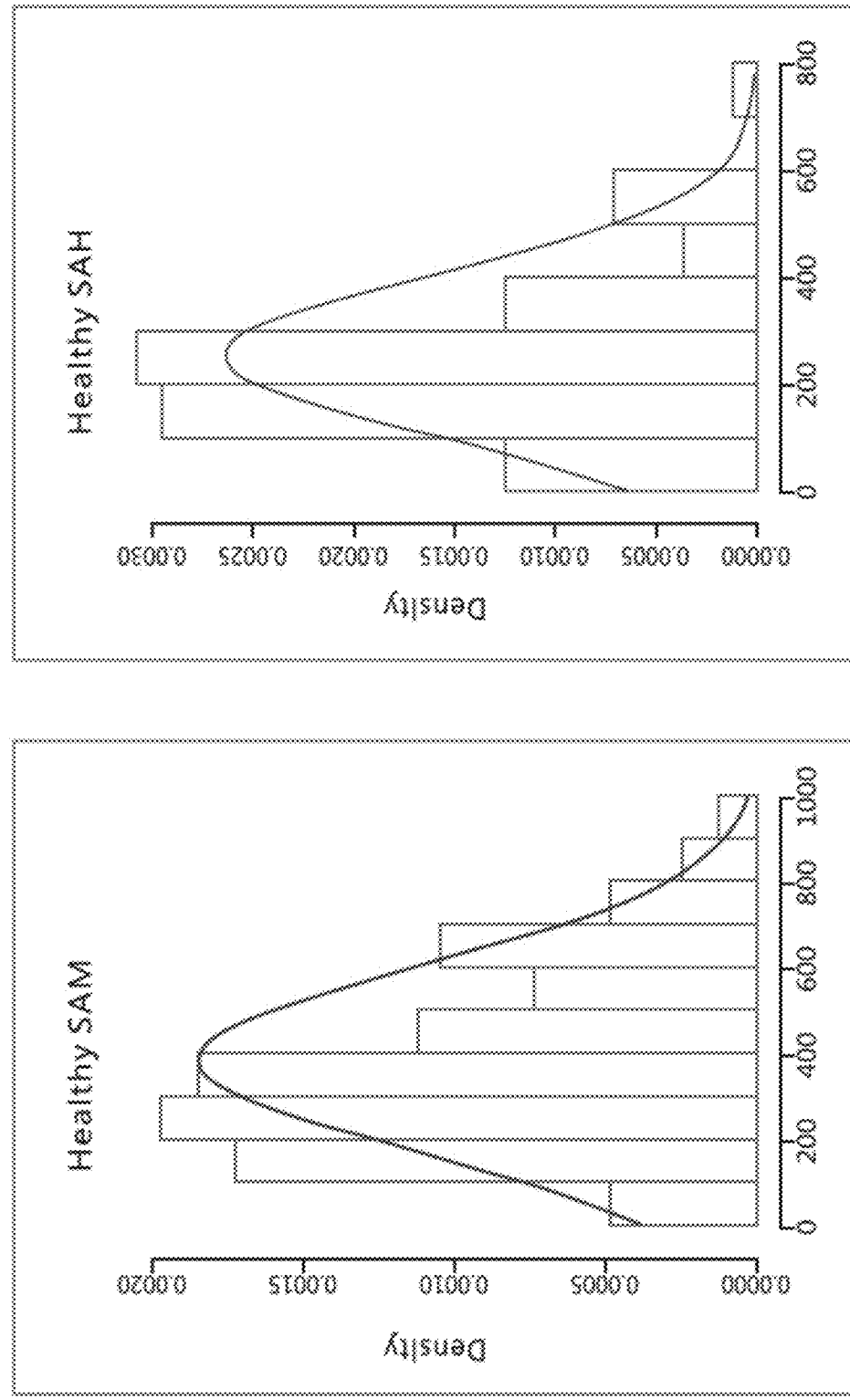
FIG. 22A shows the means and distributions of SAM and SAH levels from 81 normal serum samples. It fits a normal distribution (statistical analysis using R).
Figure 22B:
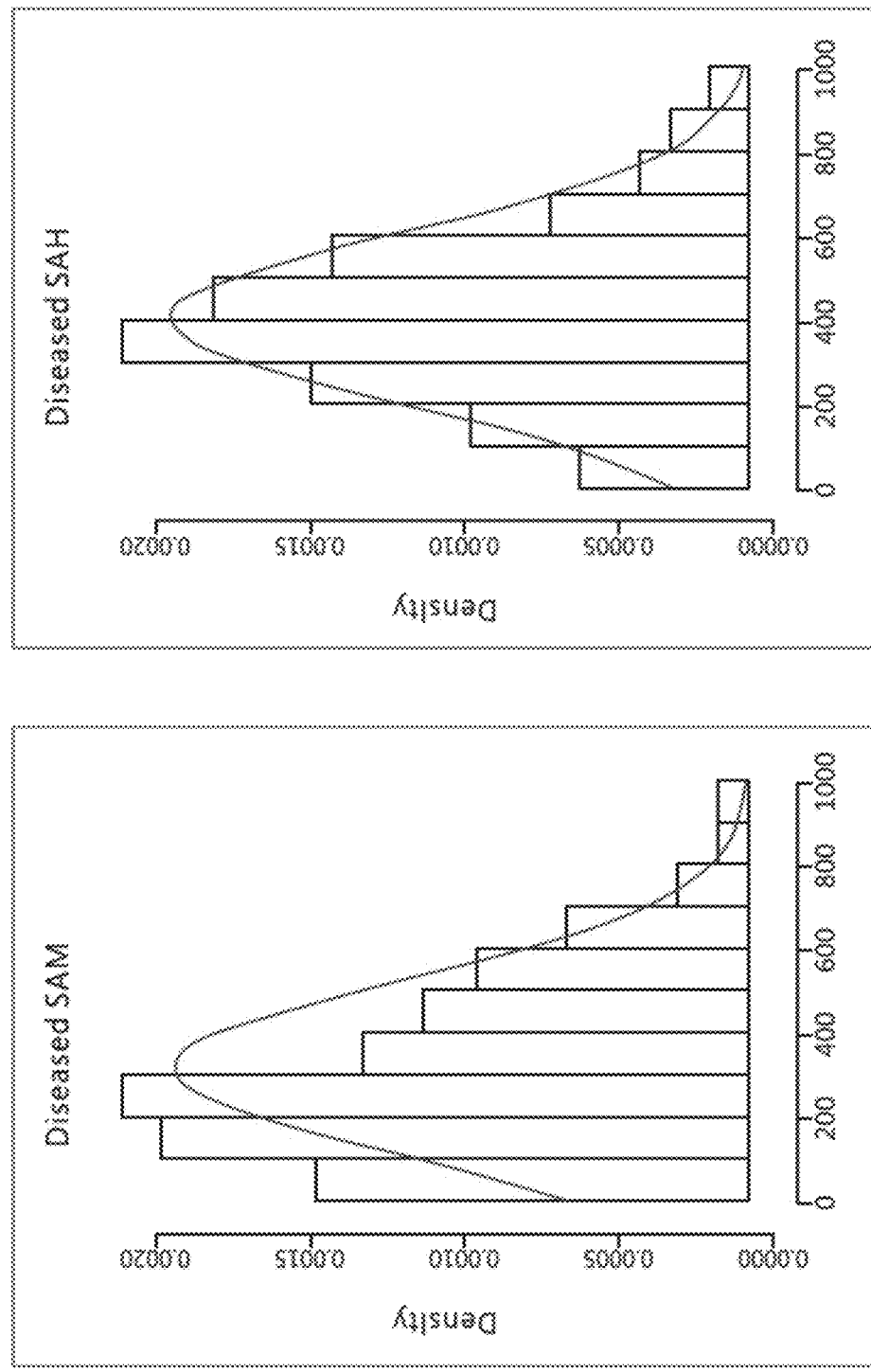
FIG. 22B shows the means and distributions of SAM and SAH levels from 291 diseased samples. It fits a normal distribution (statistical analysis using R).

Before performing any statistical analysis, we first examined whether data sets in our studies fit normal distribution. We used R to test the data distribution property and found the means and standard deviations of SAM, SAH and MI for healthy and diseased samples all fit normal distribution (FIG. 22A-22B).

Figure 23:
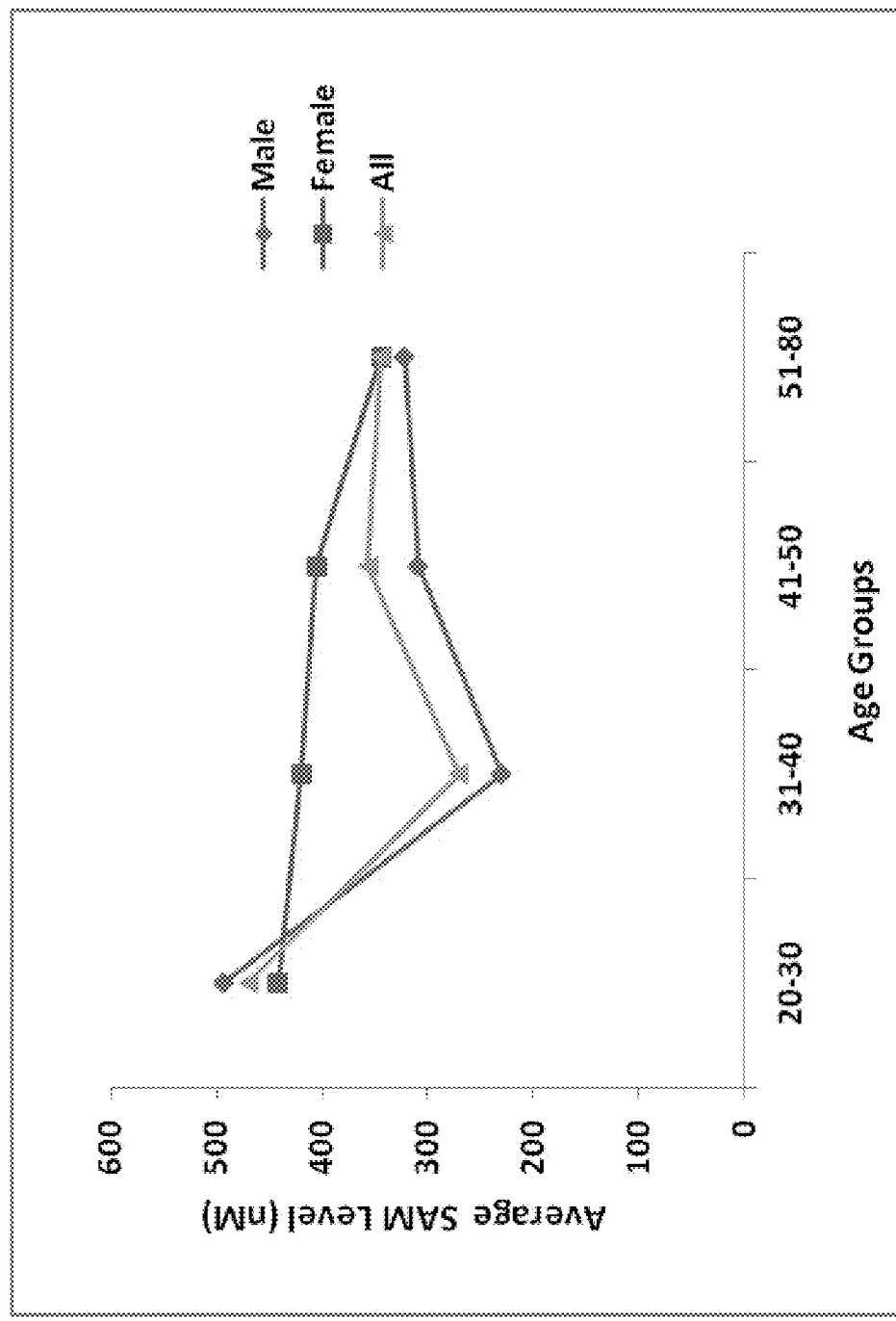
FIG. 23 describes normal SAM levels in different age groups and different gender groups (Data from Study #2).

FIG. 23 shows the average of SAM levels by age groups and genders. Statistical analysis with R was performed by Sydney Wong (We sincerely appreciate her contribution to the analysis for study #2)

TABLE 6A

ANOVA Results for Different Age and Gender

| Dataset | Response Variable | Explanatory Variable | p-value | Significance |
|---|---|---|---|---|
| Healthy | SAM | Age Group | 0.03437 | ** |
| Healthy | SAH | Age Group | 0.4964 | |
| Healthy | MI | Age Group | 0.1058 | |
| Healthy | SAM | Gender | 0.05115 | * |
| Healthy | SAH | Gender | 0.584 | |
| Healthy | MI | Gender | 0.8752 | |

Note:
* represents significance at significance level α = 0.1.
** represents significance at significance level α = 0.05.
*** represents significance at significance level α = 0.01.
**** represents significance at significance level α = 0.001.

Based on the ANOVA table, we see that Age Group is a significant factor with respect to SAM levels in healthy patients. So we will do pairwise t-tests for each pair of levels of Age Group.

TABLE 6B

ANOVA Results for Pairwise Age Comparisons

| Age Group 1 | Age Group 2 | p-value | Significance |
|---|---|---|---|
| 20-30 | 31-40 | 0.01728 | ** |
| 20-30 | 41-50 | 0.03793 | ** |
| 20-30 | 51-80 | 0.00568 | *** |
| 31-40 | 41-50 | 0.7461 | |
| 31-40 | 51-80 | 0.7815 | |
| 41-50 | 51-80 | 0.9081 | |

So clearly, by the pairwise t-test results, the SAM levels for the healthy patients aged 20-30 are statistically significant from those of the other age groups. And, looking at the plot, of mean SAM levels of healthy patients by Age Group, we see that the SAM levels of healthy patients aged 20-30 are significantly higher than those of the other age groups.

After doing a pairwise t-test for SAM levels of healthy patients by gender, we get a p-value of 0.05117 which is statistically significant at an α=0.1 level. The mean of the female SAM levels is 433.96 and the mean of the male SAM level is 340.51, which means the SAM levels for healthy females are significantly higher than those of healthy males.

Example 24

SAM and MI in Blood Center Plasma and Diseased Plasma (Study #3)

310 cases of normal plasma samples were frozen at −20° C. within 3-10 hours with EDTA as anticoagulants and analyzed using the immunoassays of the present invention. The study was done with normal samples after excluding existence of infectious diseases such as virus hepatitis, HIV infection, Syphilis, Gonorrhea from a blood center with blood donors between 18-60 years old.

TABLE 7A

Disease Case Information in Study #3

| | |
|---|---|
| Cerebrovascular diseases + Parkinson's Disease | 45 + 3 |
| Diabetes | 43 |
| HBP | 22 |
| Heart diseases | 51 |
| Inflammation | 35 |
| Kidney disease + Diabetes Kidney disease | 24 + 2 |
| Liver diseases | 30 |
| Pulmonary diseases | 36 |

TABLE 7B

Cancer Case Information in Study #3

| | |
|---|---|
| Bladder Cancer | 2 |
| Breast Cancer | 3 |
| Colon Cancer | 16 |
| Esophagus Cancer | 3 |
| Gallbladder Cancer | 1 |
| Lipoma | 2 |
| Liver Cancer | 23 |
| Lung Cancer | 75 |
| Lymphoma | 2 |
| Multiple Myeloma | 1 |
| Ovary Cancer | 2 |
| Prostate Cancer | 5 |
| Throat Cancer | 4 |
| Thymoma | 1 |
| Thyroid cancer | 1 |
| Uterus Cancer | 5 |
| Vascular Cancer | 1 |
| Cancer | 27 |

TABLE 7C

Brain Disease Information in Study

| | |
|---|---|
| Cerebrovascular diseases | 20 |
| Depression | 10 |
| Parkinson's Disease | 10 |

TABLE 8

Distribution of Normal Human Plasma SAM Levels in Females and Males

| | Male | | Female | |
|---|---|---|---|---|
| SAM (nM) | No. | % | No. | % |
| <30 | 0 | 0 | 1 | 1.01 |
| 30-60 | 9 | 4.27 | 3 | 3.03 |
| 60-120 | 44 | 20.85 | 9 | 9.09 |
| 120-240 | 70 | 33.18 | 33 | 33.33 |
| 240-480 | 75 | 35.55 | 39 | 39.39 |
| 480-960 | 13 | 6.16 | 14 | 14.14 |
| >960 | 0 | 0 | 0 | 0 |
| Avg. SAM | 211 | 232.86 | 99 | 296.92 |
| Stdev. SAM | 211 | 149.56 | 99 | 185.12 |

TABLE 9

Distribution of Normal Human Plasma SAM Levels in Different Age Groups

| | Age 18-30 | | Age 31-40 | | Age 41-50 | | Age 51-60 | |
|---|---|---|---|---|---|---|---|---|
| SAM (nM) | No. | % | No. | % | No. | % | No. | % |
| <30 | 1 | 0.73 | 0 | 0 | 0 | 0 | 0 | 0. |
| 30-60 | 1 | 0.73 | 5 | 6.10 | 4 | 5.33 | 2 | 12.50 |
| 60-120 | 17 | 12.41 | 16 | 19.51 | 17 | 22.67 | 3 | 18.75 |
| 120-240 | 42 | 30.66 | 28 | 34.15 | 30 | 40.00 | 3 | 18.75 |
| 240-480 | 58 | 42.34 | 28 | 34.15 | 20 | 26.67 | 8 | 50.00 |
| 480-960 | 18 | 13.14 | 5 | 6.10 | 4 | 5.33 | 0 | 0 |
| >960 | 0 | 0 | 0 | 0 | 0 | 0 | 0 | 0 |
| <60 | 2 | 1.46 | 5 | 6.10 | 4 | 5.33 | 2 | 12.5 |
| >240 | 76 | 55.47 | 33 | 40.25 | 24 | 32 | 8 | 50 |
| Total No. | 137 | | 82 | | 75 | | 16 | |

TABLE 10

Normal Human Plasma SAM Levels in Age Groups and Genders

| Age Group | Gender | Average | Standard deviation |
|---|---|---|---|
| Age 18-30 | Male | 255.55 | 144.44 |
| | Female | 360.39 | 206.59 |
| | All | 290.75 | 174.34 |
| Age 31-40 | Male | 237.91 | 173.28 |
| | Female | 256.46 | 148.63 |
| | All | 242.66 | 166.62 |
| Age 41-50 | Male | 196.30 | 126.92 |
| | Female | 234.11 | 156.75 |
| | All | 208.40 | 137.24 |
| Age 51-60 | Male | 169.42 | 95.86 |
| | Female | 226.61 | 104.93 |
| | All | 198.01 | 101.48 |

Figure 24:
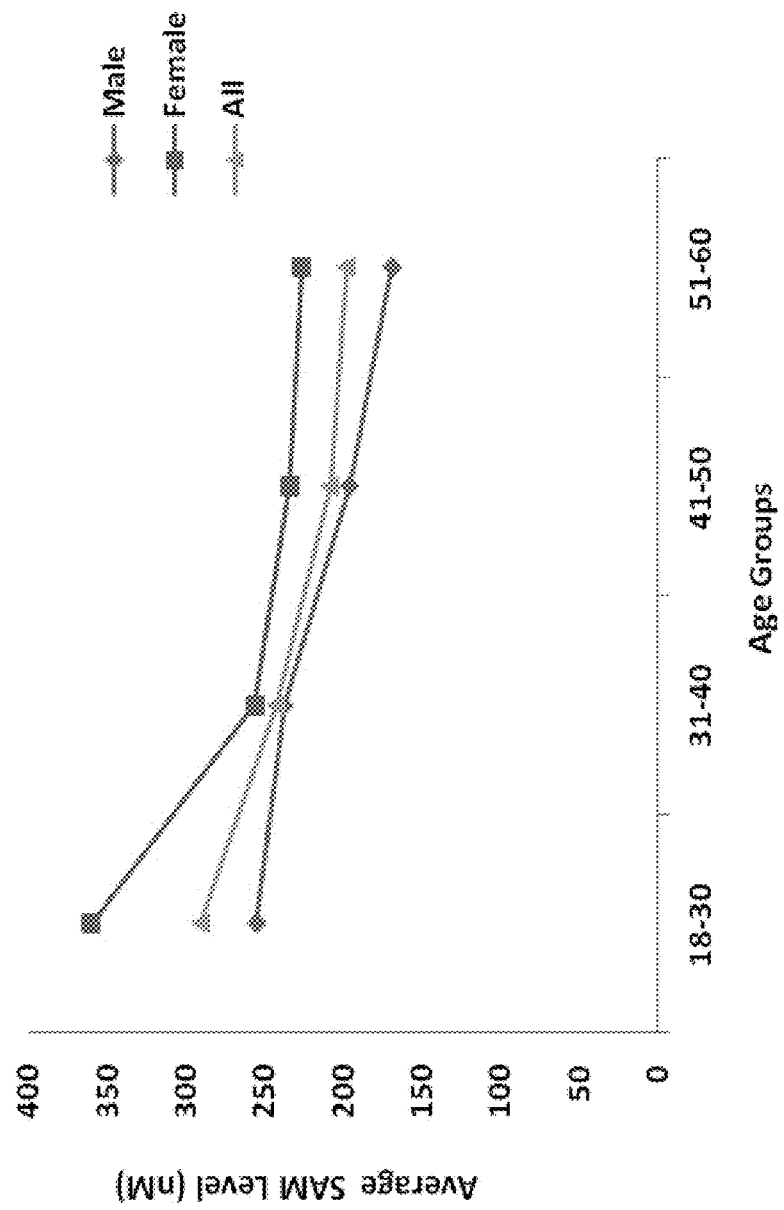
FIG. 24 illustrates normal SAM levels in different age groups and different gender groups (data from Study #3). Women in all age groups were detected with higher SAM levels in plasma than men. Average SAM levels decrease with age.

FIG. 24 also shows that on the average women had higher SAM level (296.92 nM) than men (232.86 nM) (see Table 8), which was about 28% higher. This was hardly because of the diet factor as we believed men and women had the same diet in the same culture, same geographical location and with the same social status. There must be some fundamental reasons that warranted the consistent difference observed here. This was likely related to the metabolism and genetic reasons, which remained to be further discovered.

SAM levels in female were higher than in males, which was consistent with previous Study #2. FIG. 24 showed the average SAM levels in different age groups and gender groups. SAM levels continuously going down as ages go up, men or women. This indicated SAM might be involved in aging process. From Table 8, we could see higher percentage of people older than 51 years old have SAM level less than 60 nM, indicating as people get older, SAM level is decreased. Table 10 showed as the age increased, the percentage of people who had decreased SAM level increased.

Patient samples were collected from clinical labs with no further information about disease condition, status and treatment. Samples were handled similarly to the samples described in Study #3. Statistical analysis with R was performed by Dr. Huaitian Liu (We sincerely appreciate his contribution to the analysis for Examples 24, 25 and 26)

Table 11 shows t-test results by comparing 81 cases of normal case from Example 23 with the diseases in Table 7A, which included kidney diseases (Renal cysts, kidney stones, hydronephrosis, cancer), liver diseases (hepatitis, cirrhosis) and diabetes were more significant than pulmonary diseases (chronic obstructive pulmonary emphysema, cancer, pneumonia, TB), cardiovascular & cerebrovascular diseases (coronary atherosclerotic heart disease, hypertension, Cerebrovascular diseases, embolism, lower extremity atherosclerosis obliterans), inflammation (gastrointestinal diseases, ulcer, intestinal obstruction, asthma, ureteral stones, prostate benign, ulterus benign, nasopharyngeal and breast diseases, blood system disorders, hernia, etc.).

TABLE 11

Results of t-test in Diseases from Table 7A

| Response Variable | Mean | p-value | Significance |
|---|---|---|---|
| SAM(Cerebrovascular diseases) | 357.9406 | 0.4365 | |
| SAH(Cerebrovascular diseases) | 353.175 | 0.001237 | *** |
| MI(Cerebrovascular diseases) | 1.148035 | 2.31E−05 | **** |
| SAM(Diabetes) | 262.3474 | 0.001136 | *** |
| SAH(Diabetes) | 372.0686 | 0.003831 | *** |
| MI(Diabetes) | 0.8619158 | 9.20E−08 | **** |
| SAM(HBP) | 288.3645 | 0.0389 | ** |
| SAH(HBP) | 358.1118 | 0.01378 | ** |
| MI(HBP) | 0.9178064 | 3.93E−07 | **** |
| SAM(Heart diseases) | 315.962 | 0.07938 | ** |
| SAH(Heart diseases) | 440.9451 | 5.95E−07 | **** |
| MI(Heart diseases) | 0.7822701 | 5.61E−09 | **** |
| SAM(Inflammation) | 223.732 | 3.05E−06 | **** |
| SAH(Inflammation) | 292.012 | 0.2051 | |
| MI(Inflammation) | 0.8193137 | 1.91E−08 | **** |
| SAM(Kidney disease) | 307.6073 | 0.1077 | |
| SAH(Kidney disease) | 497.1204 | 7.76E−06 | **** |
| MI(Kidney disease) | 0.6976807 | 3.69E−09 | **** |
| SAM(Liver diseases) | 356.3407 | 0.5037 | |
| SAH(Liver diseases) | 444.0027 | 1.22E−06 | **** |
| MI(Liver diseases) | 0.8921861 | 2.72E−07 | **** |
| SAM(Pulmonary diseases) | 393.3392 | 0.8827 | |
| SAH(Pulmonary diseases) | 486.5144 | 4.24E−08 | **** |
| MI(Pulmonary diseases) | 0.7916811 | 5.27E−09 | **** |

As can be seen from Table 11, in all diseases, MI was significantly reduced. In the case of inflammation, SAM was significantly reduced and SAH change was not significant. In cerebrovascular, liver, kidney and pulmonary disease, SAM changes were not significant but SAH was significantly increased.

TABLE 12A

Results of t-test in Cancers from Table 7B

| Response Variable | Mean | p-value | Significance |
|---|---|---|---|
| SAM(Liver Cancer) | 278.0652 | 0.03451 | ** |
| SAH(Liver Cancer) | 293.35 | 0.3288 | |
| MI(Liver Cancer) | 1.562109 | 0.1131 | |
| SAM(Lung Cancer) | 262.5039 | 0.001248 | *** |
| SAH(Lung Cancer) | 326.9877 | 0.007807 | *** |
| MI(Lung Cancer) | 0.9710702 | 3.67E−06 | **** |
| SAM(Other Cancer) | 283.3233 | 0.00116 | *** |
| SAH(Other Cancer) | 394.7301 | 5.61E−06 | **** |
| MI(Other Cancer) | 0.8156412 | 8.12E−09 | **** |

We regrouped cancer cases from Table 7B into three cancer groups (liver cancer 23 samples, lung cancer 75 samples, other cancers 76 samples). As can be seen from Table 12, except for liver cancer samples, the results from other cancer samples indicated that SAM and MI was significantly reduced and SAH was significantly increased. As we had no further information about the 23 cancer patients, it is very likely that the patients were given SAM treatment as it is a routine to supplement SAM pills to patients with liver disorders upon hospitalized. Otherwise, the SAM levels could be lower. Therefore, MI would be significantly lowered as in the case of other cancers.

TABLE 12B

Results of ANOVA in Cancers from Table 7B

| Dataset | Response Variable | Explanatory Variable | p-value | Significance |
|---|---|---|---|---|
| Liver Cancer | SAM | Age Group | 0.4718 | |
| Liver Cancer | SAH | Age Group | 0.0974 | * |
| Liver Cancer | MI | Age Group | 0.007917 | *** |
| Liver Cancer | SAM | Gender | NA (all males) | NA |
| Liver Cancer | SAH | Gender | NA | NA |
| Liver Cancer | MI | Gender | NA | NA |
| Lung Cancer | SAM | Age Group | 0.009508 | *** |
| Lung Cancer | SAH | Age Group | 0.005919 | *** |
| Lung Cancer | MI | Age Group | 0.08754 | * |
| Lung Cancer | SAM | Gender | 0.07647 | * |
| Lung Cancer | SAH | Gender | 0.6086 | |
| Lung Cancer | MI | Gender | 0.0001109 | **** |
| Other Cancer | SAM | Age Group | 0.06088 | * |
| Other Cancer | SAH | Age Group | 0.05491 | * |
| Other Cancer | MI | Age Group | 0.5193 | |
| Other Cancer | SAM | Gender | 0.2516 | |
| Other Cancer | SAH | Gender | 0.8028 | |
| Other Cancer | MI | Gender | 0.4848 | |

Table 12B showed the results of ANOVA for cancer samples described in Table 7B. It indicated that age and gender groups were significant factors with respect to MI and SAM (for SAH, only age group not gender group was significant) in lung cancer cases. With liver cancer cases, as only male patients were observed, therefore no result was obtained on gender group but age factor is significant with respect to MI. In other cancers, age group factor is slightly significant at significant level $\alpha=0.1$ with respect to SAM and SAH, not MI.

TABLE 13

Results of t-test in 80 Lung Cancer Samples

| Response Variable | Mean | p-value | Significance |
|---|---|---|---|
| SAM | 137.6983 | 9.60E−16 | **** |
| SAH | 462.522 | 1.03E−10 | **** |
| MI | 0.3840688 | 1.08E−12 | **** |

As can be seen from Table 13, 80 cases of lung cancer samples were tested and analyzed with R as well. The results indicated that SAM and MI were significantly reduced and SAH was significantly increased in cancer patients compared with normal people.

TABLE 14

Results of t-test in Diseases from Table 7C

| Diseases | Response Variable | Mean | p-value | Significance |
|---|---|---|---|---|
| Cerebrovascular diseases | SAM | 415.4277 | 0.6064 | |
| Cerebrovascular diseases | SAH | 363.3671 | 0.03015 | ** |
| Cerebrovascular diseases | MI | 1.163449 | 2.03E−05 | **** |
| Depression | SAM | 337.385 | 0.3531 | |
| Depression | SAH | 442.379 | 0.01176 | ** |
| Depression | MI | 0.87051 | 4.81E−06 | **** |
| Parkinson's Disease | SAM | 285.5726 | 0.07684 | * |
| Parkinson's Disease | SAH | 794.5792 | 0.06972 | * |
| Parkinson's Disease | MI | 0.74988 | 7.18E−06 | **** |
| Depression + Parkinson's | SAM | 363.4532 | 0.5513 | |
| Depression + Parkinson's | SAH | 490.9231 | 0.00325 | *** |
| Depression + Parkinson's | MI | 0.9868218 | 4.95E−07 | **** |

As can be seen from Table 14, MI is a better and sensitive indicator for identifying diseases such as cerebrovascular disorders, depression and Parkinson's disease, and it was significantly reduced in these diseases.

TABLE 15

SAM Levels and Methylation Index (MI) in Brian Diseases

| Diseases (Case #) | % of SAM > 240 nM | % of SAM > 120 nM | % of MI > 2 | % of MI > 1 | % of MI < 0.5 |
|---|---|---|---|---|---|
| Normal (311) | 90.36 | 96.79 | 6.95 | 42.47 | 16.98 |
| Normal (81) | 69.14 | 95.06 | 46.91 | 77.90 | 8.64 |
| Cerebral hemorrhage (10), embolism (6), infarction (4) | 85 | 90 | 0 | 65 | 0 |
| Parkinson's Disease (10), Depression (10) | 70 | 90 | 0 | 25 | 20 |

As can be seen from Table 15, the percentages of SAM levels greater than 120 nM were comparable between normal people and patients with Parkinson's disease or depression, However, significant increase in the percentage of patients having MI less than 0.5 (about 8.64% normal people with MI<0.5 from Table 7 vs. 20% of Parkinson's disease and depressed patients), and significant decrease in the percentage of people having MI greater than 1 were observed, It suggested that MI could be a good marker for Parkinson's disease and depression.

The less the MI, the higher probability Parkinson's disease or depression might occur. On the other hand, in the cases of Cerebrovascular diseases, such as cerebral hemorrhage, embolism and infarction, no obvious changes in SAM levels and MI were observed in this study.

Table 15 summarizes the ranges and average of MI for cases in Example 24. It is consistent with the t-test results that normal people has significantly higher MI (averagely 2.2) than diseased patients (averagely <1.56). The obvious difference between normal and diseased group can also been seen from the maximum MI.

In the cases of cancers, we can see some samples had MI values fell between 4 and 6, therefore the average MI in cancer groups were relatively higher than other diseased groups. The relatively higher MI in cancer samples is due to relatively higher SAM. This is consistent with a report by Alissa K. et al (Chest. 2007. 132(4): 1247-1252.) which serum SAM levels were elevated in patients with lung cancer as compared to smokers with benign lung disorders and healthy nonsmokers. There were no significant correlations between SAM levels and tumor cell types, nodule size, or other demographic variables. The temporarily high SAM levels may be caused by release of intracellular SAM from cells into blood stream (as can be confirmed by IHC staining of SAM from cancer cells) at some stage of cancer progression. Therefore, in our cancer samples, we could see wide ranges of MI values observed in all types of cancers. As only certain stage of cancer development that SAM release is significant, once release is completed, SAM level in blood stream won't maintain at the high level, which contributes to the big ranges of SAM levels observed for all cancer types.

In the case of 68 cases of cerebrovascular diseases, there is only one sample has MI as 5.67. All others were less than 2.09. If we consider that sample as abnormal (or an outlier), the average MI for that group would be less than 1. Therefore, cerebrovascular diseases would be among other diseases in evaluating the range and average value of MI.

TABLE 16

Range and Average of MI from Study

| Group | Range of MI | Average MI |
|---|---|---|
| Normal | 0.40-6.50 | 2.22 |
| All diseases | 0.07-5.67 | 0.87 |
| Cerebrovascular diseases | 0.36-5.67 | 1.06 |
| Parkinson's Disease | 0.08-1.86 | 0.75 |
| Depression | 0.36-1.94 | 0.87 |
| Diabetes | 0.11-3.86 | 0.86 |
| HBP | 0.10-1.19 | 0.92 |
| Heart disease | 0.07-1.95 | 0.78 |
| Inflammation | 0.28-2.13 | 0.82 |
| Kidney disease | 0.10-1.92 | 0.7 |
| Liver diseases | 0.22-2.50 | 0.89 |
| Pulmonary diseases | 0.13-1.49 | 0.79 |
| Other Cancers | 0.10-5.42 | 0.81 |
| Liver Cancer | 0.13-4.98 | 1.56 |
| Lung Cancer | 0.06-5.42 | 0.68 |

Example 25

Samples from a Group Annual Health Examination (Study #4)

The study was done among a random group of people (a manufacture in Changsha, Hunan Province, China) from the test results of its annual physical examinations. Normal plasma was processed and frozen within 5-7 hours after blood withdraw with EDTA as an anticoagulant. Plasma was collected and stored frozen below −20° C. Subsequent examinations and other tests reviewed by doctors before diagnosis were finalized and then group the cases accordingly. The case information is summarized in Table 17. We performed the t-tests on the 303 healthy individuals and 271 patients including sub-healthy group people. The results were shown in Table 18, which indicated that diseased group has significantly low SAM and methylation index as well as significantly increased SAH levels compared to healthy people. This study was in agreement with Study #3 that methylation index is a healthy indicator to distinguish healthy subjects from un-healthy subjects. Methylation index can be used as a screening biomarker to identify the existence of any of potential unfavorable health conditions of human beings though further examinations are necessary for a diagnosis of any potential diseases. It is therefore recommended as a part of annual health examination panel.

TABLE 17

Sample Types and Information in Annual Health Study

| Case Type | Case # |
|---|---|
| Healthy People | 303 |
| Sub-health condition: at least one blood tests were off-normal but no clear diagnosis was given | 53 |
| Benign liver disease: Fatty liver, hepatic cysts, schistosoma liver, hepatic hemangioma, diffuse parenchymal liver disease, alcoholic liver | 76 |
| Hypertension (HBP) | 41 |
| Kidney disease: Renal cysts, kidney stones, hydronephrosis | 15 |
| Cardiovascular diseases: heart attack, atherosclerosis, high blood lipid | 29 |
| Inflammation: gall bladder Gallbladder polyps, gallbladder stones, cholecystitis, TB, breasts lobular, gynecological | 16 |
| Diabetes | 19 |
| Other diseases: cerebrovascular complications, prostatic hypertrophy, pulmonary diseases | 22 |

TABLE 18

Results of t-test for Healthy vs. all other Disease and Sub-healthy Groups Study

| Response Variable | p-value | Significance |
|---|---|---|
| SAM | 0.0001353 | **** |
| SAH | 0.01636 | ** |
| MI | 0.08857 | * |

Example 26

SAM and MI in Liver Diseases (Study #5)

The study was done for patients with variety of liver diseases from the in-patient department of Infectious Diseases in the First Affiliated Hospital, Xiangyang Medical School, Zhongnan University, China. Seven cancer samples were obtained from patients with definite diagnosis from the Out-patient Department. The EDTA plasma samples were collected and frozen in −20° C. within 30 minutes after blood drawn.

Our experiment showed no differences in SAM and SAH levels using serum or plasma samples. Therefore, we employed the data from normal samples in Table 6 to compare with the data from liver diseases in this study. Using direct competitive ELISA, we tested 46 hepatitis samples (severe virus hepatitis), 14 liver cancer samples, 20 various degrees of cirrhosis plasma and 19 advanced stage of cirrhosis when liver function cannot be sustained (liver failure).

Table 19 showed differences of SAM levels and MIs in different groups. The SAM levels and MIs were much reduced in all liver disease types. None of the liver disease samples tested had MI greater than 2 and very few of liver carcinoma and hepatitis had MI greater than 1. In the case of liver failure, SAM level were all below 120 nM. It is not hard to understand why this may happen as liver is the main organ in human body to produce SAM and SAH. The more destructive the liver disease, the less SAM and SAH are to be produced.

TABLE 19

SAM Levels and Methylation Index (MI) in Liver Diseases

| Group | # Case | # SAM > 240 nM(%) | # SAM > 120 nM(%) | % of MI > 2 | % of MI > 1 | % of MI < 0.5 |
|---|---|---|---|---|---|---|
| Normal | 81 | 56 (69.14%) | 77 (95.06%) | 46.91 | 67.90 | 8.64 |
| Hepatitis | 46 | 2 (4.35%) | 9 (19.57%) | 0 | 2.56 | 94.87 |
| Carcinoma | 14 | 1 (7.14%) | 4 (28.57%) | 0 | 7.14 | 85.71 |
| Cirrhosis | 20 | 1 (5.00%) | 3 (15.00%) | 0 | 0 | 89.47 |
| Liver failure | 19 | 0 | 0 | 0 | 0 | 100 |

As it is well known that SAM and SAH levels can be affected by gender, age, race, diet, body weight, neuroendocrine, health and other unknown factors and are part of normal metabolites, about 10-80% of the standard deviation may be observed depending on situations. When normal plasma average SAM and standard deviation was at 386.66±216.20 nM, hepatitis at much reduced 101.42±83.12 nM, liver carcinoma at 104.96±82.63 nM, cirrhosis at 92.95±62.41 nM, liver failure at 66.46±29.77 nM. Further analyses using 120 nM and 240 nM as cutoff values separately to identify liver diseases with SAM level, the detected numbers and detection rates for all groups were calculated (See Table 20).

TABLE 20

SAM Levels in Diagnosis of Liver Diseases

| Group | Case No. | SAM (nM) Average | Standard Deviation | SAM = 120 nM Cutoff Detected Number | Detection Rate (%) | SAM = 240 nM Cutoff Detected Number | Detection Rate (%) |
|---|---|---|---|---|---|---|---|
| Normal | 81 | 386.66 | 216.20 | 2 | 2.46 | 20 | 24.69 |
| Hepatitis | 46 | 101.42 | 83.12 | 37 | 80.43 | 44 | 95.65 |
| Carcinoma | 14 | 104.96 | 82.63 | 10 | 71.43 | 13 | 92.86 |
| Cirrhosis | 20 | 92.95 | 62.41 | 17 | 85.00 | 19 | 95.00 |
| Liver failure | 19 | 66.46 | 29.77 | 19 | 100 | 19 | 100 |

Using the 240 nM SAM cutoff, detection rate for normal group (false positive) was 24.69%, whereas detection rates for all liver disease groups were 92.86-100% (false negative rates were reduced to 0-7.14%). With the 120 nM SAM cutoff, detection rate for normal group (false positive rate) was reduced significantly to 2.67% whereas detection rates for liver diseases were still as high as 71.43-100% ((false negative rates were between 0-28.57%). With higher cutoff, false positive rate can be as high as 24.69%. By reducing the cutoff, false positive rate was much decreased, yet detection rates for liver disease groups were also decreased causing the false negative rate to increase. For liver failure group, the detection rate was still 100% with 120 nM cutoff or 240 nM cutoff. Refer to other liver biomarkers from lab results or other relevant examination reports when SAM level falls within 120-240 nM or even if below 120 nM. The best way to the unavoidable overlap of values of a biomarker between diseased and healthy conditions is to get to know each individual's baseline reference profile and dynamically monitor the changes.

Example 27

SAM and MI in Healthy Human Saliva (Study #6)

No reports on measuring SAM and SAH levels from human saliva samples has been reported in the prior art. In this study, we tested 30 normal human saliva samples from volunteers. Samples (a) were collected about 1-2 hours post-breakfast after mouth-rinse a couple of times; samples (b) were collected right after samples (a) and after brushing teeth with toothpaste; samples (c) were collected 2-4 hours after samples (b) were collected without any food intake in between. The samples were centrifuged at 4° C. for 5-10 minutes at 10,280×g and frozen till the next day for measurement of SAM and SAH of different time points at the same time with and without dilution. The SAM and SAH competitive ELISA kits were used to measure SAM and SAH in phosphate incubation buffer as well as plasma matrix, respectively.

The results indicated that after brushing teeth with toothpaste, SAM and SAH levels were shown increased significantly, which is believed to be non-specific inhibition causing OD450 to be significantly reduced, thereby concentrations of this group were calculated much higher. There were a few samples that also showed non-specific inhibition including volunteers who were taking traditional Chinese medicines and smoked heavily around the time of saliva collection. These samples were removed from the results.

An ELISA kit designed for measuring plasma samples was used for measuring saliva samples and the results are shown in Table 21. The results showed the nonspecific increase caused by brushing teeth on SAM is 7.4-8.4 folds, and on SAH is 2.9-3.5 folds. The SAM values from sample (c) (i.e. 2-4 hours after brushing the teeth without any food intake) is about 2.8-3.1 folds higher than samples (a) (samples taken 1-2 hours after breakfast and before brushing teeth), and SAH about 1.8-2.6 folds higher. The ranges are also very broad. The reason why SAM and SAH values from samples (c) were higher than those of sample (a) may be related to oral environment especially human mouth flora, which is considered to be determined by each person's genetic background or makeup. Genetic factors have a lot much impact on each individual's mouth flora than external environmental factors. Like seen from the results of plasma samples, the broad ranges and big standard deviations of SAM and SAH values from saliva samples also indicated that SAM and SAH levels are affected by plenty of enzymes and environmental molecules and factors in several metabolic pathways, many of which are determined by differenced of genetic materials of each individual. Thus, a variety exists among individuals. In order to best monitor SAM and SAH levels from saliva, keep oral environment (food, medication, smoking, drinks, alcohol, etc.) similar between tests and collect saliva samples at a fixed time of a day.

TABLE 21

SAM and SAH levels from saliva samples

| | Samples | Mean (nM) | Standard deviation (nM) | Range |
|---|---|---|---|---|
| SAM | Avg. Sample (a) | 102 | 71 | (30 nM, 257 nM) |
| | Avg. Sample (b) | 852 | 719 | (30 nM, 2449 nM) |
| | Avg. Sample (c) | 309 | 241 | (30 nM, 664 nM) |
| SAH | Avg. Sample (a) | 184 | 119 | (31 nM, 717 nM) |
| | Avg. Sample (b) | 612 | 361 | (122 nM, 1112 nM) |
| | Avg. Sample (c) | 479 | 322 | (39 nM, 695 nM) |

All patents, patent applications and publications cited in this application including all cited references in those patents, applications and publications, are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting.

It is to be understood that the terms used herein are merely descriptive rather than limiting and that various changes, numerous equivalents may be made without departing from the spirit or scope of the claimed invention.

What is claimed is:

1. A method for screening, diagnosing and monitoring a disease or condition in a subject comprising the steps of: (a) obtaining a biological sample from a patient to be screened, diagnosed or monitored; (b) determining using an immunoassay the quantity of SAM and SAH in said biological sample; (c) calculating the methylation index of said biological sample; (d) comparing said methylation index of step (c) to the patient's baseline reference methylation index profile; and (e) determining if the quantity(ies) of said SAM, SAH and methylation index in said biological sample is(are) indicative of the presence, absence or stages of any diseases or conditions; and wherein said immunoassay in step (b) utilizes a monoclonal antibody derived from hybridomas having the designation from the China Center For Type Culture Collection (CCTCC) number C2017178 and number C2017179.

2. The method of claim 1, wherein said reference profile for screening, diagnosing and monitoring, comprises levels of SAM, SAH and methylation index that are differentially present at a level that is statistically significant, the profile profiling being of at least one of one or more disease, the at least one reference methylation index profile profiling at least one of: one or more disease, cerebrovascular diseases, Parkinson's disease, depression, diabetes, HBP, heart disease, inflammation, kidney disease, liver diseases, pulmonary diseases, lung cancer, liver cancer and other cancers.

3. A method of claim 1, for screening and diagnosing whether a subject suffers from liver disease, comprising: identifying, using an anti-SAM antibody, whether said subject has a serum or plasma human SAM concentration at a given threshold value, and thereby diagnosing whether the subject suffers from liver disease.

4. The method of claim 3, wherein said liver disease is acute liver disease selected from the group consisting of liver failure, acute viral hepatitis, carcinoma and cirrhosis.

5. The method of claim 3, wherein said liver disease is chronic liver disease, selected from the group consisting of fatty liver, hepatic cysts, schistosoma liver, hepatic hemangioma, diffuse parenchymal liver disease, and alcoholic liver.

6. The method of claim 3, for monitoring liver health in a patient, further including measuring the level of one or more additional biomarkers selected from the group consisting of bilirubin (total or fractionated, conjugated or unconjugated), ammonia, carbohydrate-deficient transferring (CDT), alanine aminotransferase (ALT), alkaline phosphatase (ALP), serum glutamic pyruvic transaminase (SGPT), aspartate aminotransferase (AST), serum glutamic oxaloacetic transaminase (SGOT), albumin, total protein (i.e., plasma proteins), gamma-glutamyl transferase (GGT), gamma-glutamyl transpeptidase (GGTP), lactic acid dehydrogenase (LDH), prothrombin time, or combinations thereof and comparing said SAM levels and said biomarkers in said sample to a level of said SAM and said biomarkers of to a normal control sample; and determining the health condition of the liver in said patient based on said comparison.

7. The method of claim 1, wherein said immunoassay is an ELISA or other homogeneous immunoassays.

8. The method of claim 1, wherein said immunoassay is performed in a colloidal gold strip or other dry quantitative or qualitative detection devices.

* * * * *